US008178333B2

(12) United States Patent
Mijts et al.

(10) Patent No.: US 8,178,333 B2
(45) Date of Patent: May 15, 2012

(54) BIOCATALYTIC PROCESSES FOR THE PREPARATION OF SUBSTANTIALLY STEREOMERICALLY PURE FUSED BICYCLIC PROLINE COMPOUNDS

(75) Inventors: Benjamin Mijts, Belmont, CA (US); Sheela Muley, Fremont, CA (US); Jack Liang, San Mateo, CA (US); Lisa M. Newman, San Jose, CA (US); Xiyun Zhang, Fremont, CA (US); James Lalonde, Palo Alto, CA (US); Michael D. Clay, Menlo Park, CA (US); Jun Zhu, Sunnyvale, CA (US); John M. Gruber, El Dorado Hills, CA (US); Jeffrey Colbeck, Menlo Park, CA (US); John D. Munger, Jr., Redwood City, CA (US); Jagadeesh Mavinahalli, Singapore (SG); Roger Sheldon, Hoog Keppel (NL)

(73) Assignee: Codexis, Inc., Redwood City, CA (US)

( * ) Notice: Subject to any disclaimer, the term of this patent is extended or adjusted under 35 U.S.C. 154(b) by 189 days.

(21) Appl. No.: 12/490,190

(22) Filed: Jun. 23, 2009

(65) Prior Publication Data

US 2010/0063300 A1     Mar. 11, 2010

Related U.S. Application Data

(60) Provisional application No. 61/075,243, filed on Jun. 24, 2008.

(51) Int. Cl.
*C12N 9/00* (2006.01)
*C07H 21/04* (2006.01)

(52) U.S. Cl. ............... 435/183; 435/69.1; 435/320.1; 536/23.1

(58) Field of Classification Search .............. 435/69.1, 435/320.1, 183; 536/23.2
See application file for complete search history.

(56) References Cited

U.S. PATENT DOCUMENTS

| | | | |
|---|---|---|---|
| 4,183,857 A | 1/1980 | Kollmeyer | |
| 4,225,499 A | 9/1980 | Kollmeyer | |
| 6,537,746 B2 | 3/2003 | Arnold et al. | |
| 6,562,958 B1 | 5/2003 | Breton et al. | |
| 7,012,066 B2 | 3/2006 | Saksena et al. | |
| 7,208,302 B2 | 4/2007 | Alexeeva et al. | |
| 7,214,786 B2 | 5/2007 | Kovalic et al. | |
| 7,241,796 B2 | 7/2007 | Farmer et al. | |
| 7,288,565 B2 | 10/2007 | Kanie | |
| 7,314,974 B2 | 1/2008 | Cao et al. | |
| 7,504,490 B1 | 3/2009 | Weinstock et al. | |
| 7,776,887 B2 | 8/2010 | Tanoury et al. | |
| 7,820,671 B2 | 10/2010 | Babine et al. | |
| 2004/0029129 A1 | 2/2004 | Wang et al. | |
| 2010/0137583 A1 | 6/2010 | Babine et al. | |

FOREIGN PATENT DOCUMENTS

| | | |
|---|---|---|
| EP | 0004107 | 9/1979 |
| EP | 0008813 | 3/1980 |
| EP | 0010799 | 5/1980 |
| EP | 0090362 A2 | 3/1983 |
| EP | 2105507 A1 | 3/2003 |
| EP | 1304335 B1 | 10/2009 |
| EP | 1878720 B1 | 6/2010 |
| EP | 1934179 B1 | 7/2010 |
| JP | 11-253162 | 9/1999 |
| WO | WO95/22625 | 8/1995 |
| WO | WO95/33836 | 12/1995 |
| WO | WO96/00787 | 1/1996 |
| WO | WO97/20078 | 6/1997 |
| WO | WO97/35966 | 10/1997 |
| WO | WO98/27230 | 6/1998 |
| WO | WO00/18369 | 4/2000 |
| WO | WO00/20824 | 4/2000 |
| WO | WO00/42651 | 7/2000 |
| WO | WO01/75767 | 2/2001 |
| WO | 0208244 A2 | 1/2002 |
| WO | 0218369 A2 | 3/2002 |
| WO | 03035060 A1 | 5/2003 |
| WO | 03062265 A2 | 7/2003 |
| WO | 03080855 A2 | 10/2003 |
| WO | 03097646 A1 | 11/2003 |
| WO | 2004113295 A2 | 12/2004 |
| WO | 2005080382 A1 | 9/2005 |
| WO | 2007022459 A2 | 2/2007 |
| WO | WO 2007/022459 | 2/2007 |
| WO | WO 2007/029086 | 3/2007 |
| WO | WO 2007/075790 | 5/2007 |
| WO | 2008082508 A2 | 7/2008 |
| WO | WO 2008/082508 | 7/2008 |
| WO | 2010117936 A1 | 10/2010 |
| WO | 2010117939 A1 | 10/2010 |
| WO | 2010126881 A1 | 11/2010 |

OTHER PUBLICATIONS

Pel et al. Feb., 2007 (online Jan. 28, 2007); Genome sequencing and analysis of the versatile cell factor *Aspergillus niger* CBS 513.88; Nature Biotechnology 25(2):221-231.*
GENBANK accession No. L38858 for *Aspergillus niger*; Apr. 26, 1996.*
GENBANK accession No. XM 001822832 for *Aspergillus oryzae*; Apr. 11, 2008.*
Notification of Transmittal of the International Search Report and the Written Opinion of the International Searching Authority, or the Declaration, PCT/US2009/048255, mailed Mar. 9, 2010.
Kohler et al., "Enantioselective Biocatalytic Oxidative Desymmetrization of Substituted Pyrrolidines," Angew. Chem. Int. Ed., 49, 2182-2184, 2010.
Znabet et al., "A highly efficient synthesis of telaprevir by strategic use of biocatalysis and multicomponent reactions," Chem. Comm. 46, 7918-7920, 2010.
Alexeeva et al. (2002) *Angew. Chem. Int. Ed.* "Deracemization of a-Methylbenzylamine Using an Enzyme Obtained by In Vitro Evolution" 41: 3177-3180.
Atkin et al (2008) *J.Mol.Biol.*"The Structure of Monoamine Oxidase from *Aspergillus niger* Provides a Molecular Context for Improvements in Activity Obtained by Directed Evolution" 384, 1218-1231.
Atkin et al. (2008) *Acta Crystallographica.* "Cloning, expression, purification, crystallization and preliminary X-ray diffraction analysis of variants of monoamine oxidase from *Aspergillus niger*" F64, 182-185.
Bailey et al. (2007) *Chem. Commun.*, "A Template-based Mnemonic for Monoamine Oxidase (MAO-N) Catalyzed Reactions and its Application to the Chemo-Enzymatic Deracemisation of the Alkaloid (±)-crispine A" 3640-3642.
Carr et al. (2005) *ChemBioChem.* "Directed Evolution of an Amine Oxidase for the Preparative Deracemisation of Cyclic Secondary Amines" 6, 637-639.

Carr et al. (2003) *Angew. Chem. Int. Ed.*, "Directed Evolution of an Amine Oxidase Possessing both Broad Substrate Specificity and High Enantioselectivity", 42,4807-4810.
Delalu et al. (1999) *J. Heterocyclic Chem*. "Synthesis and NMR investigation of 3,4-diazabicyclo [4.3.0] non-2-ene and N,N'-azo-3-azabicyclo[3.3.0] octane Xray crystal structure analysis of a new tetrazene derivative," 36, 681-686.
Dunsmore et al. (2005) *J Am Chem Soc*, "A Chemo-Enzymatic Route to Enantiomerically Pure Cyclic Tertiary Amines," 128(7):2224-5 and S1-S7.
Edmondson et al. (2004) *Current Medicinal Chemistry* "Structure and Mechanism of Monoamine Oxidase" 11, 1983-1993.
Elkhatib et al. (1998) *Int'l Journal Chemical Kinetics*, "Kinetics of Dehydrohalogenation of N-Chloro-3-Azabicyclo[3,3,0] Octane in Alkaline Medicum. NMR and ES/MS Evidence of the Dimerization of 3-Azabicyclo[3,3,0]Oct-2-Ene" 30, 129-136.
Eve et al. (2007) *Chem. Commun.*, "Enantioselective Oxidation of O-methyl-N-hydroxylamines Using Monoamine Oxidase N as a Catalyst" 1530-1531.
Farmer et al. (2005) *Letters in Drug Design & Discovery* Inhibitors of Hepatitis C Virus NS3•4A Protease: P2 Proline Variants 2(7): 497-502.
Garcia-Urdiales et al. "Enantioselective Enzymatic Desymmetrization in Organic Synthesis," *Chem. Rev.* (2005) 105: 313-54.
Kay et al. (2007) *J Am Chem Soc*, "Characterization of the Covalently bound Anionic Flavin Radical in Monamine Oxidase A by Electron Paramagnetic Resonamce," 129(51):16091-7. Epub Nov. 29, 2007.
Li et al. (2006) *Biochemistry* "Functional Rode of the "Aromatic Cage" in Human Monoamine Oxidase B: Structures and Catalytic Properties of Tyr435 Mutant Proteins" 45, 4775-4784.
Ma et al. (2004) *J.Mol.Biol*. "Structure of Rat Monoamine Oxidase A and Its Specific Recognitions for Substrates and Inhibitors" 338, 103-114.
Malcolm et al. (2006) *Antimicrob. Agents Chemother*. "SCH 503034, a Mechanism-Based Inhibitor of Hepatitis C Virus NS3 Protease, Suppresses Polyprotein Maturation and Enhances the Antiviral Activity of Alpha Interferon in Replicon Cells" 50(3): 1013-20.
Monn et al. 1994 *J. Org. Chem*. A Concise, Stereocontrolled Thiazolium Ylide Approach to Kainic Acid, 59, 2773-8.
Perni et al. (2006) *Antimicrob. Agents Chemother*. Preclinical Profile of VX-950, a Potent, Selective, and Orally Bioavailable Inhibitor of Hepatitis C Virus N53-4ASerine Protease 50(3): 899 909.
Ralph et al. (2007) *Biochemistry*, "Insights into the Mechanism of Flavoprotein-Catalyzed Amine Oxidation from Nitrogen Isotope Effects on the Reaction of N-Methyltryptophan Oxidase," 46(25):7655-64. Epub Jun. 2, 2007.
Schilling et al. (1995) *Biochim. Biophys. Acta*. "Amine oxidases from *Aspergillus niger* : identification of a novel flavin-dependent enzyme" 1243: 529 37.
Szutowicz et al., (1984) *Anal. Biochem*. "Colorimetric Assay for Monoamine Oxidase in Tissues Using Peroxidase and 2,2'-Azino(3-ethtylbenzthaizoline-6-sulfonic Acid) as Chromogen," 138:86-94.
Tipton et al. (2004) *Current Medicinal Chemistry* "Monoamine Oxidases: Certainties and Uncertainties" 11, 1965-1982.
Trabocchi et al. (2008) *Amino Acids* "Synthesis of a Bicyclic Amino acid as a Constrained Gly-Asn Dipeptide Isostere" 35: 37-44.
Zhou et al. "A One-Step Fluorometric Method for the Continuous Measurement of Monoamine Oxidase Activity," 1997 *Anal. Biochem.* 253:169-74.

* cited by examiner

*Primary Examiner* — Karen Carlson
(74) *Attorney, Agent, or Firm* — Codexis, Inc.

(57) ABSTRACT

The present disclosure provides monoamine oxidase enzymes and methods of their use in biocatalytic processes for the preparation of substantially enantiomerically pure heterobicyclic compounds of the following structural formulas,

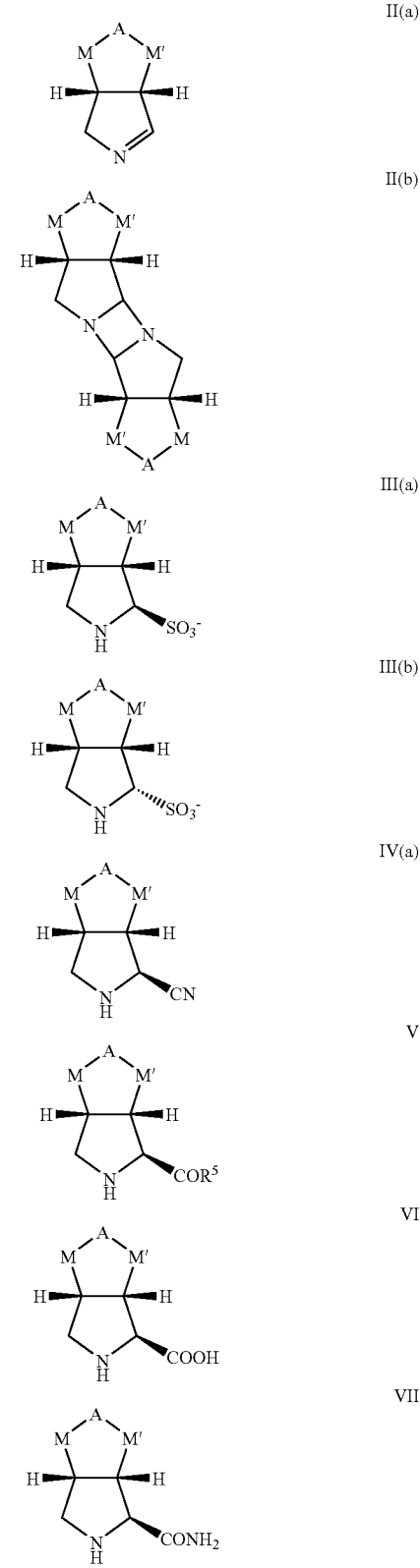

wherein A, M, M', and $R^5$ are as described herein.

28 Claims, No Drawings

SEQUENCE LISTING

<160> NUMBER OF SEQ ID NOS: 36

<210> SEQ ID NO 1
<211> LENGTH: 1485
<212> TYPE: DNA
<213> ORGANISM: Artificial Sequence
<220> FEATURE:
<223> OTHER INFORMATION: Aspergillus Niger monoamine oxidase (MAON)

<400> SEQUENCE: 1

```
atgaccagcc gcgacggcta tcagtggacc ccggaaacgg gtctgaccca gggcgtaccg      60
tccctgggtg tcatttcgcc gccgactaac atcgaagata ccgataagga cgggcccttgg     120 gatgtcattg tcattggggg cgggtattgt gggctgaccg caacccgtga tttaaccgtc     180
gcagggttca agacgctgct gctggaggcc cgtgatcgta ttggtggccg ctcctggagc     240
agtaatattg acggttaccc gtatgagatg ggtggcactt gggttcattg gcatcaatct     300
cacgtgtggc gtgaaatcac gcgttataaa atgcacaacg cgctgtctcc atcatttaac     360
ttttcacgtg gcgtgaatca cttccaactg cgtaccaatc cgaccaccag tacgtacatg     420
acgcacgaag cggaggatga actgctgcgt agcgcattgc ataaattcac caatgtcgac     480
ggcactaatg gccgtacagt gttgccgttc ccacatgata tgtttatgt gccggaattt     540
```

```
cgcaagtatg acgaaatgtc atattccgaa cgcattgacc agatccgcga cgaactgtct    600
ttgaacgaac gctctagttt agaggctttc attttattat gtagcggtgg caccctggaa    660
aactccagct ttggtgaatt tctgcattgg tgggcaatgt cgggttacac gtatcagggc    720
tgtatggatt gtttaatctc ctataaattt aaggatggcc agagtgcgtt cgcgcgtcgc    780
ttctgggaag aagccgctgg cactggccgt ctgggctatg tctttggttg tccggtgcgt    840
tctgtggtga acgaacgcga cgcagcacgt gttaccgcac gtgacggtcg cgaattcgca    900
gcgaaacgtt tggtttgcac gattccgctg aacgtattga gtactattca gtttagccca    960
gcactgtcca cggaacgcat ctccgctatg caggcaggcc atgttaacat gtgcaccaaa   1020
gtgcatgcgg aagtcgataa taaggatatg cgttcatgga cgggtatcgc ctatccgttc   1080
aacaaattat gctacgctat cggcgatggc acgaccccag cgggtaatac gcatctggtg   1140
tgcttcggga cagacgcgaa tcatatccag ccggacgagg acgtgcgcga aacgttgaaa   1200
gccgttggcc aactggcgcc tgggactttc ggtgtcaaac gtctggtctt ccacaactgg   1260
gtaaaggatg aatttgccaa aggcgcgtgg ttcttcagcc gcccaggcat ggtttcagag   1320
tgcctgcagg gtctgcgcga gaaacaccgt ggtgtcgtgt ttgcaaactc cgattgggcc   1380
ttaggttggc gtagttttat cgatggtgct atcgaggagg caccgcgc agcgcgtgtt   1440 gtactggagg aactggggac caagcgcgag gtgaaggccc gcctg               1485

<210> SEQ ID NO 2
<211> LENGTH: 495
<212> TYPE: PRT
<213> ORGANISM: Artificial Sequence
<220> FEATURE:
<223> OTHER INFORMATION: Aspergillus Niger monoamine oxidase (MAON)

<400> SEQUENCE: 2

Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Thr Asn Ile Glu
            20                  25                  30

Asp Thr Asp Lys Asp Gly Pro Trp Asp Val Ile Val Ile Gly Gly Gly
        35                  40                  45

Tyr Cys Gly Leu Thr Ala Thr Arg Asp Leu Thr Val Ala Gly Phe Lys
    50                  55                  60

Thr Leu Leu Leu Glu Ala Arg Asp Arg Ile Gly Gly Arg Ser Trp Ser
65                  70                  75                  80

Ser Asn Ile Asp Gly Tyr Pro Tyr Glu Met Gly Gly Thr Trp Val His
                85                  90                  95

Trp His Gln Ser His Val Trp Arg Glu Ile Thr Arg Tyr Lys Met His
            100                 105                 110

Asn Ala Leu Ser Pro Ser Phe Asn Phe Ser Arg Gly Val Asn His Phe
        115                 120                 125

Gln Leu Arg Thr Asn Pro Thr Thr Ser Thr Tyr Met Thr His Glu Ala
    130                 135                 140

Glu Asp Glu Leu Leu Arg Ser Ala Leu His Lys Phe Thr Asn Val Asp
145                 150                 155                 160

Gly Thr Asn Gly Arg Thr Val Leu Pro Phe Pro His Asp Met Phe Tyr
                165                 170                 175

Val Pro Glu Phe Arg Lys Tyr Asp Glu Met Ser Tyr Ser Glu Arg Ile
            180                 185                 190

Asp Gln Ile Arg Asp Glu Leu Ser Leu Asn Glu Arg Ser Ser Leu Glu
        195                 200                 205
```

Ala Phe Ile Leu Leu Cys Ser Gly Gly Thr Leu Glu Asn Ser Ser Phe
    210                 215                 220

Gly Glu Phe Leu His Trp Trp Ala Met Ser Gly Tyr Thr Tyr Gln Gly
225                 230                 235                 240

Cys Met Asp Cys Leu Ile Ser Tyr Lys Phe Lys Asp Gly Gln Ser Ala
                245                 250                 255

Phe Ala Arg Arg Phe Trp Glu Glu Ala Ala Gly Thr Gly Arg Leu Gly
            260                 265                 270

Tyr Val Phe Gly Cys Pro Val Arg Ser Val Val Asn Glu Arg Asp Ala
        275                 280                 285

Ala Arg Val Thr Ala Arg Asp Gly Arg Glu Phe Ala Ala Lys Arg Leu
    290                 295                 300

Val Cys Thr Ile Pro Leu Asn Val Leu Ser Thr Ile Gln Phe Ser Pro
305                 310                 315                 320

Ala Leu Ser Thr Glu Arg Ile Ser Ala Met Gln Ala Gly His Val Asn
                325                 330                 335

Met Cys Thr Lys Val His Ala Glu Val Asp Asn Lys Asp Met Arg Ser
            340                 345                 350

Trp Thr Gly Ile Ala Tyr Pro Phe Asn Lys Leu Cys Tyr Ala Ile Gly
        355                 360                 365

Asp Gly Thr Thr Pro Ala Gly Asn Thr His Leu Val Cys Phe Gly Thr
    370                 375                 380

Asp Ala Asn His Ile Gln Pro Asp Glu Asp Val Arg Glu Thr Leu Lys
385                 390                 395                 400

Ala Val Gly Gln Leu Ala Pro Gly Thr Phe Gly Val Lys Arg Leu Val
                405                 410                 415

Phe His Asn Trp Val Lys Asp Glu Phe Ala Lys Gly Ala Trp Phe Phe
            420                 425                 430

Ser Arg Pro Gly Met Val Ser Glu Cys Leu Gln Gly Leu Arg Glu Lys
        435                 440                 445

His Arg Gly Val Val Phe Ala Asn Ser Asp Trp Ala Leu Gly Trp Arg
    450                 455                 460

Ser Phe Ile Asp Gly Ala Ile Glu Glu Gly Thr Arg Ala Ala Arg Val
465                 470                 475                 480

Val Leu Glu Glu Leu Gly Thr Lys Arg Glu Val Lys Ala Arg Leu
                485                 490                 495

<210> SEQ ID NO 3
<211> LENGTH: 1491
<212> TYPE: DNA
<213> ORGANISM: Artificial Sequence
<220> FEATURE:
<223> OTHER INFORMATION: variant monoamine oxidase

<400> SEQUENCE: 3
atgaccagcc gcgacggcta tcagtggacc ccggaaacgg gtctgaccca gggcgtaccg      60
tccctgggtg tcatttcgcc gccgactaac atcgaagata ccgataagga cgggccttgg     120
gatgtcattg tcattggggg cgggtattgt gggctgaccg caacccgtga tttaaccgtc     180
gcagggttca agacgctgct gctggaggcc cgtgatcgta ttggtggccg ctcctggagc     240
agtaatattg acggttaccc gtatgagatg ggtggcactt gggttcattg gcatcaatct     300
cacgtgtggc gtgaaatcac gcgttataaa atgcacaacg cgctgtctcc atcatttaac     360
ttttcacgtg gcgtgaatca cttccaactg cgtaccaatc cgaccaccag tacgtacatg     420
acgcacgaag cggaggatga actgctgcgt agcgcattgc ataaattcac caatgtcgac     480

```
ggcactaatg gccgtacagt gttgccgttc ccacatgata tgttttatgt gccggaattt      540
cgcaagtatg acgaaatgtc atattccgaa cgcattgacc agatccgcga cgaactgtct      600
ttgaacgaac gctctagttt agaggctttc attttattat gtagcggtgg caccctggaa      660
aactccagct ttggtgaatt tctgcattgg tgggcaatgt cgggttacac gtatcagggc      720
tgtatggatt gtttaatctc ctataaattt aaggatggcc agagtgcgtt cgcgcgtcgc      780
ttctgggaag aagccgctgg cactggccgt ctgggctatg tctttggttg tccggtgcgt      840
tctgtggtga acgaacgcga cgcagtacgt gttaccgcac gtgacggtcg cgaattcgca      900
gcgaaacgtt tggtttgcac gattccgctg aacgtattga gtactattca gtttagccca      960
gcactgtcca cggaacgcat ctccgctatg caggcaggcc atgttaacat gtgcaccaaa     1020
gtgcatgcgg aagtcgataa tcaggatatg cgttcatgga cgggtatcgc ctatccgttc     1080
aacaaattat gctacgctat cggcgatggc acgaccccag cgggtaatac gcatctggtg     1140
tgcttcggga cagacgcgaa tcatatccag ccggacgagg acgtgcgcga aacgttgaaa     1200
gccgttggcc aactggcgcc tgggactttc ggtgtcaaac gtctggtctt ccacaactgg     1260
gtaaaggatg aatttgccaa aggcgcgtgg ttcttcagcc gcccaggcat ggtttcagag     1320
tgcctgcagg gtctgcgcga gaaacaccgt ggtgtcgtgt ttgcaaactc cgattgggcc     1380
ttaggttggc gtagttttat cgatggtgct atcgaggagg gcacccgcgc agcgcgtgtt     1440
gtactggagg aactggggac caagcgcgag gtgaaggccc gcctgtaatg a              1491

<210> SEQ ID NO 4
<211> LENGTH: 495
<212> TYPE: PRT
<213> ORGANISM: Artificial Sequence
<220> FEATURE:
<223> OTHER INFORMATION: variant monoamine oxidase

<400> SEQUENCE: 4

Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Thr Asn Ile Glu
            20                  25                  30

Asp Thr Asp Lys Asp Gly Pro Trp Asp Val Ile Val Ile Gly Gly Gly
        35                  40                  45

Tyr Cys Gly Leu Thr Ala Thr Arg Asp Leu Thr Val Ala Gly Phe Lys
    50                  55                  60

Thr Leu Leu Leu Glu Ala Arg Asp Arg Ile Gly Gly Arg Ser Trp Ser
65                  70                  75                  80

Ser Asn Ile Asp Gly Tyr Pro Tyr Glu Met Gly Gly Thr Trp Val His
                85                  90                  95

Trp His Gln Ser His Val Trp Arg Glu Ile Thr Arg Tyr Lys Met His
            100                 105                 110

Asn Ala Leu Ser Pro Ser Phe Asn Phe Ser Arg Gly Val Asn His Phe
        115                 120                 125

Gln Leu Arg Thr Asn Pro Thr Thr Ser Thr Tyr Met Thr His Glu Ala
    130                 135                 140

Glu Asp Glu Leu Leu Arg Ser Ala Leu His Lys Phe Thr Asn Val Asp
145                 150                 155                 160

Gly Thr Asn Gly Arg Thr Val Leu Pro Phe Pro His Asp Met Phe Tyr
                165                 170                 175

Val Pro Glu Phe Arg Lys Tyr Asp Glu Met Ser Tyr Ser Glu Arg Ile
            180                 185                 190
```

Asp Gln Ile Arg Asp Glu Leu Ser Leu Asn Glu Arg Ser Leu Glu
    195                 200                 205

Ala Phe Ile Leu Leu Cys Ser Gly Gly Thr Leu Glu Asn Ser Ser Phe
    210                 215                 220

Gly Glu Phe Leu His Trp Trp Ala Met Ser Gly Tyr Thr Tyr Gln Gly
225                 230                 235                 240

Cys Met Asp Cys Leu Ile Ser Tyr Lys Phe Lys Asp Gly Gln Ser Ala
                245                 250                 255

Phe Ala Arg Arg Phe Trp Glu Glu Ala Ala Gly Thr Gly Arg Leu Gly
            260                 265                 270

Tyr Val Phe Gly Cys Pro Val Arg Ser Val Val Asn Glu Arg Asp Ala
        275                 280                 285

Val Arg Val Thr Ala Arg Asp Gly Arg Glu Phe Ala Ala Lys Arg Leu
    290                 295                 300

Val Cys Thr Ile Pro Leu Asn Val Leu Ser Thr Ile Gln Phe Ser Pro
305                 310                 315                 320

Ala Leu Ser Thr Glu Arg Ile Ser Ala Met Gln Ala Gly His Val Asn
                325                 330                 335

Met Cys Thr Lys Val His Ala Glu Val Asp Asn Gln Asp Met Arg Ser
            340                 345                 350

Trp Thr Gly Ile Ala Tyr Pro Phe Asn Lys Leu Cys Tyr Ala Ile Gly
        355                 360                 365

Asp Gly Thr Thr Pro Ala Gly Asn Thr His Leu Val Cys Phe Gly Thr
    370                 375                 380

Asp Ala Asn His Ile Gln Pro Asp Glu Asp Val Arg Glu Thr Leu Lys
385                 390                 395                 400

Ala Val Gly Gln Leu Ala Pro Gly Thr Phe Gly Val Lys Arg Leu Val
                405                 410                 415

Phe His Asn Trp Val Lys Asp Glu Phe Ala Lys Gly Ala Trp Phe Phe
            420                 425                 430

Ser Arg Pro Gly Met Val Ser Glu Cys Leu Gln Gly Leu Arg Glu Lys
        435                 440                 445

His Arg Gly Val Val Phe Ala Asn Ser Asp Trp Ala Leu Gly Trp Arg
    450                 455                 460

Ser Phe Ile Asp Gly Ala Ile Glu Glu Gly Thr Arg Ala Ala Arg Val
465                 470                 475                 480

Val Leu Glu Glu Leu Gly Thr Lys Arg Glu Val Lys Ala Arg Leu
                485                 490                 495

<210> SEQ ID NO 5
<211> LENGTH: 1491
<212> TYPE: DNA
<213> ORGANISM: Artificial Sequence
<220> FEATURE:
<223> OTHER INFORMATION: variant monoamine oxidase

<400> SEQUENCE: 5
atgaccagcc gcgacggcta tcagtggacc ccggaaacgg gtctgaccca gggcgtaccg      60
tccctgggtg tcatttcgcc gccgactaac atcgaagata ccgataagga cgggccttgg     120
gatgtcattg tcattggggg cgggtattgt gggctgaccg caacccgtga tttaaccgtc     180
gcagggttca agacgctgct gctggaggcc cgtgatcgta ttggtggccg ctcctggagc     240
agtaatattg acggttaccc gtatgagatg ggtggcactt gggttcattg catcaatct      300 cacgtgtggc gtgaaatcac gcgttataaa atgcacaacg cgctgtctcc atcatttaac     360

```
ttttcacgtg gcgtgaatca cttccaactg cgtaccaatc cgaccaccag tacgtacatg    420
acgcacgaag cggaggatga actgctgcgt agcgcattgc ataaattcac caatgtcgac    480
ggcactaatg gccgtacagt gttgccgttc ccacatgata tgttttatgt gccggaattt    540
cgcaagtatg acgaaatgtc atattccgaa cgcattgacc agatccgcga cgaactgtct    600
ttgaacgaac gctctagttt agaggctttc attttattat gtagcggtgg caccctggaa    660
aactccagct tggtgaatt tctgcattgg tgggcaatgt cgggttacac gtatcagggc    720
tgtatggatt gtttaatctc ctataaattt aaggatggcc agagtgcgtt cgcgcgtcgc    780
ttctgggaag aagccgctgg cactggccgt ctgggctatg tctttggttg tccggtgcgt    840
tctgtggtga acgaacgcga cgcagtacgt gttaccgcac gtgacggtcg cgaattcgca    900
gcgaaacgtt tggtttgcac gattccgctg aacgtattga gttctgttca ttttagccca    960
ccactgtccc cgcaacgcat ggccgctgcg aacattggcc atgttaacca gtgcgtcaaa   1020
gtgcatgcgg aagtcagttg tccggatatg cgttcatggt cgggtatctc ctatccgttc   1080
aacaaattag cctacgctat cggcgatggc acgaccccag cgggtaatac gcatattgtg   1140
tgcttcgggg gggcccataa tcatatccag ccggaagagg acgtggaagc aacgaagatg   1200
gccgttgaaa acatgtcgcc tgggaatatg gatatcaaac gtctggtctt ccacaactgg   1260
tgcaaggatg aatttgccaa aggcgcgtgg ttcttcgccc ctccacagct gctgtcaaag   1320
agcctggatg aactgcgctg ccgtcacggt aatgtcctgt ttgcaaactc cgattgggcc   1380
gtaggttggc gtagttttat cgatggtgct atcgaggagg gcacccgcgc agcggttact   1440
gtaattgagg aactgcgtcc tgcgcctgcg gtgcgttccc acctgtaatg a            1491
```

<210> SEQ ID NO 6
<211> LENGTH: 495
<212> TYPE: PRT
<213> ORGANISM: Artificial Sequence
<220> FEATURE:
<223> OTHER INFORMATION: variant monoamine oxidase

<400> SEQUENCE: 6

```
Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Thr Asn Ile Glu
            20                  25                  30

Asp Thr Asp Lys Asp Gly Pro Trp Asp Val Ile Val Ile Gly Gly Gly
        35                  40                  45

Tyr Cys Gly Leu Thr Ala Thr Arg Asp Leu Thr Val Ala Gly Phe Lys
    50                  55                  60

Thr Leu Leu Leu Glu Ala Arg Asp Arg Ile Gly Gly Arg Ser Trp Ser
65                  70                  75                  80

Ser Asn Ile Asp Gly Tyr Pro Tyr Glu Met Gly Gly Thr Trp Val His
                85                  90                  95

Trp His Gln Ser His Val Trp Arg Glu Ile Thr Arg Tyr Lys Met His
            100                 105                 110

Asn Ala Leu Ser Pro Ser Phe Asn Phe Ser Arg Gly Val Asn His Phe
        115                 120                 125

Gln Leu Arg Thr Asn Pro Thr Thr Ser Thr Tyr Met Thr His Glu Ala
    130                 135                 140

Glu Asp Glu Leu Leu Arg Ser Ala Leu His Lys Phe Thr Asn Val Asp
145                 150                 155                 160

Gly Thr Asn Gly Arg Thr Val Leu Pro Phe Pro His Asp Met Phe Tyr
                165                 170                 175
```

Val Pro Glu Phe Arg Lys Tyr Asp Glu Met Ser Tyr Ser Glu Arg Ile
            180                 185                 190

Asp Gln Ile Arg Asp Glu Leu Ser Leu Asn Glu Arg Ser Ser Leu Glu
        195                 200                 205

Ala Phe Ile Leu Leu Cys Ser Gly Gly Thr Leu Glu Asn Ser Ser Phe
    210                 215                 220

Gly Glu Phe Leu His Trp Trp Ala Met Ser Gly Tyr Thr Tyr Gln Gly
225                 230                 235                 240

Cys Met Asp Cys Leu Ile Ser Tyr Lys Phe Lys Asp Gly Gln Ser Ala
                245                 250                 255

Phe Ala Arg Arg Phe Trp Glu Glu Ala Ala Gly Thr Gly Arg Leu Gly
            260                 265                 270

Tyr Val Phe Gly Cys Pro Val Arg Ser Val Val Asn Glu Arg Asp Ala
        275                 280                 285

Val Arg Val Thr Ala Arg Asp Gly Arg Glu Phe Ala Ala Lys Arg Leu
    290                 295                 300

Val Cys Thr Ile Pro Leu Asn Val Leu Ser Ser Val His Phe Ser Pro
305                 310                 315                 320

Pro Leu Ser Pro Gln Arg Met Ala Ala Ala Asn Ile Gly His Val Asn
                325                 330                 335

Gln Cys Val Lys Val His Ala Glu Val Ser Cys Pro Asp Met Arg Ser
            340                 345                 350

Trp Ser Gly Ile Ser Tyr Pro Phe Asn Lys Leu Ala Tyr Ala Ile Gly
        355                 360                 365

Asp Gly Thr Thr Pro Ala Gly Asn Thr His Ile Val Cys Phe Gly Gly
    370                 375                 380

Ala His Asn His Ile Gln Pro Glu Glu Asp Val Glu Ala Thr Lys Met
385                 390                 395                 400

Ala Val Glu Asn Met Ser Pro Gly Asn Met Asp Ile Lys Arg Leu Val
                405                 410                 415

Phe His Asn Trp Cys Lys Asp Glu Phe Ala Lys Gly Ala Trp Phe Phe
            420                 425                 430

Ala Pro Pro Gln Leu Leu Ser Lys Ser Leu Asp Glu Leu Arg Cys Arg
        435                 440                 445

His Gly Asn Val Leu Phe Ala Asn Ser Asp Trp Ala Val Gly Trp Arg
    450                 455                 460

Ser Phe Ile Asp Gly Ala Ile Glu Glu Gly Thr Arg Ala Ala Val Thr
465                 470                 475                 480

Val Ile Glu Glu Leu Arg Pro Ala Pro Ala Val Arg Ser His Leu
                485                 490                 495

<210> SEQ ID NO 7
<211> LENGTH: 1491
<212> TYPE: DNA
<213> ORGANISM: Artificial Sequence
<220> FEATURE:
<223> OTHER INFORMATION: variant monoamine oxidase

<400> SEQUENCE: 7
atgaccagcc gcgacggcta tcagtggacc ccggaaacgg gtctgaccca gggcgtaccg     60
tccctgggtg tcatttcgcc gccgactaac atcgaagata ccgataagga cgggccttgg    120
gatgtcattg tcattggggg cgggtattgt gggctgaccg caacccgtga tttaaccgtc    180
gcagggttca agacgctgct gctggaggcc cgtgatcgta ttggtggccg ctcctggagc    240
agtaatattg acggttaccc gtatgagatg ggtggcactt gggttcattg gcatcaatct    300

```
cacgtgtggc gtgaaatcac gcgttataaa atgcacaacg cgctgtctcc atcatttaac    360
ttttcacgtg gcgtgaatca cttccaactg cgtaccaatc cgaccaccag tacgtacatg    420
acgcacgaag cggaggatga actgctgcgt agcgcattgc ataaattcac caatgtcgac    480
ggcactaatg gccgtacagt gttgccgttc ccacatgata tgttttatgt gccggaattt    540
cgcaagtatg acgaaatgtc atattccgaa cgcattgacc agatccgcga cgaactgtct    600
ttgaacgaac gctctagttt agaggctttc attttattat gtagcggtgg cacctggaa     660
aactccagct ttggtgaatt ctgcattggt gggcaatgt cgggtacac gtatcagggc      720
tgtatggatt gtttaatctc ctataaattt aaggatggcc agagtgcgtt cgcgcgtcgc    780
ttctgggaag aagccgctgg cactggccgt ctgggctatg tctttggttg tccggtgcgt    840
tctgtggtga acgaacgcga cgcagtacgt gttaccgcac gtgacggtcg cgaattcgca    900
gcgaaacgtt tggttttgcac gattccgctg aacgtattga gtactattca gtttagccca   960
gcactgtcca cggaacgcat ctccgctatg caggcaggcc atgttaacat gtgcaccaaa   1020
gtgcatgcgg aagtcgataa tcaggatatg cgttcatgga cgggtatcgc ctatccgttc   1080
aacaaattat gctacgctat cggcgatggc acgaccccag cgggtaatac gcatctggtg   1140
tgcttcggga cagacgcgaa tcatatccag ccggacgagg acgtgcgcga aacgttgaaa   1200
gccgttggcc aactggcgcc tgggactttc ggtgtcaaac gtctggtctt ccacaactgg   1260
gtaaaggatg aatttgccaa aggcgcgtgg ttcttcagcc gcccaggcat ggtttcagag   1320
tgcctgcagg gtctgcgcga gaaacaccgt ggtgtcgtgt ttgcaaactc cgattgggcc   1380
ttaggttggc gtggttttat cgatggtgct atcgaggagg caccccgcgc agcgcgtgtt   1440
gtactggagg aactggggac caagcgcgag gtgaaggccc gcctgtaatg a             1491

<210> SEQ ID NO 8
<211> LENGTH: 495
<212> TYPE: PRT
<213> ORGANISM: Artificial Sequence
<220> FEATURE:
<223> OTHER INFORMATION: variant monoamine oxidase

<400> SEQUENCE: 8

Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Thr Asn Ile Glu
            20                  25                  30

Asp Thr Asp Lys Asp Gly Pro Trp Asp Val Ile Val Ile Gly Gly Gly
        35                  40                  45

Tyr Cys Gly Leu Thr Ala Thr Arg Asp Leu Thr Val Ala Gly Phe Lys
    50                  55                  60

Thr Leu Leu Leu Glu Ala Arg Asp Arg Ile Gly Gly Arg Ser Trp Ser
65                  70                  75                  80

Ser Asn Ile Asp Gly Tyr Pro Tyr Glu Met Gly Gly Thr Trp Val His
                85                  90                  95

Trp His Gln Ser His Val Trp Arg Glu Ile Thr Arg Tyr Lys Met His
            100                 105                 110

Asn Ala Leu Ser Pro Ser Phe Asn Phe Ser Arg Gly Val Asn His Phe
        115                 120                 125

Gln Leu Arg Thr Asn Pro Thr Thr Ser Thr Tyr Met Thr His Glu Ala
    130                 135                 140

Glu Asp Glu Leu Leu Arg Ser Ala Leu His Lys Phe Thr Asn Val Asp
145                 150                 155                 160
```

Gly Thr Asn Gly Arg Thr Val Leu Pro Phe Pro His Asp Met Phe Tyr
            165                 170                 175

Val Pro Glu Phe Arg Lys Tyr Asp Glu Met Ser Tyr Ser Glu Arg Ile
            180                 185                 190

Asp Gln Ile Arg Asp Glu Leu Ser Leu Asn Gly Arg Ser Ser Leu Glu
            195                 200                 205

Ala Phe Ile Leu Leu Cys Ser Gly Gly Thr Leu Glu Asn Ser Ser Phe
210                 215                 220

Gly Glu Phe Leu His Trp Trp Ala Met Ser Gly Tyr Thr Tyr Gln Gly
225                 230                 235                 240

Cys Met Asp Cys Leu Ile Ser Tyr Lys Phe Lys Asp Gly Gln Ser Ala
                245                 250                 255

Phe Ala Arg Arg Phe Trp Glu Glu Ala Gly Thr Gly Arg Leu Gly
            260                 265                 270

Tyr Val Phe Gly Cys Pro Val Arg Ser Val Val Asn Glu Arg Asp Ala
            275                 280                 285

Val Arg Val Thr Ala Arg Asp Gly Arg Glu Phe Ala Ala Lys Arg Leu
            290                 295                 300

Val Cys Thr Ile Pro Leu Asn Val Leu Ser Thr Ile Gln Phe Ser Pro
305                 310                 315                 320

Ala Leu Ser Thr Glu Arg Ile Ser Ala Met Gln Ala Gly His Val Asn
                325                 330                 335

Met Cys Thr Lys Val His Ala Glu Val Asp Asn Gln Asp Met Arg Ser
                340                 345                 350

Trp Thr Gly Ile Ala Tyr Pro Phe Asn Lys Leu Cys Tyr Ala Ile Gly
            355                 360                 365

Asp Gly Thr Thr Pro Ala Gly Asn Thr His Leu Val Cys Phe Gly Thr
            370                 375                 380

Asp Ala Asn His Ile Gln Pro Asp Glu Asp Val Arg Glu Thr Leu Lys
385                 390                 395                 400

Ala Val Gly Gln Leu Ala Pro Gly Thr Phe Gly Val Lys Arg Leu Val
                405                 410                 415

Phe His Asn Trp Val Lys Asp Glu Phe Ala Lys Gly Ala Trp Phe Phe
            420                 425                 430

Ser Arg Pro Gly Met Val Ser Glu Cys Leu Gln Gly Leu Arg Glu Lys
            435                 440                 445

His Arg Gly Val Val Phe Ala Asn Ser Asp Trp Ala Leu Gly Trp Arg
            450                 455                 460

Gly Phe Ile Asp Gly Ala Ile Glu Glu Gly Thr Arg Ala Ala Arg Val
465                 470                 475                 480

Val Leu Glu Glu Leu Gly Thr Lys Arg Glu Val Lys Ala Arg Leu
                485                 490                 495

<210> SEQ ID NO 9
<211> LENGTH: 1491
<212> TYPE: DNA
<213> ORGANISM: Artificial Sequence
<220> FEATURE:
<223> OTHER INFORMATION: variant monoamine oxidase

<400> SEQUENCE: 9
atgaccagcc gcgacggcta tcagtggacc ccggaaacgg gtctgaccca gggcgtaccg      60
tccctgggtg tcatttcgcc gccgactaac atcgaagata ccgataagga cgggccttgg     120
gatgtcattg tcattggggg cgggtattgt gggctgaccg caacccgtga tttaaccgtc     180

```
gcagggttca agacgctgct gctggaggcc cgtgatcgta ttggtggccg ctcctggagc    240
agtaatattg acgttaccc gtatgagatg ggtggcactt gggttcattg gcatcaatct    300
cacgtgtggc gtgaaatcac gcgttataaa atgcacaacg cgctgtctcc atcatttaac    360
ttttcacgtg gcgtgaatca cttccaactg cgtaccaatc cgaccaccag tacgtacatg    420
acgcacgaag cggaggatga actgctgcgt agcgcattgc ataaattcac caatgtcgac    480
ggcactaatg gccgtacagt gttgccgttc ccacatgata tgttttatgt gccggaattt    540
cgcaagtatg acgaaatgtc atattccgaa cgcattgacc agatccgcga cgaactgtct    600
ttgaacgaac gctctagttt agaggctttc attttattat gtagcggtgg cacccctgga    660
aactccagct ttggtgaatt tctgcattgg tgggcaatgt cgggttacac gtatcagggc    720
tgtatggatt gtttaatctc ctataaattt aaggatggcc agagtgcgtt cgcgcgtcgc    780
ttctgggaag aagccgctgg cactggccgt ctgggctatg tctttggttg tccggtgcgt    840
tctgtggtga acgaacgcga cgcagtacgt gttaccgcac gtgacggtcg cgaattcgca    900
gcgaaacgtt tggtttgcac gattccgctg aacgtattga gttctgttca ttttagccca    960
ccactgtccc cgcaacgcat ggccgctgcg aacattggcc atgttaacca gtgcgtcaaa   1020
gtgcatgcgg aagtcagttg tccggatatg cgttcatggt cgggtatctc ctatccgttc   1080
aacaaattag cctacgctat cggcgatggc acgaccccag cgggtaatac gcatattgtg   1140
tgcttcgggg gggcccataa tcatatccag ccggaagagg acgtggaagc aacgaagatg   1200
gccgttgaaa acatgtcgcc tgggaatatg gatatcaaac gtctggtctt ccacaactgg   1260
tgcaaggatg aatttgccaa aggcgcgtgg ttcttcgccc ctccacagct gctgtcaaag   1320
agcctggatg aactgcgctg ccgtcacggt aatgtcctgt ttgcaaactc cgattgggcc   1380
ttaggttggc gtggttttat cgatggtgct atcgaggagg gcacccgcgc agcggttact   1440
gtaattgagg aactgcgtcc tgcgcctgcg gtgcgttccc acctgtaatg a              1491
```

<210> SEQ ID NO 10
<211> LENGTH: 495
<212> TYPE: PRT
<213> ORGANISM: Artificial Sequence
<220> FEATURE:
<223> OTHER INFORMATION: variant monoamine oxidase

<400> SEQUENCE: 10

```
Met Thr Ser Arg Asp Gly Tyr Gln Trp Thr Pro Glu Thr Gly Leu Thr
  1               5                  10                  15

Gln Gly Val Pro Ser Leu Gly Val Ile Ser Pro Thr Asn Ile Glu
             20                  25                  30

Asp Thr Asp Lys Asp Gly Pro Trp Asp Val Ile Val Ile Gly Gly Gly
         35                  40                  45

Tyr Cys Gly Leu Thr Ala Thr Arg Asp Leu Thr Val Ala Gly Phe Lys
     50                  55                  60

Thr Leu Leu Leu Glu Ala Arg Asp Arg Ile Gly Gly Arg Ser Trp Ser
 65                  70                  75                  80

Ser Asn Ile Asp Gly Tyr Pro Tyr Glu Met Gly Thr Trp Val His
                 85                  90                  95

Trp His Gln Ser His Val Trp Arg Glu Ile Thr Arg Tyr Lys Met His
                100                 105                 110

Asn Ala Leu Ser Pro Ser Phe Asn Phe Ser Arg Gly Val Asn His Phe
            115                 120                 125

Gln Leu Arg Thr Asn Pro Thr Thr Ser Thr Tyr Met Thr His Glu Ala
        130                 135                 140
```

```
Glu Asp Glu Leu Leu Arg Ser Ala Leu His Lys Phe Thr Asn Val Asp
145                 150                 155                 160

Gly Thr Asn Gly Arg Thr Val Leu Pro Phe Pro His Asp Met Phe Tyr
                165                 170                 175

Val Pro Glu Phe Arg Lys Tyr Asp Glu Met Ser Tyr Ser Glu Arg Ile
            180                 185                 190

Asp Gln Ile Arg Asp Glu Leu Ser Leu Asn Glu Arg Ser Ser Leu Glu
        195                 200                 205

Ala Phe Ile Leu Leu Cys Ser Gly Gly Thr Leu Glu Asn Ser Ser Phe
    210                 215                 220

Gly Glu Phe Leu His Trp Trp Ala Met Ser Gly Tyr Thr Tyr Gln Gly
225                 230                 235                 240

Cys Met Asp Cys Leu Ile Ser Tyr Lys Phe Lys Asp Gly Gln Ser Ala
                245                 250                 255

Phe Ala Arg Arg Phe Trp Glu Glu Ala Ala Gly Thr Gly Arg Leu Gly
            260                 265                 270

Tyr Val Phe Gly Cys Pro Val Arg Ser Val Val Asn Glu Arg Asp Ala
        275                 280                 285

Val Arg Val Thr Ala Arg Asp Gly Arg Glu Phe Ala Ala Lys Arg Leu
    290                 295                 300

Val Cys Thr Ile Pro Leu Asn Val Leu Ser Ser Val His Phe Ser Pro
305                 310                 315                 320

Pro Leu Ser Pro Gln Arg Met Ala Ala Ala Asn Ile Gly His Val Asn
                325                 330                 335

Gln Cys Val Lys Val His Ala Glu Val Ser Cys Pro Asp Met Arg Ser
            340                 345                 350

Trp Ser Gly Ile Ser Tyr Pro Phe Asn Lys Leu Ala Tyr Ala Ile Gly
        355                 360                 365

Asp Gly Thr Thr Pro Ala Gly Asn Thr His Ile Val Cys Phe Gly Gly
    370                 375                 380

Ala His Asn His Ile Gln Pro Glu Glu Asp Val Glu Ala Thr Lys Met
385                 390                 395                 400

Ala Val Glu Asn Met Ser Pro Gly Asn Met Asp Ile Lys Arg Leu Val
                405                 410                 415

Phe His Asn Trp Cys Lys Asp Gly Phe Ala Lys Gly Ala Trp Phe Phe
            420                 425                 430

Ala Pro Pro Gln Leu Leu Ser Lys Ser Leu Asp Glu Leu Arg Cys Arg
        435                 440                 445

His Gly Asn Val Leu Phe Ala Asn Ser Asp Trp Ala Leu Gly Trp Arg
    450                 455                 460

Gly Phe Ile Asp Gly Ala Ile Glu Glu Gly Thr Arg Ala Ala Val Thr
465                 470                 475                 480

Val Ile Glu Glu Leu Arg Pro Ala Pro Ala Val Arg Ser His Leu
                485                 490                 495

<210> SEQ ID NO 11
<211> LENGTH: 1485
<212> TYPE: DNA
<213> ORGANISM: Artificial Sequence
<220> FEATURE:
<223> OTHER INFORMATION: variant monoamine oxidase

<400> SEQUENCE: 11
atgaccagcc gcgacggcta tcagtggacc ccggaaacgg gtctgaccca gggcgtaccg      60
tccctgggtg tcatttcgcc gccgactaac atcgaagata ccgataagga cgggccttgg     120
```

```
gatgtcattg tcattggggg cgggtattgt gggctgaccg caacccgtga tttaaccgtc    180
gcagggttca agacgctgct gctggaggcc cgtgatcgta ttggtggccg ctcctggagc    240
agtaatattg acggttaccc gtatgagatg ggtggcactt gggttcattg gcatcaatct    300
cacgtgtggc gtgaaatcac gcgttataaa atgcacaacg cgctgtctcc atcatttaac    360
ttttcacgtg gcgtgaatca cttccaactg cgtaccaatc cgaccaccag tacgtacatg    420
acgcacgaag cggaggatga actgctgcgt agcgcattgc ataaattcac caatgtcgac    480
ggcactaatg gccgtacagt gttgccgttc ccacatgata tgttttatgt gccggaattt    540
cgcaagtatg acgaaatgtc atattccgaa cgcattgacc agatccgcga cgaactgtct    600
ttgaacgaac gctctagttt agaggctttc attttattat gtagcggtgg caccctggaa    660
aactccagct ttggtgaatt tctgcattgg tgggcaatgt cgggttacac gtatcagggc    720
tgtatggatt gtttaatctc ctataaattt aaggatggcc agagtgcgtt cgcgcgtcgc    780
ttctgggaag aagccgctgg cactggccgt ctgggctatg tctttggttg tccggtgcgt    840
tctgtggtga acgaacgcga cgcagtacgt gttaccgcac gtgacggtcg cgaattcgca    900
gcgaaacgtt tggtttgcac gattccgctg aacgtattga gttctgttca ttttagccca    960
ccactgtccc cgcaacgcat ggccgctgcg aacattggcc atgttaacca gtgcgtcaaa   1020
gtgcatgcgg aagtcagttg tccggatatg cgttcatggt cgggtatctc ctatccgttc   1080
aacaaattag cctacgctat cggcgatggc acgaccccag cgggtaatac gcatattgtg   1140
tgccttgggg gggcccataa tcatatccag ccggaagagg acgtggaagc aacgaagatg   1200
gccgttgaaa acatgtcgcc tgggaatatg gatatcaaac gtctggtctt ccacaactgg   1260
tgcaaggatg aatttgccaa aggcgcgtgg ttcttcgccc ctccacagct gctgtcaaag   1320
agcctggatg aactgcgctg ccgtcacggt aatgtcctgt ttgcaaactc cgattgggcc   1380
ttaggttggc gtggttttat cgatggtgct atcgaggagg gcacccgcgc agcggttact   1440
gtaattgagg aactgcgtcc tgcgcctgcg gtgcgttccc acctg                    1485
```

<210> SEQ ID NO 12
<211> LENGTH: 495
<212> TYPE: PRT
<213> ORGANISM: Artificial Sequence
<220> FEATURE:
<223> OTHER INFORMATION: variant monoamine oxidase

<400> SEQUENCE: 12

```
Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Pro Thr Asn Ile Glu
            20                  25                  30

Asp Thr Asp Lys Asp Gly Pro Trp Asp Val Ile Val Ile Gly Gly Gly
        35                  40                  45

Tyr Cys Gly Leu Thr Ala Thr Arg Asp Leu Thr Val Ala Gly Phe Lys
    50                  55                  60

Thr Leu Leu Leu Glu Ala Arg Asp Arg Ile Gly Gly Arg Ser Trp Ser
65                  70                  75                  80

Ser Asn Ile Asp Gly Tyr Pro Tyr Glu Met Gly Gly Thr Trp Val His
                85                  90                  95

Trp His Gln Ser His Val Trp Arg Glu Ile Thr Arg Tyr Lys Met His
            100                 105                 110

Asn Ala Leu Ser Pro Ser Phe Asn Phe Ser Arg Gly Val Asn His Phe
        115                 120                 125
```

```
Gln Leu Arg Thr Asn Pro Thr Thr Ser Thr Tyr Met Thr His Glu Ala
    130                 135                 140

Glu Asp Glu Leu Leu Arg Ser Ala Leu His Lys Phe Thr Asn Val Asp
145                 150                 155                 160

Gly Thr Asn Gly Arg Thr Val Leu Pro Phe Pro His Asp Met Phe Tyr
                165                 170                 175

Val Pro Glu Phe Arg Lys Tyr Asp Glu Met Ser Tyr Ser Glu Arg Ile
            180                 185                 190

Asp Gln Ile Arg Asp Glu Leu Ser Leu Asn Glu Arg Ser Ser Leu Glu
        195                 200                 205

Ala Phe Ile Leu Leu Cys Ser Gly Gly Thr Leu Glu Asn Ser Ser Phe
210                 215                 220

Gly Glu Phe Leu His Trp Trp Ala Met Ser Gly Tyr Thr Tyr Gln Gly
225                 230                 235                 240

Cys Met Asp Cys Leu Ile Ser Tyr Lys Phe Lys Asp Gly Gln Ser Ala
                245                 250                 255

Phe Ala Arg Arg Phe Trp Glu Glu Ala Ala Gly Thr Gly Arg Leu Gly
            260                 265                 270

Tyr Val Phe Gly Cys Pro Val Arg Ser Val Val Asn Glu Arg Asp Ala
        275                 280                 285

Val Arg Val Thr Ala Arg Asp Gly Arg Glu Phe Ala Ala Lys Arg Leu
290                 295                 300

Val Cys Thr Ile Pro Leu Asn Val Leu Ser Ser Val His Phe Ser Pro
305                 310                 315                 320

Pro Leu Ser Pro Gln Arg Met Ala Ala Ala Asn Ile Gly His Val Asn
                325                 330                 335

Gln Cys Val Lys Val His Ala Glu Val Ser Cys Pro Asp Met Arg Ser
            340                 345                 350

Trp Ser Gly Ile Ser Tyr Pro Phe Asn Lys Leu Ala Tyr Ala Ile Gly
        355                 360                 365

Asp Gly Thr Thr Pro Ala Gly Asn Thr His Ile Val Cys Leu Gly Gly
370                 375                 380

Ala His Asn His Ile Gln Pro Glu Glu Asp Val Glu Ala Thr Lys Met
385                 390                 395                 400

Ala Val Glu Asn Met Ser Pro Gly Asn Met Asp Ile Lys Arg Leu Val
                405                 410                 415

Phe His Asn Trp Cys Lys Asp Glu Phe Ala Lys Gly Ala Trp Phe Phe
            420                 425                 430

Ala Pro Pro Gln Leu Leu Ser Lys Ser Leu Asp Glu Leu Arg Cys Arg
        435                 440                 445

His Gly Asn Val Leu Phe Ala Asn Ser Asp Trp Ala Leu Gly Trp Arg
450                 455                 460

Gly Phe Ile Asp Gly Ala Ile Glu Glu Gly Thr Arg Ala Ala Val Thr
465                 470                 475                 480

Val Ile Glu Glu Leu Arg Pro Ala Pro Ala Val Arg Ser His Leu
                485                 490                 495

<210> SEQ ID NO 13
<211> LENGTH: 1491
<212> TYPE: DNA
<213> ORGANISM: Artificial Sequence
<220> FEATURE:
<223> OTHER INFORMATION: variant monoamine oxidase

<400> SEQUENCE: 13
```

```
atgaccagcc gcgacggcta tcagtggacc ccggaaacgg gtctgaccca gggcgtaccg    60
tccctgggtg tcatttcgcc gccgactaac atcgaagata ccgataagga cgggccttgg   120
gatgtcattg tcattggggg cgggtattgt gggctgaccg caacccgtga tttaaccgtc   180
gcagggttca agacgctgct gctggaggcc cgtgatcgta ttggtggccg ctcctggagc   240
agtaatattg acggttaccc gtatgagatg ggtggcactt gggttcattg gcatcaatct   300
cacgtgtggc gtgaaatcac gcgttataaa atgcacaacg cgctgtctcc atcatttaac   360
ttttcacgtg gcgtgaatca cttccaactg cgtaccaatc cgaccaccag tacgtacatg   420
acgcacgaag cggaggatga actgctgcgt agcgcattgc ataaattcac caatgtcgac   480
ggcactaatg ccgtacagt gttgccgttc ccacatgata tgttttatgt gccggaattt   540
cgcaagtatg acgaaatgtc atattccgaa cgcattgacc agatccgcga cgaactgtct   600
ttgaacgaac gctctagttt agaggctttc attttattat gtagcggtgg caccctggaa   660
aactccagct ttggtgaatt tctgcattgg tgggcaatgt cgggttacac gtatcagggc   720
tgtatggatt gtttaatctc ctataaattt aaggatggcc agagtgcgtt cgcgcgtcgc   780
ttctgggaag aagccgctgg cactggccgt ctgggctatg tctttggttg tccggtgcgt   840
tctgtggtga cgaacgcga cgcagtacgt gttaccgcac gtgacggtcg cgaattcgca   900
gcgaaacgtt tggtttgcac gattccgctg aacgtattga gttctgttca ttttagccca   960
ccactgtccc cgcaacgcat ggccgctgcg aacattggcc atgttaacca gtgcgtcaaa  1020
gtgcatgcgg aagtcagttg tccggatatg cgttcatggt cgggtatctc ctatccgttc  1080
aacaaattag cctgggctat cggcgatggc acgaccccag cgggtaatac gcatattgtg  1140
tgcttcgggg gggcccataa tcatatccag ccggaagagg acgtggaagc aacgaagatg  1200
gccgttgaaa acatgtcgcc tgggaatatg gatatcaaac gtctggtctt ccacaactgg  1260
tgcaaggatg aatttgccaa aggcgcgtgg ttcttcgccc ctccacagct gctgtcaaag  1320
agcctggatg aactgcgctg ccgtcacggt aatgtcctgt ttgcaaactc cgattgggcc  1380
ttaggttggc gtggttttat cgatggtgct atcgaggagg gcacccgcgc agcggttact  1440
gtaattgagg aactgcgtcc tgcgcctgcg gtgcgttccc acctgtaatg a            1491
```

<210> SEQ ID NO 14
<211> LENGTH: 495
<212> TYPE: PRT
<213> ORGANISM: Artificial Sequence
<220> FEATURE:
<223> OTHER INFORMATION: variant monoamine oxidase

<400> SEQUENCE: 14

```
Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Pro Thr Asn Ile Glu
            20                  25                  30

Asp Thr Asp Lys Asp Gly Pro Trp Asp Val Ile Val Ile Gly Gly Gly
        35                  40                  45

Tyr Cys Gly Leu Thr Ala Thr Arg Asp Leu Thr Val Ala Gly Phe Lys
    50                  55                  60

Thr Leu Leu Leu Glu Ala Arg Asp Arg Ile Gly Gly Arg Ser Trp Ser
65                  70                  75                  80

Ser Asn Ile Asp Gly Tyr Pro Tyr Glu Met Gly Gly Thr Trp Val His
                85                  90                  95

Trp His Gln Ser His Val Trp Arg Glu Ile Thr Arg Tyr Lys Met His
            100                 105                 110
```

Asn Ala Leu Ser Pro Ser Phe Asn Phe Ser Arg Gly Val Asn His Phe
    115                 120                 125

Gln Leu Arg Thr Asn Pro Thr Thr Ser Thr Tyr Met Thr His Glu Ala
        130                 135                 140

Glu Asp Glu Leu Leu Arg Ser Ala Leu His Lys Phe Thr Asn Val Asp
145                 150                 155                 160

Gly Thr Asn Gly Arg Thr Val Leu Pro Phe Pro His Asp Met Phe Tyr
                165                 170                 175

Val Pro Glu Phe Arg Lys Tyr Asp Glu Met Ser Tyr Ser Glu Arg Ile
            180                 185                 190

Asp Gln Ile Arg Asp Glu Leu Ser Leu Asn Glu Arg Ser Ser Leu Glu
        195                 200                 205

Ala Phe Ile Leu Leu Cys Ser Gly Gly Thr Leu Glu Asn Ser Ser Phe
    210                 215                 220

Gly Glu Phe Leu His Trp Trp Ala Met Ser Gly Tyr Thr Tyr Gln Gly
225                 230                 235                 240

Cys Met Asp Cys Leu Ile Ser Tyr Lys Phe Lys Asp Gly Gln Ser Ala
                245                 250                 255

Phe Ala Arg Arg Phe Trp Glu Glu Ala Ala Gly Thr Gly Arg Leu Gly
            260                 265                 270

Tyr Val Phe Gly Cys Pro Val Arg Ser Val Val Asn Glu Arg Asp Ala
        275                 280                 285

Val Arg Val Thr Ala Arg Asp Gly Arg Glu Phe Ala Ala Lys Arg Leu
    290                 295                 300

Val Cys Thr Ile Pro Leu Asn Val Leu Ser Ser Val His Phe Ser Pro
305                 310                 315                 320

Pro Leu Ser Pro Gln Arg Met Ala Ala Ala Asn Ile Gly His Val Asn
                325                 330                 335

Gln Cys Val Lys Val His Ala Glu Val Ser Cys Pro Asp Met Arg Ser
            340                 345                 350

Trp Ser Gly Ile Ser Tyr Pro Phe Asn Lys Leu Ala Trp Ala Ile Gly
        355                 360                 365

Asp Gly Thr Thr Pro Ala Gly Asn Thr His Ile Val Cys Phe Gly Gly
    370                 375                 380

Ala His Asn His Ile Gln Pro Glu Glu Asp Val Glu Ala Thr Lys Met
385                 390                 395                 400

Ala Val Glu Asn Met Ser Pro Gly Asn Met Asp Ile Lys Arg Leu Val
                405                 410                 415

Phe His Asn Trp Cys Lys Asp Glu Phe Ala Lys Gly Ala Trp Phe Phe
            420                 425                 430

Ala Pro Pro Gln Leu Leu Ser Lys Ser Leu Asp Glu Leu Arg Cys Arg
        435                 440                 445

His Gly Asn Val Leu Phe Ala Asn Ser Asp Trp Ala Leu Gly Trp Arg
    450                 455                 460

Gly Phe Ile Asp Gly Ala Ile Glu Gly Thr Arg Ala Ala Val Thr
465                 470                 475                 480

Val Ile Glu Glu Leu Arg Pro Ala Pro Ala Val Arg Ser His Leu
                485                 490                 495

<210> SEQ ID NO 15
<211> LENGTH: 1491
<212> TYPE: DNA
<213> ORGANISM: Artificial Sequence
<220> FEATURE:
<223> OTHER INFORMATION: variant monoamine oxidase

<400> SEQUENCE: 15

```
atgaccagcc gcgacggcta tcagtggacc ccggaaacgg gtctgaccca gggcgtaccg      60
tccctgggtg tcatttcgcc gccgactaac atcgaagata ccgataagga cgggccttgg     120
gatgtcattg tcattggggg cgggtattgt gggctgaccg caacccgtga tttaaccgtc     180
gcagggttca agacgctgct gctggaggcc cgtgatcgta ttggtggccg ctcctggagc     240
agtaatattg acggttaccc gtatgagatg ggtggcactt gggttcattg gcatgaatct     300
cacgtgtggc gtgaaatcac gcgttataaa atgcacaacg cgctgtctcc atcatttaac     360
ttttcacgtg gcgtgaatca cttccaactg cgtaccaatc cgaccaccag tacgtacatg     420
acgcacgaag cggaggatga actgctgcgt agcgcattgc ataaaattca caatgtcgac     480
ggcactaatg gccgtacagt gttgccgttc ccacatgata tgttttatgt gccggaattt     540
cgcaagtatg acgaaatgtc atattccgaa cgcattgacc agatccgcga cgaactgtct     600
ttgaacgaac gctctagttt agaggctttc attttattat gtagcggtgg cacccctggaa    660
aactccagct ttggtgaatt tctgcattgg tgggcaatgt cgggttacac gtatcagggc     720
tgtatggatt gtttaatctc ctataaattt aaggatggcc agagtgcgtt cgcgcgtcgc     780
ttctgggaag aagccgctgg cactggccgt ctgggctatg tctttggttg tccggtgcgt     840
tctgtggtga cgaacgcga cgcagtacgt gttaccgcac gtgacggtcg cgaattcgca     900
gcgaaacgtt tggtttgcac gattccgctg aacgtattga gttctgttca ttttagccca     960
ccactgtccc cgcaacgcat ggccgctgcg aacattggcc atgttaacca gtgcgtcaaa    1020
gtgcatgcgg aagtcagttg tccggatatg cgttcatggt cgggtatctc ctatccgttc    1080
aacaaattag cctgggctat cggcgatggc acgaccccag cgggtaatac gcatattgtg    1140
tgcttcgggg gcgctcataa tcatatccag ccggaagagg acgtggaagc aacgaagatg    1200
gccgttgaaa acatgtcgcc tgggaatatg gatatcaaac gtctggtctt ccacaactgg    1260
tgcaaggatg aatttgccaa aggcgcttgg ttcttcgccc ctccacagct gctgtcaaag    1320
agcctggatg aactgcgctg ccgtcacggt aatgtcctgt ttgcaaactc cgattgggcc    1380
ttaggttggc gtggttttat tgatggtgct atcgaggagg gcacccgcgc agcggttact    1440
gtaattgagg aactgcgtcc tgcgcctgcg gtgcgttccc acctgtaatg a              1491
```

<210> SEQ ID NO 16
<211> LENGTH: 495
<212> TYPE: PRT
<213> ORGANISM: Artificial Sequence
<220> FEATURE:
<223> OTHER INFORMATION: variant monoamine oxidase

<400> SEQUENCE: 16

```
Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Pro Thr Asn Ile Glu
            20                  25                  30

Asp Thr Asp Lys Asp Gly Pro Trp Asp Val Ile Val Ile Gly Gly Gly
        35                  40                  45

Tyr Cys Gly Leu Thr Ala Thr Arg Asp Leu Thr Val Ala Gly Phe Lys
    50                  55                  60

Thr Leu Leu Leu Glu Ala Arg Asp Arg Ile Gly Gly Arg Ser Trp Ser
65                  70                  75                  80

Ser Asn Ile Asp Gly Tyr Pro Tyr Glu Met Gly Gly Thr Trp Val His
                85                  90                  95
```

Trp His Glu Ser His Val Trp Arg Glu Ile Thr Arg Tyr Lys Met His
                100                 105                 110
Asn Ala Leu Ser Pro Ser Phe Asn Phe Ser Arg Gly Val Asn His Phe
            115                 120                 125
Gln Leu Arg Thr Asn Pro Thr Thr Ser Thr Tyr Met Thr His Glu Ala
        130                 135                 140
Glu Asp Glu Leu Leu Arg Ser Ala Leu His Lys Phe Thr Asn Val Asp
145                 150                 155                 160
Gly Thr Asn Gly Arg Thr Val Leu Pro Phe Pro His Asp Met Phe Tyr
                165                 170                 175
Val Pro Glu Phe Arg Lys Tyr Asp Glu Met Ser Tyr Ser Glu Arg Ile
            180                 185                 190
Asp Gln Ile Arg Asp Glu Leu Ser Leu Asn Glu Arg Ser Ser Leu Glu
        195                 200                 205
Ala Phe Ile Leu Leu Cys Ser Gly Gly Thr Leu Glu Asn Ser Ser Phe
210                 215                 220
Gly Glu Phe Leu His Trp Trp Ala Met Ser Gly Tyr Thr Tyr Gln Gly
225                 230                 235                 240
Cys Met Asp Cys Leu Ile Ser Tyr Lys Phe Lys Asp Gly Gln Ser Ala
                245                 250                 255
Phe Ala Arg Arg Phe Trp Glu Glu Ala Ala Gly Thr Gly Arg Leu Gly
            260                 265                 270
Tyr Val Phe Gly Cys Pro Val Arg Ser Val Val Asn Glu Arg Asp Ala
        275                 280                 285
Val Arg Val Thr Ala Arg Asp Gly Arg Glu Phe Ala Ala Lys Arg Leu
290                 295                 300
Val Cys Thr Ile Pro Leu Asn Val Leu Ser Ser Val His Phe Ser Pro
305                 310                 315                 320
Pro Leu Ser Pro Gln Arg Met Ala Ala Ala Asn Ile Gly His Val Asn
                325                 330                 335
Gln Cys Val Lys Val His Ala Glu Val Ser Cys Pro Asp Met Arg Ser
            340                 345                 350
Trp Ser Gly Ile Ser Tyr Pro Phe Asn Lys Leu Ala Trp Ala Ile Gly
        355                 360                 365
Asp Gly Thr Thr Pro Ala Gly Asn Thr His Ile Val Cys Phe Gly Gly
        370                 375                 380
Ala His Asn His Ile Gln Pro Glu Glu Asp Val Glu Ala Thr Lys Met
385                 390                 395                 400
Ala Val Glu Asn Met Ser Pro Gly Asn Met Asp Ile Lys Arg Leu Val
                405                 410                 415
Phe His Asn Trp Cys Lys Asp Glu Phe Ala Lys Gly Ala Trp Phe Phe
            420                 425                 430
Ala Pro Pro Gln Leu Leu Ser Lys Ser Leu Asp Glu Leu Arg Cys Arg
        435                 440                 445
His Gly Asn Val Leu Phe Ala Asn Ser Asp Trp Ala Leu Gly Trp Arg
        450                 455                 460
Gly Phe Ile Asp Gly Ala Ile Glu Glu Gly Thr Arg Ala Ala Val Thr
465                 470                 475                 480
Val Ile Glu Glu Leu Arg Pro Ala Pro Ala Val Arg Ser His Leu
                485                 490                 495

<210> SEQ ID NO 17
<211> LENGTH: 1491
<212> TYPE: DNA

<213> ORGANISM: Artificial Sequence
<220> FEATURE:
<223> OTHER INFORMATION: variant monoamine oxidase

<400> SEQUENCE: 17

```
atgaccagcc gcgacggcta tcagtggacc ccggaaacgg gtctgaccca gggcgtaccg      60
tccctgggtg tcatttcgcc gccgactaac atcgaagata ccgataagga cgggccttgg     120
gatgtcattg tcattggggg cgggtattgt gggctgaccg caacccgtga tttaaccgtc     180
gcagggttca agacgctgct gctggaggcc cgtgatcgta ttggtggccg ctcctggagc     240
agtaatattg acggttaccc gtatgagatg ggtggcactt gggttcattg gcatgaatct     300
cacgtgtggc gtgaaatcac gcgttataaa atgcacaacg cgctgtctcc atcatttaac     360
ttttcacgtg gcgtgaatca cttccaactg cgtaccaatc cgcagaccag tacgtacatg     420
acgcacgaag cggaggatga actgctgcgt agcgcattgc ataaattcac caatgtcgac     480
ggcactaatg ccgtacagt gttgccgttc ccacatgata tgttttatgt gccggaattt     540
cgcaagtatg acgaaatgtc atattccgaa cgcattgacc agatccgcga cgaactgtct     600
ttgaacgaac gctctagttt agaggctttc attttattat gtagcggtgg caccctggaa     660
aactccagct ttggtgaatt tctgcattgg tgggcaatgt cgggttacac gtatcagggc     720
tgtatggatt gtttaatctc ctataaattt aaggatggcc agagtgcgtt cgcgcgtcgc     780
ttctgggaag aagccgctgg cactggccgt ctgggctatg tctttggttg tccggtgcgt     840
tctgtggtga cgaacgcga cgcagtacgt gttaccgcac gtgacggtcg cgaattcgca     900
gcgaaacgtt tggtttgcac gattccgctg aacgtattga gttctgttca ttttagccca     960
ccactgtccc cgcaacgcat ggccgctgcg aacattggcc atgttaacca gtgcgtcaaa    1020
gtgcatgcgg aagtcagttg tccggatatg cgttcatggt cgggtatctc ctatccgttc    1080
aacaaattag cctgggctat cggcgatggc acgaccccag cgggtaatac gcatattgtg    1140
tgcttcgggg gcgctcataa tcatatccag ccggaagagg acgtggaagc aacgaagatg    1200
gccgttgaaa acatgtcgcc tgggaatatg gatatcaaac gtctggtctt ccacaactgg    1260
tgcaaggatg aatttgccaa aggcgcttgg ttcttcgccc ctccacagct gctgtcaaag    1320
agcctggatg aactgcgctg ccgtcacggt aatgtcctgt ttgcaaactc cgattgggcc    1380
ttaggttggc gtggttttat tgatggtgct atcgaggagg gcacccgcgc agcggttact    1440
gtaattgagg aactgcgtcc tgcgcctgcg gtgcgttccc acctgtaatg a             1491
```

<210> SEQ ID NO 18
<211> LENGTH: 495
<212> TYPE: PRT
<213> ORGANISM: Artificial Sequence
<220> FEATURE:
<223> OTHER INFORMATION: variant monoamine oxidase

<400> SEQUENCE: 18

```
Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Thr Asn Ile Glu
            20                  25                  30

Asp Thr Asp Lys Asp Gly Pro Trp Asp Val Ile Val Ile Gly Gly Gly
        35                  40                  45

Tyr Cys Gly Leu Thr Ala Thr Arg Asp Leu Thr Val Ala Gly Phe Lys
    50                  55                  60

Thr Leu Leu Leu Glu Ala Arg Asp Arg Ile Gly Gly Arg Ser Trp Ser
65                  70                  75                  80
```

-continued

```
Ser Asn Ile Asp Gly Tyr Pro Tyr Glu Met Gly Gly Thr Trp Val His
                85                  90                  95
Trp His Glu Ser His Val Trp Arg Glu Ile Thr Arg Tyr Lys Met His
            100                 105                 110
Asn Ala Leu Ser Pro Ser Phe Asn Phe Ser Arg Gly Val Asn His Phe
        115                 120                 125
Gln Leu Arg Thr Asn Pro Gln Thr Ser Thr Tyr Met Thr His Glu Ala
    130                 135                 140
Glu Asp Glu Leu Leu Arg Ser Ala Leu His Lys Phe Thr Asn Val Asp
145                 150                 155                 160
Gly Thr Asn Gly Arg Thr Val Leu Pro Phe Pro His Asp Met Phe Tyr
                165                 170                 175
Val Pro Glu Phe Arg Lys Tyr Asp Glu Met Ser Tyr Ser Glu Arg Ile
            180                 185                 190
Asp Gln Ile Arg Asp Glu Leu Ser Leu Asn Glu Arg Ser Ser Leu Glu
        195                 200                 205
Ala Phe Ile Leu Leu Cys Ser Gly Gly Thr Leu Glu Asn Ser Ser Phe
    210                 215                 220
Gly Glu Phe Leu His Trp Trp Ala Met Ser Gly Tyr Thr Tyr Gln Gly
225                 230                 235                 240
Cys Met Asp Cys Leu Ile Ser Tyr Lys Phe Lys Asp Gly Gln Ser Ala
                245                 250                 255
Phe Ala Arg Arg Phe Trp Glu Glu Ala Gly Thr Gly Arg Leu Gly
            260                 265                 270
Tyr Val Phe Gly Cys Pro Val Arg Ser Val Val Asn Glu Arg Asp Ala
        275                 280                 285
Val Arg Val Thr Ala Arg Asp Gly Arg Glu Phe Ala Ala Lys Arg Leu
    290                 295                 300
Val Cys Thr Ile Pro Leu Asn Val Leu Ser Ser Val His Phe Ser Pro
305                 310                 315                 320
Pro Leu Ser Pro Gln Arg Met Ala Ala Ala Asn Ile Gly His Val Asn
                325                 330                 335
Gln Cys Val Lys Val His Ala Glu Val Ser Cys Pro Asp Met Arg Ser
            340                 345                 350
Trp Ser Gly Ile Ser Tyr Pro Phe Asn Lys Leu Ala Trp Ala Ile Gly
        355                 360                 365
Asp Gly Thr Thr Pro Ala Gly Asn Thr His Ile Val Cys Phe Gly Gly
    370                 375                 380
Ala His Asn His Ile Gln Pro Glu Glu Asp Val Glu Ala Thr Lys Met
385                 390                 395                 400
Ala Val Glu Asn Met Ser Pro Gly Asn Met Asp Ile Lys Arg Leu Val
                405                 410                 415
Phe His Asn Trp Cys Lys Asp Glu Phe Ala Lys Gly Ala Trp Phe Phe
            420                 425                 430
Ala Pro Pro Gln Leu Leu Ser Lys Ser Leu Asp Glu Leu Arg Cys Arg
        435                 440                 445
His Gly Asn Val Leu Phe Ala Asn Ser Asp Trp Ala Leu Gly Trp Arg
    450                 455                 460
Gly Phe Ile Asp Gly Ala Ile Glu Glu Gly Thr Arg Ala Ala Val Thr
465                 470                 475                 480
Val Ile Glu Glu Leu Arg Pro Ala Pro Ala Val Arg Ser His Leu
                485                 490                 495
```

```
<210> SEQ ID NO 19
<211> LENGTH: 1491
<212> TYPE: DNA
<213> ORGANISM: Artificial Sequence
<220> FEATURE:
<223> OTHER INFORMATION: variant monoamine oxidase

<400> SEQUENCE: 19
atgaccagcc gcgacggtta tcagtggacc ccggaaacgg gtctgaccca gggcgtaccg      60
tccctgggtg tcatttcgcc gccgactaac atcgaagata ccgataagga cgggccttgg     120
gatgtcattg tcattggggg cgggtattgt gggctgaccg caacccgtga tttaaccgtc     180
gcagggttca agacgctgct gctggaggcc cgtgatcgta ttggtggccg ctcctggagc     240
agtaatattg acggttaccc gtatgagatg ggtggcactt gggttcattg gcatgaatct     300
cacgtgtggc gtgaaatcac gcgttataaa atgcacaacg cgctgtctcc atcatttaac     360
ttttcacgtg gcgtgaatca cttccaactg cgtaccaatc cgcagaccag tacgtacatg     420
acgcacgaag cggaggatga actgctgcgt agcgcattgc ataaattcac caatgtcgac     480
ggcactaatg ccgtacagt gttgccgttc ccacatgata tgttttatgt gccggaattt     540
cgcaagtatg acgaaatgtc atattccgaa cgcattgacc agatccgcga cgaactgtct     600
ttgaacgaac gctctagttt agaggctttc attttattat gtagcggtgg cacccctggaa     660 aactccagct ttggtgaatt tctgcattgg tgggcaatgt cgggttacac gtatcagggc     720
tgtatggatt gttttaatctc ctataaattt aaggatggcc agagtgcgtt cgcgcgtcgc     780
ttctgggaag aagccgctgg cactggccgt ctgggttatg tctttggttg tccggtgcgt     840
tctgtggtgg atgaacgcga cgcagtacgt gttaccgcac gtgacggtcg cgaattcgca     900
gcgaaacgtt tggtttgcac gattccgctg aacgtattga gttctgttca gtttagcccc a     960 ccactgtccc cgcaacgcat ggccgctgcg aacattggcc atgttaacca gtgcgtcaaa    1020
gtgcatgcgg aagtcagttg tccggatatg cgttcatggt cgggtgtgtc ctatccgttc    1080
aacaaattag cctgggctat cggcgatggc acgaccccag cgggtaatac gcatattgtg    1140
tgcttcgggg gcgctcataa tcatatccag ccggaagagg acgtggaagc aacgaagatg    1200
gccgttgaaa acatgtcgcc tgggaatatg gatatcaaac gtctggtctt ccacaactgg    1260
tgcaaggatg aatttgccaa aggcgcttgg ttcttcgccc ctccacagct gctgtcaaag    1320
agcctggatg aactgcgctg ccgtcacggt aatgtcctgt ttgcaaactc cgattgggcc    1380
ttaggttggc gtggttttat tgatggtgct atcgaggagg gcacccgcgc agcggttact    1440
gtaattgagg aactgcgtcc tgcgcctgcg gtgcgttccc acctgtaatg a             1491

<210> SEQ ID NO 20
<211> LENGTH: 495
<212> TYPE: PRT
<213> ORGANISM: Artificial Sequence
<220> FEATURE:
<223> OTHER INFORMATION: variant monoamine oxidase

<400> SEQUENCE: 20

Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Pro Thr Asn Ile Glu
            20                  25                  30

Asp Thr Asp Lys Asp Gly Pro Trp Asp Val Ile Val Ile Gly Gly Gly
        35                  40                  45

Tyr Cys Gly Leu Thr Ala Thr Arg Asp Leu Thr Val Ala Gly Phe Lys
    50                  55                  60
```

```
Thr Leu Leu Leu Glu Ala Arg Asp Arg Ile Gly Gly Arg Ser Trp Ser
 65                  70                  75                  80

Ser Asn Ile Asp Gly Tyr Pro Tyr Glu Met Gly Gly Thr Trp Val His
             85                  90                  95

Trp His Glu Ser His Val Trp Arg Glu Ile Thr Arg Tyr Lys Met His
            100                 105                 110

Asn Ala Leu Ser Pro Ser Phe Asn Phe Ser Arg Gly Val Asn His Phe
        115                 120                 125

Gln Leu Arg Thr Asn Pro Gln Thr Ser Thr Tyr Met Thr His Glu Ala
    130                 135                 140

Glu Asp Glu Leu Leu Arg Ser Ala Leu His Lys Phe Thr Asn Val Asp
145                 150                 155                 160

Gly Thr Asn Gly Arg Thr Val Leu Pro Phe Pro His Asp Met Phe Tyr
                165                 170                 175

Val Pro Glu Phe Arg Lys Tyr Asp Glu Met Ser Tyr Ser Glu Arg Ile
            180                 185                 190

Asp Gln Ile Arg Asp Glu Leu Ser Leu Asn Glu Arg Ser Ser Leu Glu
        195                 200                 205

Ala Phe Ile Leu Leu Cys Ser Gly Gly Thr Leu Glu Asn Ser Ser Phe
    210                 215                 220

Gly Glu Phe Leu His Trp Trp Ala Met Ser Gly Tyr Thr Tyr Gln Gly
225                 230                 235                 240

Cys Met Asp Cys Leu Ile Ser Tyr Lys Phe Lys Asp Gly Gln Ser Ala
                245                 250                 255

Phe Ala Arg Arg Phe Trp Glu Glu Ala Ala Gly Thr Gly Arg Leu Gly
            260                 265                 270

Tyr Val Phe Gly Cys Pro Val Arg Ser Val Val Asp Glu Arg Asp Ala
        275                 280                 285

Val Arg Val Thr Ala Arg Asp Gly Arg Glu Phe Ala Ala Lys Arg Leu
    290                 295                 300

Val Cys Thr Ile Pro Leu Asn Val Leu Ser Ser Val Gln Phe Ser Pro
305                 310                 315                 320

Pro Leu Ser Pro Gln Arg Met Ala Ala Ala Asn Ile Gly His Val Asn
                325                 330                 335

Gln Cys Val Lys Val His Ala Glu Val Ser Cys Pro Asp Met Arg Ser
            340                 345                 350

Trp Ser Gly Val Ser Tyr Pro Phe Asn Lys Leu Ala Trp Ala Ile Gly
        355                 360                 365

Asp Gly Thr Thr Pro Ala Gly Asn Thr His Ile Val Cys Phe Gly Gly
    370                 375                 380

Ala His Asn His Ile Gln Pro Glu Glu Asp Val Glu Ala Thr Lys Met
385                 390                 395                 400

Ala Val Glu Asn Met Ser Pro Gly Asn Met Asp Ile Lys Arg Leu Val
                405                 410                 415

Phe His Asn Trp Cys Lys Asp Glu Phe Ala Lys Gly Ala Trp Phe Phe
            420                 425                 430

Ala Pro Pro Gln Leu Leu Ser Lys Ser Leu Asp Glu Leu Arg Cys Arg
        435                 440                 445

His Gly Asn Val Leu Phe Ala Asn Ser Asp Trp Ala Leu Gly Trp Arg
    450                 455                 460

Gly Phe Ile Asp Gly Ala Ile Glu Glu Gly Thr Arg Ala Ala Val Thr
465                 470                 475                 480

Val Ile Glu Glu Leu Arg Pro Ala Pro Ala Val Arg Ser His Leu
```

|  | 485 | 490 | 495 |  |

<210> SEQ ID NO 21
<211> LENGTH: 2271
<212> TYPE: DNA
<213> ORGANISM: Artificial Sequence
<220> FEATURE:
<223> OTHER INFORMATION: monoamine oxidase MAOA

<400> SEQUENCE: 21

```
atgggaagcc cctctctgta ttctgcccgt aaaacaaccc tggcgttggc agtcgcctta      60
agtttcgcct ggcaagcgcc ggtatttgcc cacggtggtg aagcgcatat ggtgccaatg     120
gataaaacgc ttaaagaatt tggtgccgat gtgcagtggg acgactacgc ccagctcttt     180
accctgatta agatggcgc gtacgtgaaa gtgaagcctg gtgcgcaaac agcaattgtt     240
aatggtcagc ctctggcact gcaagtaccg gtagtgatga agacaataa agcctgggtt     300
tctgacacct ttattaacga tgttttccag tccgggctgg atcaaacctt tcaggtagaa     360
aagcgccctc acccacttaa tgcgctaact gcggacgaaa ttaaacaggc cgttgaaatt     420
gttaaagctt ccgcggactt caaacccaat acccgtttta ctgagatctc cctgctaccg     480
ccagataaag aagctgtctg ggcgtttgcg ctggaaaaca aaccggttga ccagccgcgc     540
aaagccgacg tcattatgct cgacggcaaa catatcatcg aagcggtggt ggatctgcaa     600
aacaacaaac tgctctcctg caacccatt aaagacgccc acggtatggt gttgctggat     660
gatttcgcca gtgtgcagaa cattattaac aacagtgaag aatttgccgc tgccgtgaag     720
aaacgcggta ttactgatgc gaaaaaagtg attaccacgc cgctgaccgt aggttatttc     780
gatggtaaag atggcctgaa acaagatgcc cggttgctca agtcatcag ctatcttgat     840
gtcggtgatg caactactg gcacatccc atcgaaaacc tggtgcggt cgttgattta     900
gaacagaaaa aaatcgttaa gattgaagaa ggtccggtag ttccggtgcc aatgaccgca     960
cgcccatttg atggccgtga ccgcgttgct ccggcagtta gcctatgca aatcattgag    1020
cctgaaggta aaaattacac cattactggc gatatgattc actggcggaa ctgggatttt    1080
cacctcagca tgaactctcg cgtcgggccg atgatctcca ccgtgactta aacgacaat    1140
ggcaccaaac gcaaagtcat gtacgaaggt tctctcggcg gcatgattgt gccttacggt    1200
gatcctgata ttggctggta cttttaaagcg tatctggact ctggtgacta cggtatgggc    1260
acgctaacct caccaattgc tcgtggtaaa gatgccccgt ctaacgcagt gctccttaat    1320
gaaaccatcg ccgactacac tggcgtgccg atggagatcc ctcgcgctat cgcggtattt    1380
gaacgttatg ccgggccgga gtataagcat caggaaatgg ccagcccaa cgtcagtacc    1440
gaacgccggg agttagtggt gcgctggatc agtacagtgg gtaactatga ctacattttt    1500
gactggatct ccatgaaaaa cggcactatt ggcatcgatg ccggtgctac gggcatcgaa    1560
gcggtgaaag tgttaaagc gaaaccatg acgatgaga cggcgaaaga tgacacgcgc    1620
tacggcacgc ttatcgatca aatatcgtg gtactacac accaacatat ttataattc    1680
cgcctcgatc tggatgtaga tggcgagaat aacagcctgg tggcgatgga cccagtggta    1740
aaaccgaata ctgccggtgg cccacgcacc agtaccatgc aagttaatca gtacaacatc    1800
ggcaatgaac aggatgccgc acagaaattt gatccgggca cgattcgtct gttgagtaac    1860
ccgaacaaag agaaccgcat gggcaatccg gtttcctatc aaattattcc ttatgcaggt    1920
ggtactcacc cggtagcaaa aggtgcccag ttcgcgccgg acgagtggat ctatcatcgt    1980
ttaagcttta tggacaagca gctctgggta acgcgttatc atcctggcga gcgtttcccg    2040
```

-continued

```
gaaggcaaat atccgaaccg ttctactcat gacaccggtc ttggacaata cagtaaggat    2100
aacgagtcgc tggacaacac cgacgccgtt gtctggatga ccaccggcac cacacatgtg    2160
gcccgcgccg aagagtggcc gattatgccg accgaatggg tacatactct gctgaaacca    2220
tggaacttct ttgacgaaac gccaacgcta ggggcgctga agaaagataa g             2271
```

<210> SEQ ID NO 22
<211> LENGTH: 757
<212> TYPE: PRT
<213> ORGANISM: Artificial Sequence
<220> FEATURE:
<223> OTHER INFORMATION: monoamine oxidase MAOA

<400> SEQUENCE: 22

```
Met Gly Ser Pro Ser Leu Tyr Ser Ala Arg Lys Thr Thr Leu Ala Leu
  1               5                  10                  15

Ala Val Ala Leu Ser Phe Ala Trp Gln Ala Pro Val Phe Ala His Gly
             20                  25                  30

Gly Glu Ala His Met Val Pro Met Asp Lys Thr Leu Lys Glu Phe Gly
         35                  40                  45

Ala Asp Val Gln Trp Asp Asp Tyr Ala Gln Leu Phe Thr Leu Ile Lys
     50                  55                  60

Asp Gly Ala Tyr Val Lys Val Lys Pro Gly Ala Gln Thr Ala Ile Val
 65                  70                  75                  80

Asn Gly Gln Pro Leu Ala Leu Gln Val Pro Val Val Met Lys Asp Asn
                 85                  90                  95

Lys Ala Trp Val Ser Asp Thr Phe Ile Asn Asp Val Phe Gln Ser Gly
            100                 105                 110

Leu Asp Gln Thr Phe Gln Val Glu Lys Arg Pro His Pro Leu Asn Ala
        115                 120                 125

Leu Thr Ala Asp Glu Ile Lys Gln Ala Val Glu Ile Val Lys Ala Ser
    130                 135                 140

Ala Asp Phe Lys Pro Asn Thr Arg Phe Thr Glu Ile Ser Leu Leu Pro
145                 150                 155                 160

Pro Asp Lys Glu Ala Val Trp Ala Phe Ala Leu Glu Asn Lys Pro Val
                165                 170                 175

Asp Gln Pro Arg Lys Ala Asp Val Ile Met Leu Asp Gly Lys His Ile
            180                 185                 190

Ile Glu Ala Val Val Asp Leu Gln Asn Asn Lys Leu Leu Ser Trp Gln
        195                 200                 205

Pro Ile Lys Asp Ala His Gly Met Val Leu Leu Asp Asp Phe Ala Ser
    210                 215                 220

Val Gln Asn Ile Ile Asn Asn Ser Glu Glu Phe Ala Ala Ala Val Lys
225                 230                 235                 240

Lys Arg Gly Ile Thr Asp Ala Lys Lys Val Ile Thr Thr Pro Leu Thr
                245                 250                 255

Val Gly Tyr Phe Asp Gly Lys Asp Gly Leu Lys Gln Asp Ala Arg Leu
            260                 265                 270

Leu Lys Val Ile Ser Tyr Leu Asp Val Gly Asp Gly Asn Tyr Trp Ala
        275                 280                 285

His Pro Ile Glu Asn Leu Val Ala Val Val Asp Leu Glu Gln Lys Lys
    290                 295                 300

Ile Val Lys Ile Glu Glu Gly Pro Val Pro Val Pro Met Thr Ala
305                 310                 315                 320

Arg Pro Phe Asp Gly Arg Asp Arg Val Ala Pro Ala Val Lys Pro Met
                325                 330                 335
```

```
Gln Ile Ile Glu Pro Glu Gly Lys Asn Tyr Thr Ile Thr Gly Asp Met
            340                 345                 350

Ile His Trp Arg Asn Trp Asp Phe His Leu Ser Met Asn Ser Arg Val
            355                 360                 365

Gly Pro Met Ile Ser Thr Val Thr Tyr Asn Asp Asn Gly Thr Lys Arg
            370                 375                 380

Lys Val Met Tyr Glu Gly Ser Leu Gly Gly Met Ile Val Pro Tyr Gly
385                 390                 395                 400

Asp Pro Asp Ile Gly Trp Tyr Phe Lys Ala Tyr Leu Asp Ser Gly Asp
                405                 410                 415

Tyr Gly Met Gly Thr Leu Thr Ser Pro Ile Ala Arg Gly Lys Asp Ala
                420                 425                 430

Pro Ser Asn Ala Val Leu Leu Asn Glu Thr Ile Ala Asp Tyr Thr Gly
                435                 440                 445

Val Pro Met Glu Ile Pro Arg Ala Ile Ala Val Phe Glu Arg Tyr Ala
450                 455                 460

Gly Pro Glu Tyr Lys His Gln Glu Met Gly Gln Pro Asn Val Ser Thr
465                 470                 475                 480

Glu Arg Arg Glu Leu Val Val Arg Trp Ile Ser Thr Val Gly Asn Tyr
                485                 490                 495

Asp Tyr Ile Phe Asp Trp Ile Phe His Glu Asn Gly Thr Ile Gly Ile
                500                 505                 510

Asp Ala Gly Ala Thr Gly Ile Glu Ala Val Lys Gly Val Lys Ala Lys
                515                 520                 525

Thr Met His Asp Glu Thr Ala Lys Asp Asp Thr Arg Tyr Gly Thr Leu
                530                 535                 540

Ile Asp His Asn Ile Val Gly Thr Thr His Gln His Ile Tyr Asn Phe
545                 550                 555                 560

Arg Leu Asp Leu Asp Val Asp Gly Glu Asn Asn Ser Leu Val Ala Met
                565                 570                 575

Asp Pro Val Val Lys Pro Asn Thr Ala Gly Gly Pro Arg Thr Ser Thr
                580                 585                 590

Met Gln Val Asn Gln Tyr Asn Ile Gly Asn Glu Gln Asp Ala Ala Gln
                595                 600                 605

Lys Phe Asp Pro Gly Thr Ile Arg Leu Leu Ser Asn Pro Asn Lys Glu
                610                 615                 620

Asn Arg Met Gly Asn Pro Val Ser Tyr Gln Ile Ile Pro Tyr Ala Gly
625                 630                 635                 640

Gly Thr His Pro Val Ala Lys Gly Ala Gln Phe Ala Pro Asp Glu Trp
                645                 650                 655

Ile Tyr His Arg Leu Ser Phe Met Asp Lys Gln Leu Trp Val Thr Arg
                660                 665                 670

Tyr His Pro Gly Glu Arg Phe Pro Glu Gly Lys Tyr Pro Asn Arg Ser
                675                 680                 685

Thr His Asp Thr Gly Leu Gly Gln Tyr Ser Lys Asp Asn Glu Ser Leu
                690                 695                 700

Asp Asn Thr Asp Ala Val Val Trp Met Thr Thr Gly Thr Thr His Val
705                 710                 715                 720

Ala Arg Ala Glu Glu Trp Pro Ile Met Pro Thr Glu Trp Val His Thr
                725                 730                 735

Leu Leu Lys Pro Trp Asn Phe Phe Asp Glu Thr Pro Thr Leu Gly Ala
                740                 745                 750

Leu Lys Lys Asp Lys
```

<210> SEQ ID NO 23
<211> LENGTH: 2007
<212> TYPE: DNA
<213> ORGANISM: Artificial Sequence
<220> FEATURE:
<223> OTHER INFORMATION: monoamine oxidase putA

<400> SEQUENCE: 23

| | |
|---|---|
| atgggaacca ccaccatggg ggttaagctg gacgacgcga cgcgtgagcg tattaagtct | 60 |
| gccgcgacac gtatcgatcg cacaccacac tggttaatta agcaggcgat tttttcttat | 120 |
| ctcgaacaac tggaaaacag cgatactctg ccggagctac ctgcgctgct ttctggcgcg | 180 |
| gccaatgaga gcgatgaagc accgactccg gcagaggaac cacaccagcc attcctcgac | 240 |
| tttgccgagc aaatattgcc ccagtcggtt tcccgcgccg cgatcaccgc ggcctatcgc | 300 |
| cgcccggaaa ccgaagcggt ttctatgctg ctggaacaag cccgcctgcc gcagccagtt | 360 |
| gctgaacagg cgcacaaact ggcgtatcag ctggccgata aactgcgtaa tcaaaaaaat | 420 |
| gccagtggtc gcgcaggtat ggtccagggg ttattgcagg agttttcgct gtcatcgcag | 480 |
| gaaggcgtgg cgctgatgtg tctggcggaa gcgttgttgc gtattcccga caaagccacc | 540 |
| cgcgacgcgt taattcgcga caaaatcagc aacggtaact ggcagtcaca cattggtcgt | 600 |
| agcccgtcac tgtttgttaa tgccgccacc tgggggctgc tgtttactgg caaactggtt | 660 |
| tccacccata cgaagccag cctctcccgc tcgctgaacc gcattatcgg taaaagcggt | 720 |
| gaaccgctga tccgcaaagg tgtggatatg gcgatgcgcc tgatgggtga gcagttcgtc | 780 |
| actggcgaaa ccatcgcgga agcgttagcc aatgcccgca agctggaaga gaaaggtttc | 840 |
| cgttactctt acgatatgct gggcgaagcc gcgctgaccg ccgcagatgc acaggcgtat | 900 |
| atggtttcct atcagcaggc gattcacgcc atcggtaaag cgtctaacgg tcgtggcatc | 960 |
| tatgaagggc cgggcatttc aatcaaactg tcggcgctgc atccgcgtta tagccgcgcc | 1020 |
| cagtatgacc gggtaatgga agagctttac ccgcgtctga atcactcac cctgctggcg | 1080 |
| cgtcagtacg atattggtat caacattgac gccgaagagt ccgatcgcct ggagatctcc | 1140 |
| ctcgatctgc tggaaaaact ctgtttcgag ccggaactgg caggctggaa cggcatcggt | 1200 |
| tttgttattc aggcttatca aaaacgctgc ccgttggtga tcgattacct gattgatctc | 1260 |
| gccacccgca gccgtcgccg tctgatgatt cgcctggtga aggcgcgta ctgggatagt | 1320 |
| gaaattaagc gtgcgcagat ggacggcctt gaaggttatc cggtttatac ccgcaaggtg | 1380 |
| tataccgacg tttcttatct cgcctgtgcg aaaaagctgc tggcggtgcc gaatctaatc | 1440 |
| tacccgcagt tcgcgacgca caacgcccat acgctggcgg cgatttatca actggcgggg | 1500 |
| cagaactact acccgggtca gtacgagttc cagtgcctgc atggtatggg cgagccactg | 1560 |
| tatgagcagg tcaccgggaa agttgccgac ggcaaactta accgtccgtg tcgtatttat | 1620 |
| gctccggttg gcacacatga aacgctgttg gcgtatctgg tgcgtcgcct gctggaaaac | 1680 |
| ggtgctaaca cctcgtttgt taaccgtatt gccgacacct ttttgccact ggatgaactg | 1740 |
| gtcgccgatc cggtcactgc tgtagaaaaa ctggcgcaac aggaagggca aactggatta | 1800 |
| ccgcatccga aaattcccct gccgcgcgat ctttacggtc acgggcgcga caactcggca | 1860 |
| gggctggatc tcgctaacga acaccgcctg cctcgctct cctctgccct gctcaatagt | 1920 |
| gcactgcaaa aatggcaggc cttgccaatg ctggacaac cggtagcggc aggtgagatg | 1980 |
| tcgcccgtta ttaaccctgc ggaaccg | 2007 |

-continued

<210> SEQ ID NO 24
<211> LENGTH: 669
<212> TYPE: PRT
<213> ORGANISM: Artificial Sequence
<220> FEATURE:
<223> OTHER INFORMATION: monoamine oxidase putA

<400> SEQUENCE: 24

```
Met Gly Thr Thr Thr Met Gly Val Lys Leu Asp Asp Ala Thr Arg Glu
1               5                   10                  15

Arg Ile Lys Ser Ala Ala Thr Arg Ile Asp Arg Thr Pro His Trp Leu
            20                  25                  30

Ile Lys Gln Ala Ile Phe Ser Tyr Leu Glu Gln Leu Glu Asn Ser Asp
        35                  40                  45

Thr Leu Pro Glu Leu Pro Ala Leu Leu Ser Gly Ala Ala Asn Glu Ser
    50                  55                  60

Asp Glu Ala Pro Thr Pro Ala Glu Pro His Gln Pro Phe Leu Asp
65                  70                  75                  80

Phe Ala Glu Gln Ile Leu Pro Gln Ser Val Ser Arg Ala Ala Ile Thr
                85                  90                  95

Ala Ala Tyr Arg Arg Pro Glu Thr Glu Ala Val Ser Met Leu Leu Glu
            100                 105                 110

Gln Ala Arg Leu Pro Gln Pro Val Ala Glu Gln Ala His Lys Leu Ala
        115                 120                 125

Tyr Gln Leu Ala Asp Lys Leu Arg Asn Gln Lys Asn Ala Ser Gly Arg
    130                 135                 140

Ala Gly Met Val Gln Gly Leu Leu Gln Glu Phe Ser Leu Ser Ser Gln
145                 150                 155                 160

Glu Gly Val Ala Leu Met Cys Leu Ala Glu Ala Leu Leu Arg Ile Pro
                165                 170                 175

Asp Lys Ala Thr Arg Asp Ala Leu Ile Arg Asp Lys Ile Ser Asn Gly
            180                 185                 190

Asn Trp Gln Ser His Ile Gly Arg Ser Pro Ser Leu Phe Val Asn Ala
        195                 200                 205

Ala Thr Trp Gly Leu Leu Phe Thr Gly Lys Leu Val Ser Thr His Asn
    210                 215                 220

Glu Ala Ser Leu Ser Arg Ser Leu Asn Arg Ile Ile Gly Lys Ser Gly
225                 230                 235                 240

Glu Pro Leu Ile Arg Lys Gly Val Asp Met Ala Met Arg Leu Met Gly
                245                 250                 255

Glu Gln Phe Val Thr Gly Glu Thr Ile Ala Glu Ala Leu Ala Asn Ala
            260                 265                 270

Arg Lys Leu Glu Glu Lys Gly Phe Arg Tyr Ser Tyr Asp Met Leu Gly
        275                 280                 285

Glu Ala Ala Leu Thr Ala Ala Asp Ala Gln Ala Tyr Met Val Ser Tyr
    290                 295                 300

Gln Gln Ala Ile His Ala Ile Gly Lys Ala Ser Asn Gly Arg Gly Ile
305                 310                 315                 320

Tyr Glu Gly Pro Gly Ile Ser Ile Lys Leu Ser Ala Leu His Pro Arg
                325                 330                 335

Tyr Ser Arg Ala Gln Tyr Asp Arg Val Met Glu Glu Leu Tyr Pro Arg
            340                 345                 350

Leu Lys Ser Leu Thr Leu Leu Ala Arg Gln Tyr Asp Ile Gly Ile Asn
        355                 360                 365

Ile Asp Ala Glu Glu Ser Asp Arg Leu Glu Ile Ser Leu Asp Leu Leu
```

| | | | | | | | | | | |
|---|---|---|---|---|---|---|---|---|---|---|
| | | 370 | | | 375 | | | 380 | | |
| Glu | Lys | Leu | Cys | Phe | Glu | Pro | Glu | Leu | Ala | Gly | Trp | Asn | Gly | Ile | Gly |
| 385 | | | | | 390 | | | | | 395 | | | | | 400 |

Phe Val Ile Gln Ala Tyr Gln Lys Arg Cys Pro Leu Val Ile Asp Tyr
                405                410                415

Leu Ile Asp Leu Ala Thr Arg Ser Arg Arg Leu Met Ile Arg Leu
          420                425              430

Val Lys Gly Ala Tyr Trp Asp Ser Glu Ile Lys Arg Ala Gln Met Asp
              435                440              445

Gly Leu Glu Gly Tyr Pro Val Tyr Thr Arg Lys Val Tyr Thr Asp Val
450                455              460

Ser Tyr Leu Ala Cys Ala Lys Lys Leu Leu Ala Val Pro Asn Leu Ile
465                470              475              480

Tyr Pro Gln Phe Ala Thr His Asn Ala His Thr Leu Ala Ala Ile Tyr
              485              490              495

Gln Leu Ala Gly Gln Asn Tyr Tyr Pro Gly Gln Tyr Glu Phe Gln Cys
          500                505              510

Leu His Gly Met Gly Glu Pro Leu Tyr Glu Gln Val Thr Gly Lys Val
            515              520              525

Ala Asp Gly Lys Leu Asn Arg Pro Cys Arg Ile Tyr Ala Pro Val Gly
      530                535              540

Thr His Glu Thr Leu Leu Ala Tyr Leu Val Arg Arg Leu Leu Glu Asn
545                550              555              560

Gly Ala Asn Thr Ser Phe Val Asn Arg Ile Ala Asp Thr Ser Leu Pro
            565              570              575

Leu Asp Glu Leu Val Ala Asp Pro Val Thr Ala Val Glu Lys Leu Ala
          580                585              590

Gln Gln Glu Gly Gln Thr Gly Leu Pro His Pro Lys Ile Pro Leu Pro
         595                600              605

Arg Asp Leu Tyr Gly His Gly Arg Asp Asn Ser Ala Gly Leu Asp Leu
      610                615              620

Ala Asn Glu His Arg Leu Ala Ser Leu Ser Ser Ala Leu Leu Asn Ser
625                630              635              640

Ala Leu Gln Lys Trp Gln Ala Leu Pro Met Leu Glu Gln Pro Val Ala
            645              650              655

Ala Gly Glu Met Ser Pro Val Ile Asn Pro Ala Glu Pro
          660                665

<210> SEQ ID NO 25
<211> LENGTH: 1110
<212> TYPE: DNA
<213> ORGANISM: Artificial Sequence
<220> FEATURE:
<223> OTHER INFORMATION: monoamine oxidase goxB 1

<400> SEQUENCE: 25

```
atgaaaaggc attatgaagc agttgtcatt ggaggcggaa ttattggttc cgcgattgct      60
tatcagttgg caaagaaaaa gaaaacacc gcattgcttg aaagcggaac aatcggcggc     120
agaacaacaa gcgccgcggc agggatgctt ggcgcccatg ccgagtgcga ggaacgggat     180
gcgttttttg atttcgccat gcacagtcag cgtatgtacc gaggtcttgg agaggagcta     240
tttgcattat ccggtatcga tattagaagg catgatggcg gtatgtttaa gcttgcattc     300
tccgaagaag acgtgtcacg cctcagacgg atggacgatt tggattctgt cagctggcat     360
acaaaagaag aagtgctgga aaaagagccg tatacggcca gtgagattta cggggcgagc     420
```

```
tttattcagg atgatgttca tgttgagcct tattttgtat gcaaggcata cgctaaatcg    480
gctaaagcgc ttggtgcgga tattttgag catactcctg ttctcgatgt gacatgtggc    540
ggtgaatcca ttttggtcaa aacagcgtcc ggtgacatgc atgcggatca tgtcgtggtt    600
gccagcgggg tctggagcgg gatgtttttt aagcagctcg ggctgaatca gtcattttt    660 cctgtaaaag gagagtgcct gtctgtttgg aatgatgaca ttccgctgac aaaaacactt    720
tatcatgatc attgctatat cgtaccgaga aaaagcggca gactggttgt cggcgcgacg    780
atgaagcctg gtgactggag cgagaaggcg gatcttggcg gacttcagtc ggttatggaa    840
aaagcgaaaa cgatgctgcc ggcgattcag aatatgaagg ttgatcgttt ttgggcggga    900
ctgcgtccgg ggacaaagga cggaaagcca tacattggca agcaccctca ggacagccgc    960 attttattg cggcgggcca tttcagaaac gggattctgc ttgctcctgc aacgggtgct   1020
ttaattggtg atctcattat gaataaagag gtcaaggcgg actggctgca cgcctttcga   1080
attgatcgca aggaggcggt tcagatatga                                    1110
```

<210> SEQ ID NO 26
<211> LENGTH: 369
<212> TYPE: PRT
<213> ORGANISM: Artificial Sequence
<220> FEATURE:
<223> OTHER INFORMATION: monoamine oxidase goxB 1

<400> SEQUENCE: 26

```
Met Lys Arg His Tyr Glu Ala Val Val Ile Gly Gly Gly Ile Ile Gly
1               5                   10                  15

Ser Ala Ile Ala Tyr Gln Leu Ala Lys Glu Lys Lys Asn Thr Ala Leu
            20                  25                  30

Leu Glu Ser Gly Thr Ile Gly Gly Arg Thr Thr Ser Ala Ala Ala Gly
        35                  40                  45

Met Leu Gly Ala His Ala Glu Cys Glu Glu Arg Asp Ala Phe Phe Asp
    50                  55                  60

Phe Ala Met His Ser Gln Arg Met Tyr Arg Gly Leu Gly Glu Glu Leu
65                  70                  75                  80

Phe Ala Leu Ser Gly Ile Asp Ile Arg Arg His Asp Gly Gly Met Phe
                85                  90                  95

Lys Leu Ala Phe Ser Glu Glu Asp Val Ser Arg Leu Arg Arg Met Asp
            100                 105                 110

Asp Leu Asp Ser Val Ser Trp His Thr Lys Glu Glu Val Leu Glu Lys
        115                 120                 125

Glu Pro Tyr Thr Ala Ser Glu Ile Tyr Gly Ala Ser Phe Ile Gln Asp
    130                 135                 140

Asp Val His Val Glu Pro Tyr Phe Val Cys Lys Ala Tyr Ala Lys Ser
145                 150                 155                 160

Ala Lys Ala Leu Gly Ala Asp Ile Phe Glu His Thr Pro Val Leu Asp
                165                 170                 175

Val Thr Cys Gly Gly Glu Ser Ile Leu Val Lys Thr Ala Ser Gly Asp
            180                 185                 190

Met His Ala Asp His Val Val Ala Ser Gly Val Trp Ser Gly Met
        195                 200                 205

Phe Phe Lys Gln Leu Gly Leu Asn Gln Ser Phe Pro Val Lys Gly
    210                 215                 220

Glu Cys Leu Ser Val Trp Asn Asp Asp Ile Pro Leu Thr Lys Thr Leu
225                 230                 235                 240

Tyr His Asp His Cys Tyr Ile Val Pro Arg Lys Ser Gly Arg Leu Val
```

245                 250                 255
Val Gly Ala Thr Met Lys Pro Gly Asp Trp Ser Glu Lys Ala Asp Leu
            260                 265                 270

Gly Gly Leu Gln Ser Val Met Glu Lys Ala Lys Thr Met Leu Pro Ala
        275                 280                 285

Ile Gln Asn Met Lys Val Asp Arg Phe Trp Ala Gly Leu Arg Pro Gly
        290                 295                 300

Thr Lys Asp Gly Lys Pro Tyr Ile Gly Lys His Pro Gln Asp Ser Arg
305                 310                 315                 320

Ile Leu Phe Ala Ala Gly His Phe Arg Asn Gly Ile Leu Leu Ala Pro
                325                 330                 335

Ala Thr Gly Ala Leu Ile Gly Asp Leu Ile Met Asn Lys Glu Val Lys
            340                 345                 350

Ala Asp Trp Leu His Ala Phe Arg Ile Asp Arg Lys Glu Ala Val Gln
        355                 360                 365

Ile

<210> SEQ ID NO 27
<211> LENGTH: 1110
<212> TYPE: DNA
<213> ORGANISM: Artificial Sequence
<220> FEATURE:
<223> OTHER INFORMATION: monoamine oxidase goxB 5

<400> SEQUENCE: 27
atgaaaaggc attatgaagc agtggtgatt ggaggcggaa ttatcggttc cgcaattgct       60
tattatttgg caaaggaaaa caaaaacacc gcattgtttg aaagcggaac aatgggcggc      120
agaacgacaa gtgccgctgc cggaatgctg ggcgcccatg ccgaatgcga ggaacgtgac      180
gcgttttttg atttcgccat gcacagccag cgtctgtaca aaggtcttgg agaagagctt      240
tatgcattat ccggtgtgga tatcaggcag cataacggcg gtatgtttaa gcttgcattt      300
tctgaagaag atgtgctgca gctgagacag atggacgatt ggactctgt cagctggtat       360
tcaaaagaag aggtgttaga aaaagagccg tatgcgtctg gtgacatctt tggtgcatct      420
tttattcagg atgatgtgca tgtggagcct tattttgttt gcaaggcata tgtgaaagca      480
gcaaaaatgc ttggggcgga gatttttgag catacgcccg tcctgcatgt cgaacgtgac      540
ggtgaagccc tgtccatcaa gaccctagc ggagacgtat gggctaatca tgttgtcgtt       600
gccagcgggg tgtggagcgg aatgttttt aaacagcttg gactgaacaa tgcttttctc       660
cctgtaaaag gggagtgcct gtccgtttgg aatgatgata tcccgctgac aaaaacgctt      720
taccatgatc actgctatat cgtaccgaga aaaagcggca aactggttgt cggcgcgaca      780
atgaagccgg gggactggag tgaaacaccg gatcttggcg gattggaatc cgttatgaaa      840
aaagcaaaaa cgatgctgcc ggctatacag aaatatgaagg tggatcgttt ttgggcggga      900
ctccgtccgg gaacaaagga tggaaaaccg tacatcggca gacatcctga ggacagccgt      960
attttatttg cggctggcca tttcagaaat gggatcctgc ttgctcccgc aacgggcgct     1020
tgatcagtg atctcatcat gaataaagag gtcaaccaag actggctgca cgcattccga     1080
attgatcgca aggaggcggt tcagatatga                                      1110

<210> SEQ ID NO 28
<211> LENGTH: 369
<212> TYPE: PRT
<213> ORGANISM: Artificial Sequence
<220> FEATURE:
<223> OTHER INFORMATION: monoamine oxidase goxB 5

<400> SEQUENCE: 28

```
Met Lys Arg His Tyr Glu Ala Val Val Ile Gly Gly Gly Ile Ile Gly
1               5                   10                  15

Ser Ala Ile Ala Tyr Tyr Leu Ala Lys Glu Asn Lys Asn Thr Ala Leu
            20                  25                  30

Phe Glu Ser Gly Thr Met Gly Gly Arg Thr Thr Ser Ala Ala Ala Gly
        35                  40                  45

Met Leu Gly Ala His Ala Glu Cys Glu Glu Arg Asp Ala Phe Phe Asp
50                  55                  60

Phe Ala Met His Ser Gln Arg Leu Tyr Lys Gly Leu Gly Glu Glu Leu
65                  70                  75                  80

Tyr Ala Leu Ser Gly Val Asp Ile Arg Gln His Asn Gly Gly Met Phe
                85                  90                  95

Lys Leu Ala Phe Ser Glu Glu Asp Val Leu Gln Leu Arg Gln Met Asp
            100                 105                 110

Asp Leu Asp Ser Val Ser Trp Tyr Ser Lys Glu Val Leu Glu Lys
            115                 120                 125

Glu Pro Tyr Ala Ser Gly Asp Ile Phe Gly Ala Ser Phe Ile Gln Asp
130                 135                 140

Asp Val His Val Glu Pro Tyr Phe Val Cys Lys Ala Tyr Val Lys Ala
145                 150                 155                 160

Ala Lys Met Leu Gly Ala Glu Ile Phe Glu His Thr Pro Val Leu His
                165                 170                 175

Val Glu Arg Asp Gly Gly Ala Leu Ser Ile Lys Thr Pro Ser Gly Asp
            180                 185                 190

Val Trp Ala Asn His Val Val Ala Ser Gly Val Trp Ser Gly Met
        195                 200                 205

Phe Phe Lys Gln Leu Gly Leu Asn Asn Ala Phe Leu Pro Val Lys Gly
210                 215                 220

Glu Cys Leu Ser Val Trp Asn Asp Asp Ile Pro Leu Thr Lys Thr Leu
225                 230                 235                 240

Tyr His Asp His Cys Tyr Ile Val Pro Arg Lys Ser Gly Lys Leu Val
                245                 250                 255

Val Gly Ala Thr Met Lys Pro Gly Asp Trp Ser Glu Thr Pro Asp Leu
            260                 265                 270

Gly Gly Leu Glu Ser Val Met Lys Lys Ala Lys Thr Met Leu Pro Ala
        275                 280                 285

Ile Gln Asn Met Lys Val Asp Arg Phe Trp Ala Gly Leu Arg Pro Gly
290                 295                 300

Thr Lys Asp Gly Lys Pro Tyr Ile Gly Arg His Pro Glu Asp Ser Arg
305                 310                 315                 320

Ile Leu Phe Ala Ala Gly His Phe Arg Asn Gly Ile Leu Leu Ala Pro
                325                 330                 335

Ala Thr Gly Ala Leu Ile Ser Asp Leu Ile Met Asn Lys Glu Val Asn
            340                 345                 350

Gln Asp Trp Leu His Ala Phe Arg Ile Asp Arg Lys Glu Ala Val Gln
        355                 360                 365

Ile
```

<210> SEQ ID NO 29
<211> LENGTH: 1479
<212> TYPE: DNA
<213> ORGANISM: Artificial Sequence
<220> FEATURE:

<223> OTHER INFORMATION: monoamine oxidase MAO-2

<400> SEQUENCE: 29

```
atgaccaccc aggacggctg tcattatcac attaacgagg gtctgaccca tggcgtaccg      60
tcccgtgcta aaatttatcc ggcggaacgc ctggcacagg ccagcagac cttggatacc      120
attgtcattg gggccgggta tgctgggctg atcgcagccc gtaatttagc cctgcaaggg      180
aaacgtgtgg tgctgctgga ggcccgtgat cgtattggtg gccgcacctt taccagtgat      240
attgacggtt acgggtatga gatgggtggc aattggattc attggggtca acctcacgtg      300
tatgctgaag tctcgcgtta tagcatggcc aacgagctgg tttcatcaca ggactataca      360
tatgaagagg gtaactactg ctcgactatg attcatggcg tcggtgggcg cctgacgcac      420
caagaggagg aacatattgg ggaaaccgca atgtctattt tctgcaatgt cgacggtcag      480
gatggccgtg gggtggtgcc gttcccacat aatgcgactc ataacgcgga ggcatttgcc      540
acgtgggaca aagtgtcatg tcaggatcgc ctggaccaga tcaaagacaa actgtctccg      600
ctgcaactgg cttttttaac gtctaccctg atgcatatta gcggtgccaa caacgaagac      660
gtcagcgttg ctgaattgct gcgttggtgg gcactgtgcg attaccgtaa ttcgggcatt      720
acggattatg ggctgttgta taaattgaag tgtggccaga ctgggttggc gaaagccatc      780
tttaacgaag gcgttctgct gggcaatctg cagtataaat ttagtgctcc ggtggttact      840
attcgtgacg aaggcgcctc agtagaagtt accacacgtg gcggtcagca attccgtgcg      900
aaaactgtga ttagcacgat tccgctgaac gtattgagtt ctattcagtt taccccacca      960
ctgcctacgg ggaaagtctt ggctgcgcgt caaggccatg ttaacaaggc caccaaaacg     1020
catttgaag tcgaaggtac ggctatgcgt tcatggtcgg tgtcgcccta tccgtccaaa     1080
gggcaaatgt acctgtacgg cgatggcctg accccagcgg gtaatacgca tattattgcc     1140
ttcgggccag acccggaact gctgcgggc aaggacgtgg aaaaaattaa gggggccctg     1200
acccatgtga aggatgccga agtcaaacgt attgtcttcc acgactggaa ccaggatgaa     1260
ttttcccaag gcacgtgggc cgtctaccct ccaaactttg ctacaaagta cctggataat     1320
ctgcagaagc cagtcggtcg tatccatttt gcaagcgccg attgggccga aggttggcgt     1380
ggttttatcg atggtgctat cgagcagggc gtccgcgcat cgctggctgt atcgaaggaa     1440
ctggcgagcc atcgcgcggc gccgaaacgt tcccacctg                            1479
```

<210> SEQ ID NO 30
<211> LENGTH: 493
<212> TYPE: PRT
<213> ORGANISM: Artificial Sequence
<220> FEATURE:
<223> OTHER INFORMATION: monoamine oxidase MAO-2

<400> SEQUENCE: 30

```
Met Thr Thr Gln Asp Gly Cys His Tyr His Ile Asn Glu Gly Leu Thr
1               5                   10                  15

His Gly Val Pro Ser Arg Ala Lys Ile Tyr Pro Ala Glu Arg Leu Ala
            20                  25                  30

Gln Gly Gln Gln Thr Leu Asp Thr Ile Val Ile Gly Ala Gly Tyr Ala
        35                  40                  45

Gly Leu Ile Ala Ala Arg Asn Leu Ala Leu Gln Gly Lys Arg Val Val
    50                  55                  60

Leu Leu Glu Ala Arg Asp Arg Ile Gly Gly Arg Thr Phe Thr Ser Asp
65                  70                  75                  80

Ile Asp Gly Tyr Gly Tyr Glu Met Gly Gly Asn Trp Ile His Trp Gly
```

-continued

```
                85                  90                  95
Gln Pro His Val Tyr Ala Glu Val Ser Arg Tyr Ser Met Ala Asn Glu
            100                 105                 110

Leu Val Ser Ser Gln Asp Tyr Thr Tyr Glu Glu Gly Asn Tyr Cys Ser
            115                 120                 125

Thr Met Ile His Gly Val Gly Arg Leu Thr His Gln Glu Glu Glu
            130                 135                 140

His Ile Gly Glu Thr Ala Met Ser Ile Phe Cys Asn Val Asp Gly Gln
145                 150                 155                 160

Asp Gly Arg Gly Val Val Pro Phe Pro His Asn Ala Thr His Asn Ala
                165                 170                 175

Glu Ala Phe Ala Thr Trp Asp Lys Val Ser Cys Gln Asp Arg Leu Asp
            180                 185                 190

Gln Ile Lys Asp Lys Leu Ser Pro Leu Gln Leu Ala Phe Leu Thr Ser
            195                 200                 205

Thr Leu Met His Ile Ser Gly Ala Asn Asn Glu Asp Val Ser Val Ala
210                 215                 220

Glu Leu Leu Arg Trp Trp Ala Leu Cys Asp Tyr Arg Asn Ser Gly Ile
225                 230                 235                 240

Thr Asp Tyr Gly Leu Leu Tyr Lys Leu Lys Cys Gly Gln Thr Gly Leu
                245                 250                 255

Ala Lys Ala Ile Phe Asn Glu Gly Val Leu Leu Gly Asn Leu Gln Tyr
            260                 265                 270

Lys Phe Ser Ala Pro Val Val Thr Ile Arg Asp Glu Gly Ala Ser Val
            275                 280                 285

Glu Val Thr Thr Arg Gly Gly Gln Gln Phe Arg Ala Lys Thr Val Ile
            290                 295                 300

Ser Thr Ile Pro Leu Asn Val Leu Ser Ser Ile Gln Phe Thr Pro Pro
305                 310                 315                 320

Leu Pro Thr Gly Lys Val Leu Ala Ala Arg Gln Gly His Val Asn Lys
                325                 330                 335

Ala Thr Lys Thr His Phe Glu Val Glu Gly Thr Ala Met Arg Ser Trp
            340                 345                 350

Ser Gly Val Ala Tyr Pro Ser Lys Gly Gln Met Tyr Leu Tyr Gly Asp
            355                 360                 365

Gly Leu Thr Pro Ala Gly Asn Thr His Ile Ile Ala Phe Gly Pro Asp
            370                 375                 380

Pro Glu Leu Leu Ala Gly Lys Asp Val Glu Lys Ile Lys Gly Ala Leu
385                 390                 395                 400

Thr His Val Lys Asp Ala Glu Val Lys Arg Ile Val Phe His Asp Trp
                405                 410                 415

Asn Gln Asp Glu Phe Ser Gln Gly Thr Trp Ala Val Tyr Pro Pro Asn
            420                 425                 430

Phe Ala Thr Lys Tyr Leu Asp Asn Leu Gln Lys Pro Val Gly Arg Ile
            435                 440                 445

His Phe Ala Ser Ala Asp Trp Ala Glu Gly Trp Arg Gly Phe Ile Asp
            450                 455                 460

Gly Ala Ile Glu Gln Gly Val Arg Ala Ser Leu Ala Val Ser Lys Glu
465                 470                 475                 480

Leu Ala Ser His Arg Ala Ala Pro Lys Arg Ser His Leu
                485                 490

<210> SEQ ID NO 31
<211> LENGTH: 1479
```

```
<212> TYPE: DNA
<213> ORGANISM: Artificial Sequence
<220> FEATURE:
<223> OTHER INFORMATION: Aspergillus oryzae monoamine oxidase (MAO-3)

<400> SEQUENCE: 31
atgaccagcc gcgacggcta tcagtggacc gcgacaacgg gtctgcgcca gggcgtaccg      60
tccattggtg tcatttcgcc gccgactaac gtcttaagta ccactgagga ctgggatgtc     120
gttgtcgttg gggccgggta ttctgggctg accgcaagcc gtgatgcatg cctggcaggg     180
ttgaaggtgc tgctgattga ggcccgtgat cgtattggtg gccgctcctg gagcagtaat     240
attggcggtt acccgtttga gatgggtggc acttggctgt cttggggtca acctcacatt     300
tggcgtgaag tctcgcgtta tcaaatgcgc agcgagctgg aaccatgctt tgacttttca     360
cgtggcgtga atcacttcga actgcgtacc ggttcgcagg gcagttcgat cttttcgcac     420
ttagaggagg atgcactgct ggctagcgca ttggaaaaat cgtcgatgt cgacggcgct     480
atgggccgtc aaattattcc gtacccacat gatgcgtttc ataacccggc agctcgccag     540
tatgacgata tgtcagcttt ggatcgcctg aacgcgctgg cccagagcct gactccgaac     600
gaacgcgctg ttttagagtc tttcatttta ttatgtagct gtggcaccct ggaaaccacc     660
agctttttg aatttctgca ttggtgggca ctgtgcgatt actcgtataa gggctgtctg     720
cagcatttaa tctcctataa atttaagggt ggccagagtt cgttcgcgat taaattcttt     780
cgtgaatccc tgcgcactgg ccgtctgagc tatgccttta ttctccggt gcagtctatt     840
aacgaccatg cgaccgtgt agttgttaaa acacgtgacg tcgccaata ctcaggggca     900
cgtttgatta gcacgattcc gctgaacgta ttgagttctg ttcattttag cccaccactg     960
tccccgcaac gcatggccgc tgcgaacatt ggccatgtta ccagtgcgt caaagtgcat    1020
gcggaagtca gttgtccgga tatgcgttca tggtcgggta tctcctatcc gttcaacaaa    1080
ttagcctacg ctatcggcga tggcacgacc ccagcgggta atacgcatat tgtgtgcttc    1140
ggggggccc ataatcatat ccagccggaa gaggacgtgg aagcaacgaa gatggccgtt    1200
gaaaacatgt cgcctgggaa tatggatatc aaacgtctgg tcttccacaa ctggtgcaag    1260
gatgaatttg ccaaaggcgc gtggttcttc gcccctccac agctgctgtc aaagagcctg    1320
gatgaactgc gctgccgtca cggtaatgtc ctgtttgcaa actccgattg ggccgtaggt    1380
tggcgtagtt ttatcgatgg tgctatcgag gagggcaccc gcgcagcggt tactgtaatt    1440
gaggaactgc gtcctgcgcc tgcggtgcgt tcccacctg                           1479

<210> SEQ ID NO 32
<211> LENGTH: 493
<212> TYPE: PRT
<213> ORGANISM: Artificial Sequence
<220> FEATURE:
<223> OTHER INFORMATION: Aspergillus oryzae monoamine oxidase (MAO-3)

<400> SEQUENCE: 32

Met Thr Ser Arg Asp Gly Tyr Gln Trp Thr Ala Thr Thr Gly Leu Arg
1               5                   10                  15

Gln Gly Val Pro Ser Ile Gly Val Ile Ser Pro Pro Thr Asn Val Leu
                20                  25                  30

Ser Thr Thr Glu Asp Trp Asp Val Val Val Gly Ala Gly Tyr Ser
            35                  40                  45

Gly Leu Thr Ala Ser Arg Asp Ala Cys Leu Ala Gly Leu Lys Val Leu
        50                  55                  60

Leu Ile Glu Ala Arg Asp Arg Ile Gly Gly Arg Ser Trp Ser Ser Asn
```

```
                65                  70                  75                  80
Ile Gly Gly Tyr Pro Phe Glu Met Gly Gly Thr Trp Leu Ser Trp Gly
                        85                  90                  95

Gln Pro His Ile Trp Arg Glu Val Ser Arg Tyr Gln Met Arg Ser Glu
            100                 105                 110

Leu Glu Pro Cys Phe Asp Phe Ser Arg Gly Val Asn His Phe Glu Leu
            115                 120                 125

Arg Thr Gly Ser Gln Gly Ser Ser Ile Phe Ser His Leu Glu Glu Asp
    130                 135                 140

Ala Leu Leu Ala Ser Ala Leu Glu Lys Phe Val Asp Val Asp Gly Ala
145                 150                 155                 160

Met Gly Arg Gln Ile Ile Pro Tyr Pro His Asp Ala Phe His Asn Pro
                165                 170                 175

Ala Ala Arg Gln Tyr Asp Asp Met Ser Ala Leu Asp Arg Leu Asn Ala
            180                 185                 190

Leu Ala Gln Ser Leu Thr Pro Asn Glu Arg Ala Val Leu Glu Ser Phe
    195                 200                 205

Ile Leu Leu Cys Ser Cys Gly Thr Leu Glu Thr Thr Ser Phe Phe Glu
210                 215                 220

Phe Leu His Trp Trp Ala Leu Cys Asp Tyr Ser Tyr Lys Gly Cys Leu
225                 230                 235                 240

Gln His Leu Ile Ser Tyr Lys Phe Lys Gly Gly Gln Ser Ser Phe Ala
                245                 250                 255

Ile Lys Phe Phe Arg Glu Ser Leu Arg Thr Gly Arg Leu Ser Tyr Ala
            260                 265                 270

Phe Asn Ser Pro Val Gln Ser Ile Asn Asp His Gly Asp Arg Val Val
            275                 280                 285

Val Lys Thr Arg Asp Gly Arg Gln Tyr Ser Gly Ala Arg Leu Ile Ser
    290                 295                 300

Thr Ile Pro Leu Asn Val Leu Ser Ser Val His Phe Ser Pro Pro Leu
305                 310                 315                 320

Ser Pro Gln Arg Met Ala Ala Ala Asn Ile Gly His Val Asn Gln Cys
                325                 330                 335

Val Lys Val His Ala Glu Val Ser Cys Pro Asp Met Arg Ser Trp Ser
            340                 345                 350

Gly Ile Ser Tyr Pro Phe Asn Lys Leu Ala Tyr Ala Ile Gly Asp Gly
            355                 360                 365

Thr Thr Pro Ala Gly Asn Thr His Ile Val Cys Phe Gly Gly Ala His
    370                 375                 380

Asn His Ile Gln Pro Glu Glu Asp Val Glu Ala Thr Lys Met Ala Val
385                 390                 395                 400

Glu Asn Met Ser Pro Gly Asn Met Asp Ile Lys Arg Leu Val Phe His
                405                 410                 415

Asn Trp Cys Lys Asp Glu Phe Ala Lys Gly Ala Trp Phe Phe Ala Pro
            420                 425                 430

Pro Gln Leu Leu Ser Lys Ser Leu Asp Glu Leu Arg Cys Arg His Gly
            435                 440                 445

Asn Val Leu Phe Ala Asn Ser Asp Trp Ala Val Gly Trp Arg Ser Phe
    450                 455                 460

Ile Asp Gly Ala Ile Glu Gly Thr Arg Ala Ala Val Thr Val Ile
465                 470                 475                 480

Glu Glu Leu Arg Pro Ala Pro Ala Val Arg Ser His Leu
                485                 490
```

<210> SEQ ID NO 33
<211> LENGTH: 1476
<212> TYPE: DNA
<213> ORGANISM: Artificial Sequence
<220> FEATURE:
<223> OTHER INFORMATION: monoamine oxidase MAO-4

<400> SEQUENCE: 33

```
atgaccagcc gcgacggcta tcagtggacc gcggaaacgg gtctggtcca gggcgtaccg      60
tccattagtg tcatttcgcc gccgactaac atcagccctg aaagtcgtca gtatgatgtc     120
gttgtcgttg gggccgggta ttctgggctg accgcagccc gtgatacatg cctggcaggg     180
ttgaaggtgc tgctgctgga ggcccgtgat cgtattggtg gccgctcctg gagcagtgat     240
attggcggtt acccgtttga gatgggtggc acttggggttc attggggtca acctcacgtg     300
tggcgtgaaa tctcgcgtta tcaaatgcgc aacgagctgg aatcatcatt tgactttca     360
cgtggcgtga atcacttcga actgcgtacc aatcagggcc ctgcgatcat gtcgcacaaa     420
gaggaggatg aactgctggc tgccgcattg cataaattcg tcgatgtcga cggcgatctg     480
ggccgtcgtg cggtgccgtt ccacatgat tcgtttcatg tgccggaagc tcgccagtat     540
gaccaaatgt cagctaaaga tcgcatgacc cagatcgccg acacagtgtc tccgcgcgaa     600
cgcgctgctt tagagtcttt cgttttatta tgtagcggtg gcaccctggc aaccaccagc     660
ttttttgaat ttctgcattg gtgggcactg tgcggttact cgtatcaggg ctgtctggat     720
gctttaatct cctataaatt taagcgtggc cagagttcgt tcgcgctgcg cttctttcgt     780
gaagccctga gcactggcaa tctgagctat gcctttaatt ctccgattca gtctattgat     840
gaccaaggcg ccaaagtagt tgttaccaca cgtgaaggtc accgttacgc aggggcacgt     900
ttgattagca cgattccgct gaacgtattg aatactgtta cgattagccc accactgggc     960
acgcaacgca ccgccgctgc gaacacaggc catgttaacc agtgcgtcaa agtgcatgcg    1020
gaaatcgcta gtcgtgatat gcgttcatgg acgggtatct cctatccgtt caacaaatta    1080
tgctacgcta tcggcgatgg cacgacccca gcgggtaata cgcatattgt gtgcttcggg    1140
gggagccata atcatatcca gccggaagag gacattaaac aaacgaagac agccgttgaa    1200
tcactgtcgc ctgggaatat ggatatcaaa cgtctggtct ccacaactg gtcaaaggat    1260
gaatttgcca aaggcgcgtg gttcttcagc cctccagaaa tgctgtcaac gagcctggag    1320
gctctgcgca gccgtcacgg taatgtcgtg ttggcaaact ccgattgggc cttaggttgg    1380
cgtagtttta tcgatggtgc tatcgaggag ggcacccgcg cagcgatgac tgtagtggag    1440
gaactgcgtc ctcagcctgc ggtgcgtgaa cacctg                              1476
```

<210> SEQ ID NO 34
<211> LENGTH: 492
<212> TYPE: PRT
<213> ORGANISM: Artificial Sequence
<220> FEATURE:
<223> OTHER INFORMATION: monoamine oxidase MAO-4

<400> SEQUENCE: 34

```
Met Thr Ser Arg Asp Gly Tyr Gln Trp Thr Ala Glu Thr Gly Leu Val
1               5                  10                  15

Gln Gly Val Pro Ser Ile Ser Val Ile Ser Pro Pro Thr Asn Ile Ser
            20                  25                  30

Pro Glu Ser Arg Gln Tyr Asp Val Val Val Gly Ala Gly Tyr Ser
        35                  40                  45

Gly Leu Thr Ala Ala Arg Asp Thr Cys Leu Ala Gly Leu Lys Val Leu
```

```
                50                      55                      60
Leu Leu Glu Ala Arg Asp Arg Ile Gly Gly Arg Ser Trp Ser Ser Asp
 65                      70                      75                      80

Ile Gly Gly Tyr Pro Phe Glu Met Gly Gly Thr Trp Val His Trp Gly
                         85                      90                      95

Gln Pro His Val Trp Arg Glu Ile Ser Arg Tyr Gln Met Arg Asn Glu
                        100                     105                     110

Leu Glu Ser Ser Phe Asp Phe Ser Arg Gly Val Asn His Phe Glu Leu
                        115                     120                     125

Arg Thr Asn Gln Gly Pro Ala Ile Met Ser His Lys Glu Glu Asp Glu
                        130                     135                     140

Leu Leu Ala Ala Ala Leu His Lys Phe Val Asp Val Asp Gly Asp Leu
145                     150                     155                     160

Gly Arg Arg Ala Val Pro Phe Pro His Asp Ser Phe His Val Pro Glu
                        165                     170                     175

Ala Arg Gln Tyr Asp Gln Met Ser Ala Lys Asp Arg Met Thr Gln Ile
                        180                     185                     190

Ala Asp Thr Val Ser Pro Arg Glu Arg Ala Ala Leu Glu Ser Phe Val
                        195                     200                     205

Leu Leu Cys Ser Gly Gly Thr Leu Ala Thr Thr Ser Phe Phe Glu Phe
210                     215                     220

Leu His Trp Trp Ala Leu Cys Gly Tyr Ser Tyr Gln Gly Cys Leu Asp
225                     230                     235                     240

Ala Leu Ile Ser Tyr Lys Phe Lys Arg Gly Gln Ser Ser Phe Ala Leu
                        245                     250                     255

Arg Phe Phe Arg Glu Ala Leu Ser Thr Gly Asn Leu Ser Tyr Ala Phe
                        260                     265                     270

Asn Ser Pro Ile Gln Ser Ile Asp Asp Gln Gly Ala Lys Val Val Val
                        275                     280                     285

Thr Thr Arg Glu Gly His Arg Tyr Ala Gly Ala Arg Leu Ile Ser Thr
                        290                     295                     300

Ile Pro Leu Asn Val Leu Asn Thr Val Thr Ile Ser Pro Pro Leu Gly
305                     310                     315                     320

Thr Gln Arg Thr Ala Ala Ala Asn Thr Gly His Val Asn Gln Cys Val
                        325                     330                     335

Lys Val His Ala Glu Ile Ala Ser Arg Asp Met Arg Ser Trp Thr Gly
                        340                     345                     350

Ile Ser Tyr Pro Phe Asn Lys Leu Cys Tyr Ala Ile Gly Asp Gly Thr
                        355                     360                     365

Thr Pro Ala Gly Asn Thr His Ile Val Cys Phe Gly Gly Ser His Asn
370                     375                     380

His Ile Gln Pro Glu Glu Asp Ile Lys Gln Thr Lys Thr Ala Val Glu
385                     390                     395                     400

Ser Leu Ser Pro Gly Asn Met Asp Ile Lys Arg Leu Val Phe His Asn
                        405                     410                     415

Trp Ser Lys Asp Glu Phe Ala Lys Gly Ala Trp Phe Phe Ser Pro Pro
                        420                     425                     430

Glu Met Leu Ser Thr Ser Leu Glu Ala Leu Arg Ser Arg His Gly Asn
                        435                     440                     445

Val Val Leu Ala Asn Ser Asp Trp Ala Leu Gly Trp Arg Ser Phe Ile
                        450                     455                     460

Asp Gly Ala Ile Glu Glu Gly Thr Arg Ala Ala Met Thr Val Val Glu
465                     470                     475                     480
```

```
Glu Leu Arg Pro Gln Pro Ala Val Arg Glu His Leu
            485                 490
```

<210> SEQ ID NO 35
<211> LENGTH: 1491
<212> TYPE: DNA
<213> ORGANISM: Artificial Sequence
<220> FEATURE:
<223> OTHER INFORMATION: variant monoamine oxidase

<400> SEQUENCE: 35

```
atgaccagcc gcgacggtta tcagtggacc ccggaaacgg gtctgaccca gggcgtaccg      60
tccctgggtg tcatttcgcc gccgactaac atcgaagata ccgataagga cgggccttgg     120
gatgtcattg tcattggggg cgggtattgt gggctgaccg caacccgtga tttaaccgtc     180
gcagggttca agacgctgct gctggaggcc cgtgatcgta ttggtggccg ctcctggagc     240
agtaatattg acggttaccc gtatgagatg ggtggcactt gggttcattg gcatgaatct     300
cacgtgtggc gtgaaatcac gcgttataaa atgcacaacg cgctgtctcc atcatttaac     360
tttcacgtg gcgtgaatca cttccaactg cgtaccaatc gcagaccag tacgtacatg     420
acgcacgaag cggaggatga actgctgcgt agcgcattgc ataaattcac caatgtcgac     480
ggcactaatg ccgtacagt gttgccgttc ccacatgata tgttttatgt gccggaattt     540
cgcaagtatg acgaaatgtc atattccgaa cgcattgacc agatccgcga cgaactgtct     600
ttgaacgaac gctctagttt agaggctttc attttattat gtagcggtgg caccctggaa     660
aactccagct ttggtgaatt tctgcattgg tgggcaatgt cggttacac gtatcagggc     720
tgtatggatt gtttaatctc ctataaattt aaggatggcc agagtgcgtt cgcgcgtcgc     780
ttctgggaag aagccgctgg cactggccgt ctgggttatg tctttggttg tccggtgcgt     840
tctgtggtgg atgaacgcga cgcagtacgt gttaccgcac gtgacggtcg cgaattcgca     900
gcgaaacgtt tggtttgcac gattccgctg aacgtattga gttctgttca gtttagccca     960
ccactgtccc cgcaacgcat ggccgctgcg aacattggcc atgttaacca gtgcgtcaaa    1020
gtgcatgcgg aagtcagttg tccggatatg cgttcatggt cgggtgtgtc ctatccgttc    1080
aacaaattag cctacgctat cggcgatggc acgacccag cgggtaatac gcatattgtg    1140
tgcttcgggg cgctcataaa tcatatccag ccggaagagg acgtggaagc aacgaagatg    1200
gccgttgaaa acatgtcgcc tgggaatatg gatatcaaac gtctggtctt ccacaactgg    1260
tgcaaggatg aatttgccaa aggcgcttgg ttcttcgccc ctccacagct gctgtcaaag    1320
agcctggatg aactgcgctg ccgtcacggt aatgtcctgt ttgcaaactc cgattgggcc    1380
ttaggttggc gtggttttat tgatggtgct atcgaggagg gcacccgcgc agcggttact    1440
gtaattgagg aactgcgtcc tgcgcctgcg gtgcgttccc acctgtaatg a            1491
```

<210> SEQ ID NO 36
<211> LENGTH: 495
<212> TYPE: PRT
<213> ORGANISM: Artificial Sequence
<220> FEATURE:
<223> OTHER INFORMATION: variant monoamine oxidase

<400> SEQUENCE: 36

```
Met Thr Ser Arg Asp Gly Tyr Gln Trp Thr Pro Glu Thr Gly Leu Thr
  1               5                  10                  15

Gln Gly Val Pro Ser Leu Gly Val Ile Ser Pro Pro Thr Asn Ile Glu
             20                  25                  30

Asp Thr Asp Lys Asp Gly Pro Trp Asp Val Ile Val Ile Gly Gly Gly
```

```
                 35                  40                  45
Tyr Cys Gly Leu Thr Ala Thr Arg Asp Leu Thr Val Ala Gly Phe Lys
 50                  55                  60
Thr Leu Leu Leu Glu Ala Arg Asp Arg Ile Gly Gly Arg Ser Trp Ser
 65                  70                  75                  80
Ser Asn Ile Asp Gly Tyr Pro Tyr Glu Met Gly Gly Thr Trp Val His
                 85                  90                  95
Trp His Glu Ser His Val Trp Arg Glu Ile Thr Arg Tyr Lys Met His
                100                 105                 110
Asn Ala Leu Ser Pro Ser Phe Asn Phe Ser Arg Gly Val Asn His Phe
            115                 120                 125
Gln Leu Arg Thr Asn Pro Gln Thr Ser Thr Tyr Met Thr His Glu Ala
            130                 135                 140
Glu Asp Glu Leu Leu Arg Ser Ala Leu His Lys Phe Thr Asn Val Asp
145                 150                 155                 160
Gly Thr Asn Gly Arg Thr Val Leu Pro Phe Pro His Asp Met Phe Tyr
                165                 170                 175
Val Pro Glu Phe Arg Lys Tyr Asp Glu Met Ser Tyr Ser Glu Arg Ile
            180                 185                 190
Asp Gln Ile Arg Asp Glu Leu Ser Leu Asn Glu Arg Ser Ser Leu Glu
            195                 200                 205
Ala Phe Ile Leu Leu Cys Ser Gly Gly Thr Leu Glu Asn Ser Ser Phe
            210                 215                 220
Gly Glu Phe Leu His Trp Trp Ala Met Ser Gly Tyr Thr Tyr Gln Gly
225                 230                 235                 240
Cys Met Asp Cys Leu Ile Ser Tyr Lys Phe Lys Asp Gly Gln Ser Ala
                245                 250                 255
Phe Ala Arg Arg Phe Trp Glu Glu Ala Ala Gly Thr Gly Arg Leu Gly
            260                 265                 270
Tyr Val Phe Gly Cys Pro Val Arg Ser Val Val Asp Gly Arg Asp Ala
            275                 280                 285
Val Arg Val Thr Ala Arg Asp Gly Arg Glu Phe Ala Ala Lys Arg Leu
            290                 295                 300
Val Cys Thr Ile Pro Leu Asn Val Leu Ser Ser Val Gln Phe Ser Pro
305                 310                 315                 320
Pro Leu Ser Pro Gln Arg Met Ala Ala Ala Asn Ile Gly His Val Asn
                325                 330                 335
Gln Cys Val Lys Val His Ala Glu Val Ser Cys Pro Asp Met Arg Ser
            340                 345                 350
Trp Ser Gly Val Ser Tyr Pro Phe Asn Lys Leu Ala Tyr Ala Ile Gly
            355                 360                 365
Asp Gly Thr Thr Pro Ala Gly Asn Thr His Ile Val Cys Phe Gly Gly
            370                 375                 380
Ala His Asn His Ile Gln Pro Glu Glu Asp Val Glu Ala Thr Lys Met
385                 390                 395                 400
Ala Val Glu Asn Met Ser Pro Gly Asn Met Asp Ile Lys Arg Leu Val
                405                 410                 415
Phe His Asn Trp Cys Lys Asp Glu Phe Ala Lys Gly Ala Trp Phe Phe
            420                 425                 430
Ala Pro Pro Gln Leu Leu Ser Lys Ser Leu Asp Glu Leu Arg Cys Arg
            435                 440                 445
His Gly Asn Val Leu Phe Ala Asn Ser Asp Trp Ala Leu Gly Trp Arg
            450                 455                 460
```

```
Gly Phe Ile Asp Gly Ala Ile Glu Glu Gly Thr Arg Ala Ala Val Thr
465                 470                 475                 480

Val Ile Glu Glu Leu Arg Pro Ala Pro Ala Val Arg Ser His Leu
                485                 490                 495
```

US 8,178,333 B2

BIOCATALYTIC PROCESSES FOR THE PREPARATION OF SUBSTANTIALLY STEREOMERICALLY PURE FUSED BICYCLIC PROLINE COMPOUNDS

1. CROSS REFERENCE TO RELATED APPLICATIONS

The present application claims priority of U.S. provisional application 61/075,243, filed Jun. 24, 2008, which is hereby incorporated by reference herein.

2. TECHNICAL FIELD

The present disclosure relates to substantially stereometrically pure fused bicyclic proline compounds of structural Formulae II to VII:

II(a)
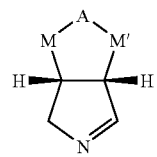

II(b)
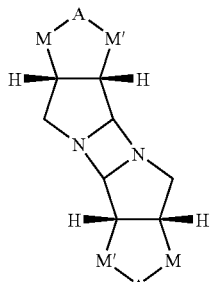

III(a)
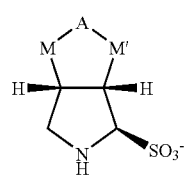

III(b)
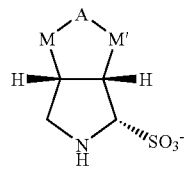

IV(a)
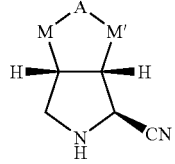

V
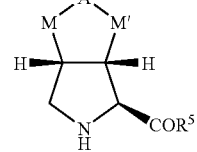

VI
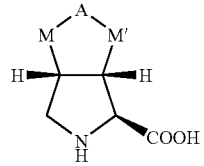

VII
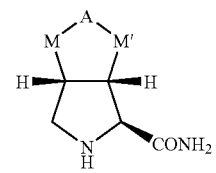

in which A, M, M', and $R^5$ are as described herein, to biocatalytic processes for their preparation, and to the biocatalytic enzymes used in those processes.

3. REFERENCE TO SEQUENCE LISTING, TABLE OR COMPUTER PROGRAM

The "Sequence Listing" concurrently submitted electronically under 37 C.F.R. §1.821 in a computer readable form (CRF) as file name CX2-020US1.txt is herein incorporated by reference. The electronic copy of the Sequence Listing was created on Jun. 23, 2009, with a file size of 110 Kbytes.

4. BACKGROUND

Bicyclic proline analogues are used in the discovery and development of peptidomimetic drugs. (A. Trabocchi et al. (2008) *Amino Acids* (2008) 34: 1-24). The hepatitis C virus protease inhibitors boceprevir (SCH 505034; ((1R,2S,5S)—N-(4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide) (Malcolm et al. (2006) *Antimicrob. Agents Chemother.* 50(3): 1013 20), and telaprevir (VX 950; N—((S)-1-cyclohexyl-2-((S)-1-((1S,3aR,6aS)-1-4R)-3-(2-(cyclopropylamino)-2-oxoacetyl)hexanoyl)hexahydrocyclopenta[c]pyrrol-2(1H)-yl)-3,3-dimethyl-1-oxobutan-2-ylamino)-2-oxoethyl)pyrazine-2-carboxamide) (Perni et al. (2006) *Antimicrob. Agents Chemother.* 50(3): 899 909).

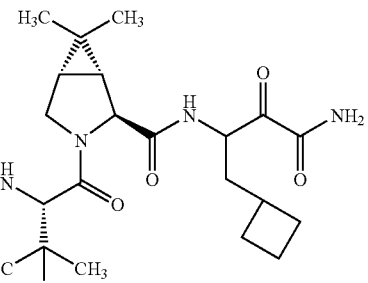

Boceprevir (SCH-505034)

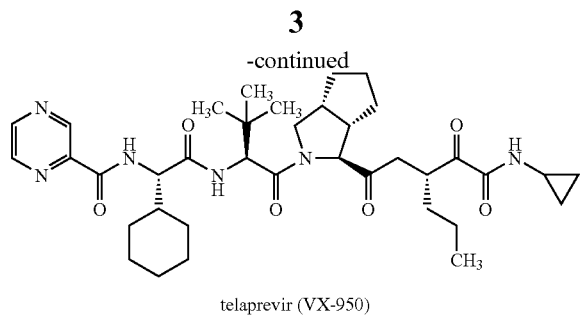

telaprevir (VX-950)

Boceprevir and telaprevir are prepared from esters of the cis-fused bicyclic L-proline analogues (1R,2S,5S)-6,6-dimethyl-3-azabicyclo[3.1.0]hexane-2-carboxylic acid and (1S,3aR,6aS)-octahydrocyclopenta[c]pyrrole-1-carboxylic acid, respectively, which are shown below:

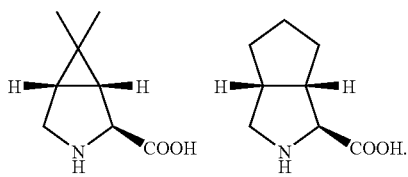

WO 2000/20824 and WO 2000/218369 describe numerous other hepatitis C protease inhibitors incorporating various fused bicyclic L-proline analogues corresponding to structural formula VI.

Although methods for the synthesis of such complex molecules using the methods and tools of organic chemistry have been reported, those syntheses generally are multi-step, intricate, expensive, inefficient, processes of low overall yield.

Wu et al. (WO 2007/075790) discloses the production of the methyl ester of the bicyclic proline analogue (1R,2S,5S)-6,6-dimethyl-3-azabicyclo[3.1.0]hexane-2-carboxylic acid from the corresponding symmetrical (achiral) bicyclic amine of structural formula (1R,5S)-6,6-dimethyl-3-azabicyclo[3.1.0]hexane, beginning with its oxidation to the corresponding racemic imine of structural formula

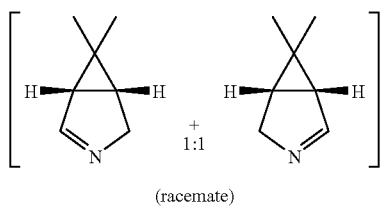

(racemate)

The racemic imine is subsequently reacted with cyanide to provide the racemic aminonitrile of the following structural formula

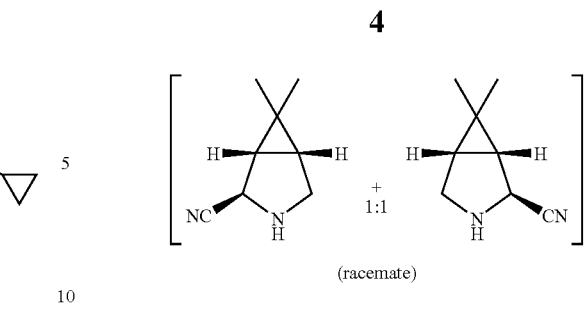

(racemate)

which is then reacted with acid and methanol to give the racemic amino acid methyl ester of the following structural formulae

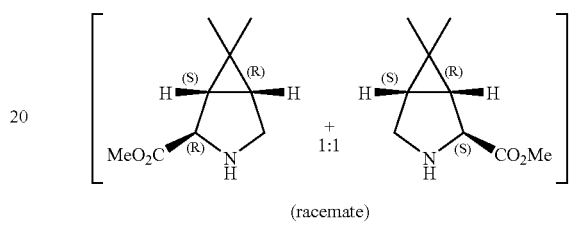

(racemate)

Finally, these (1R,2S,5S) (undesired) and (1S,2R,5R) (desired) stereoisomeric methyl esters are separated by diastereometric salt resolution, forming either the di-p-tolyl-D-tartaric acid salt with the former enantiomer or the di-p-tolyl-L-tartaric tartaric acid salt with the latter enantiomer.

Tanoury et al. (WO 2007/022459) disclose the synthesis of racemic (t-butoxycarbonyl)octahydrocyclopenta[c]pyrrole-1-carboxylic acid from the corresponding symmetrical (achiral) bicyclic amine by making the N-Boc derivative, and reacting it with the pyrophoric agent, sec-butyllithium in the presence of more than a stoichiometric amount of a bulky diamine chelate, then carbon dioxide, all at below −70° C. to produce the racemic N-Boc amino acids depicted below:

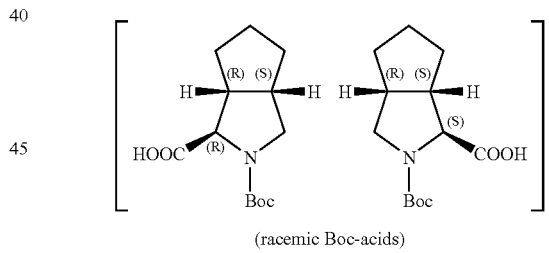

(racemic Boc-acids)

The (1R,2S,5S) (undesired) and (1S,2R,5R) (desired) stereoisomers of these racemic Boc-acids are then separated by diastereometric salt resolution using single enantiomer chiral bases such as S-1-aminotetralin.

Although the desired stereoisomer of the amino acid derivative is obtained by these methods, the resolution of a mixture of enantiomers of these bicyclic proline analogues inherently involves the waste of at least one half of all of the material (e.g. raw materials, reagents, solvents, catalysts) used in the production of the racemic mixture.

Additional methods for the chemical synthesis of amino acid (1S,3aR,6aS)-octahydrocyclopenta[c]pyrrole-1-carboxylic acid and its esters have also been reported involving (i) anodic oxidation of N-acetyl-3-azabicyclo[3.3.0]octane (EA 00090362), and (ii) a thiazolium ylide approach (*Letters in Drug Design & Discovery* (2005) 2(7): 497 502); *J. Org. Chem.* 1994, 59, 2773-8).

Methods to asymmetrically produce amino acids of structural formula (1S,3aR,6aS)-octahydrocyclopenta[c]pyrrole-1-carboxylic acid and esters thereof of structural Formula V from the corresponding symmetrical (achiral) bicyclic amines of structural formula I ((1R,5S)-6,6-dimethyl-3-azabicyclo[3.1.0]hexane) that avoid the formation of racemic mixtures, and the consequent need to separate the enantiomers can be more efficient, less wasteful, and more cost-effective than the resolution-based methods described above.

Monoamine oxidase enzymes have been used to resolve and deracemize racemic chiral amines via the stereospecific oxidation of one enantiomer to the corresponding imine using oxygen. Derivatives of the flavin dependent monoamine oxidase of *Aspergillus niger* (MAO N) (Shilling et al. (1995) *Biochim. Biophys. Acta.* 1243: 529 37) have been reported as useful, in combination with non specific chemical reducing agents, for the deracemization of (d/l) α methylbenzylamine to provide enantiomerically pure (93% ee) (d) α methylbenzylamine (Alexeeva et al. (2002) *Angew. Chem. Int. Ed.* 41: 3177-3180). Derivatives of the flavin dependent monoamine oxidase of *Aspergillus niger* were also used for deracemization of (R/S)-2-phenypyrrolidine to provide enantiomerically pure (98% ee) (R)-2-phenylpyrrolidine (Carr et al. (2005), *Chem Bio Chem* 6: 637 39; Gotor et al. "Enantioselective Enzymatic Desymmetrization in Organic Synthesis," *Chem. Rev.* (2005) 105: 313-54).

It is desirable therefore not only to provide substantially-enantiomerically pure chiral compounds, particularly chiral amine compounds that are useful as synthetic intermediates, but also to provide efficient, scalable biocatalytic processes for their asymmetric synthesis. It is also desirable, therefore, to provide enzymes useful in those biocatalytic processes.

5. SUMMARY

The present disclosure provides substantially stereometrically pure bicyclicimine compounds of structural Formula II(a) (and dimers thereof of structural Formula II(b)), which are particularly useful as novel intermediates in the synthesis of stereometrically defined therapeutic agents

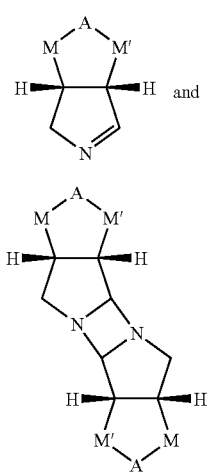

including salts and hydrates thereof, wherein A is O, $CR^1R^2$, —C=C—, or —$CH_2$—$CH_2$—, wherein $R^1$ and $R^2$ are each independently selected from —H, —COOH, —X, —$NH_2$, —$CH_2NHC(NH)NH_2$, —$CX_3$, —$CH_3$, —$CH_2CH_3$, and wherein X is selected from F, Cl, and Br. M and M' may both be present or may both be absent and when both M and M' are present M and M' are the same and are selected from O and $CR^3R^4$ wherein $R^3$ and $R^4$ are H, or $R^3$ or $R^4$ of M and $R^3$ or $R^4$ of M' form a methylene bridge, with the provisos that: (a) when M and M' are O, A is not O; and when A is O, M and M' are not O; (b) A can be —CH=CH— or —$CH_2$—$CH_2$— when M and M' are $CR^3R^4$; and (c) when M and M' are $CR^3R^4$ and have one or more stereocenters, the stereocenters of M and M' are of opposite stereochemistry.

The present disclosure further provides substantially enantiomerically pure aminosulfonate compounds according to structural Formula III(a) and structural Formula III(b), which are particularly useful as novel intermediates in the synthesis of enantiomerically defined therapeutic agents:

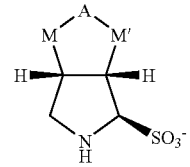

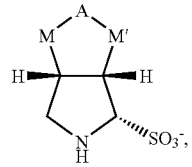

including salts and hydrates thereof in which A, M, and M', are as described above.

In addition, the present disclosure provides substantially enantiomerically pure aminonitrile compounds of structural Formula IV(a) which are useful as novel intermediates in the synthesis of stereometrically defined therapeutic agents. The substantially enantiomerically pure trans aminonitrile compounds of structural Formula IV(a) may also be provided as a mixture comprising substantially enantiomerically pure cis aminonitrile compounds of structural Formula IV(b)

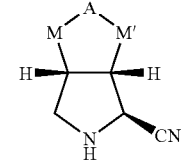

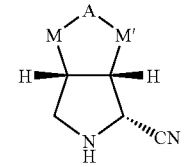

including salts and hydrates thereof in which A, M, and M', are as described above.

The present disclosure provides the optionally protected substantially enantiomerically pure compounds of structural Formula V, which are particularly useful as intermediates in the synthesis of enantiomerically defined therapeutic agents:

V

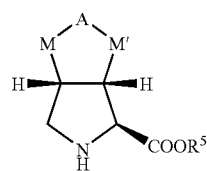

including salts and hydrates thereof in which A, M, and M', are as described above, and wherein $R^5$ is selected from the group consisting of a protecting group (e.g. benzyl or trimethylsilyl and the like), —$(C_1-C_2)$alkyl, —$(C_1-C_3)$alkyl, —$(C_1-C_4)$alkyl, and —$(C_1-C_6)$alkyl. In certain non-limiting embodiments $R^5$ is methyl, ethyl, or t-butyl.

The present disclosure also provides the optionally protected substantially enantiomerically pure compounds of structural Formula V(b) (corresponding to the cis enantiomer of the compound of structural Formula V):

V(b)

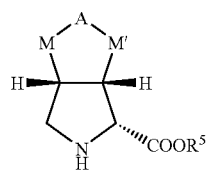

including salts and hydrates thereof in which A, M, and M', are as described above, and wherein $R^5$ is selected from the group consisting of a protecting group (e.g. benzyl or trimethylsilyl and the like), —$(C_1-C_2)$alkyl, —$(C_1-C_3)$alkyl, —$(C_1-C_4)$alkyl, and —$(C_1-C_6)$alkyl. In certain non-limiting embodiments $R^5$ is methyl, ethyl, or t-butyl.

The present disclosure also provides substantially enantiomerically pure carboxyl-substituted compounds of structural Formula VI, which are particularly useful as intermediates in the synthesis of enantiomerically defined therapeutic agents:

VI

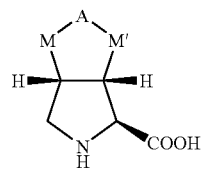

including salts and hydrates thereof in which A, M, and M', are as described above.

The present disclosure also provides the optionally protected substantially enantiomerically pure compounds of structural Formula VI(b) (corresponding to the cis enantiomer of the compound of structural Formula VI):

VI(b)

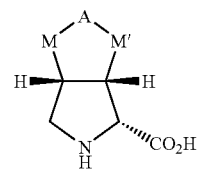

including salts and hydrates thereof in which A, M, and M', are as described above.

In addition, the present disclosure provides substantially enantiomerically pure compounds of structural Formula VII, which are particularly useful as intermediates in the synthesis of enantiomerically defined therapeutic agents

VII

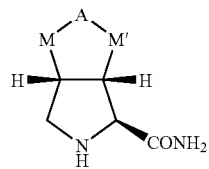

including salts and hydrates thereof in which A, M, and M', are as described above.

The present disclosure also provides the optionally protected substantially enantiomerically pure compounds of structural Formula VII(b) (corresponding to the cis enantiomer of the compound of structural Formula VII):

VII(b)

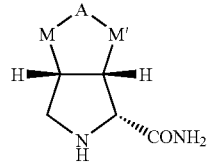

including salts and hydrates thereof in which A, M, and M', are as described above Therefore, in specific embodiments, the present disclosure provides the following fused bicyclic proline compounds useful as intermediates for the synthesis of one or more therapeutic agents, as well as biocatalytic processes for the synthesis of at least the following fused bicyclic proline compounds:

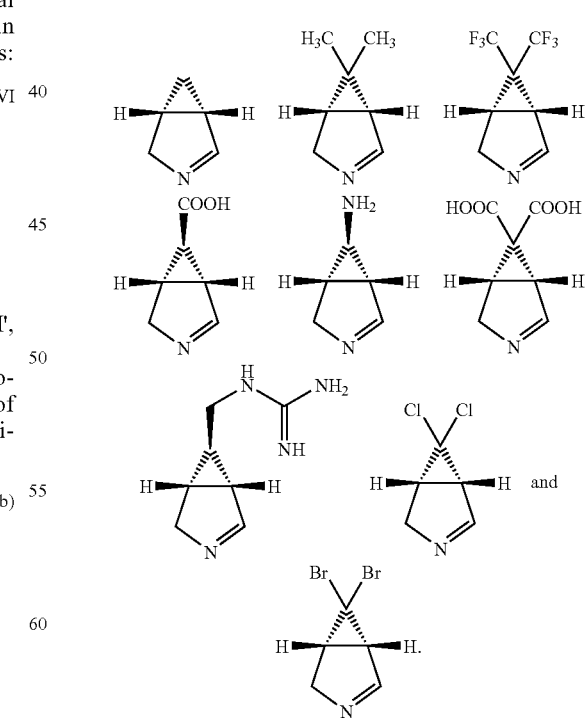

The present disclosure provides the following fused bicyclic proline compounds useful as intermediates for the synthesis of one or more therapeutic agents, as well as biocatalytic processes for the synthesis of at least the following fused bicyclic proline compounds:

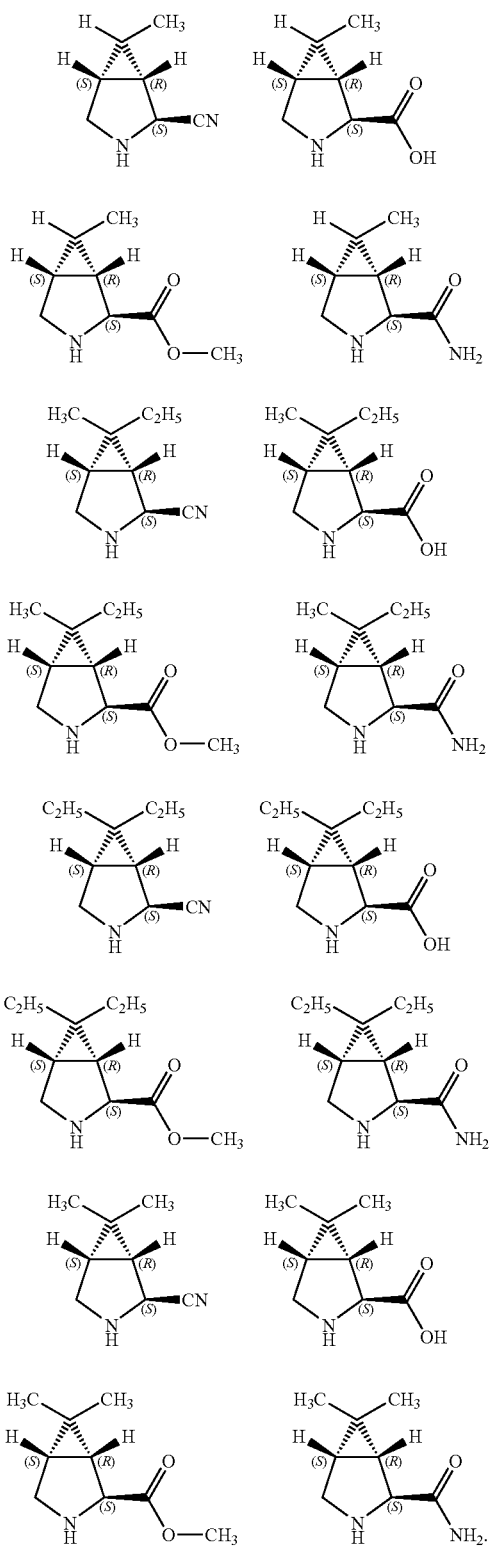

In other specific embodiments, the present disclosure provides the following compounds useful as intermediates for the synthesis of one or more therapeutic agents, as well as biocatalytic processes for the synthesis of these compounds:

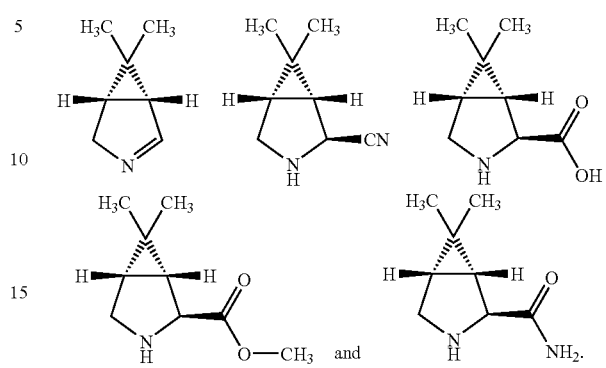

Thus, the present disclosure provides fused bicyclic proline compounds useful as intermediates for the synthesis of one or more therapeutic agents, as well as biocatalytic processes for the synthesis of these fused bicyclic proline compounds The present disclosure also provides methods for the biocatalytic synthesis of the substantially stereometrically pure compounds of structural Formulae II to VII. In one embodiment, the present disclosure provides a method of preparing a substantially stereometrically pure imine compound according to structural Formula II, including salts thereof, in which A, M, and M', are as described above. The method comprises contacting a symmetric (achiral) bicyclic amine compound according to structural Formula I

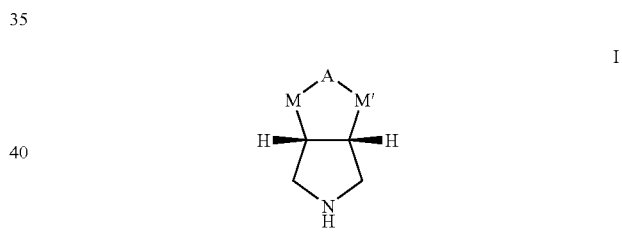

in which A, M, and M', are as described above, with oxygen and a monoamine oxidase enzyme in the presence of a cofactor under conditions in which the monoamine oxidase enzyme oxidizes an amine compound of structural Formula I to the corresponding imine compound of structural Formula II(a), the dimer thereof of Formula II(b), and mixtures thereof. In certain embodiments, the cofactor is selected from the group consisting of FAD, FMN, NADP, and NAD. In a particular embodiment the co-factor is FAD. In certain embodiments, the reaction mixture further comprises a component useful for facilitating the disproportionation of the hydrogen peroxide side product of the monoamine oxidase catalyzed reaction, as depicted in Scheme 2 (below) to molecular oxygen and water. In certain embodiments, that component is selected from among chemical agents, such as but not limited to Pd, and Fe and the like while in other embodiments, that component is an enzyme, such as the enzyme catalase. In a particular embodiment, the reaction mixture further comprises the enzyme catalase to catalyze the disproportionation reaction depicted in Scheme 2, hydrogen peroxide ($H_2O_2$) is broken down to molecular oxygen and water.

In certain embodiments, the monoamine oxidase capable of oxidizing an amine compound of structural Formula I to the corresponding imine compound of structural Formula II(a) is obtained from a species of *Aspergillus*. In particular embodiments, the monoamine oxidase is an *Aspergillus niger* monoamine oxidase, while in other embodiments, the monoamine oxidase is an *Aspergillus oryzae* monoamine oxidase. In either instance the monoamine oxidase may be purified from the corresponding *Aspergillus* species or may be isolated as a recombinant protein expressed in a heterologous host, such as, but not limited to *E. coli*.

In another embodiment, the monoamine oxidase capable of oxidizing an amine compound of structural Formula I to the corresponding imine compound of structural Formula II(a) comprises portions of more than one monoamine oxidase, e.g., a fusion or hybrid protein comprising an amino-terminal portion of the *Aspergillus niger* monoamine oxidase and a carboxy-terminal portion from the *Aspergillus oryzae* monoamine oxidase. In a specific embodiment, the monoamine oxidase is a 495 amino-acid protein (SEQ ID NO: 6) in which the amino terminal 314 amino acids correspond to the amino terminal 314 amino acids of *Aspergillus niger* (SEQ ID NO:2), and the carboxy-terminal 181 amino acids correspond to the carboxy-terminal 181 amino acids of *Aspergillus oryzae* (SEQ ID NO: 32). In other specific embodiments the monoamine oxidase is a derivative of the 495 amino acid protein of SEQ ID NO: 6 selected from SEQ ID NOS: 10, 12, 14, 16, 18, 20, and 36, each of which carries at least one amino acid substitution as compared to the amino acid sequence of SEQ ID NO:6.

In certain embodiments the monoamine oxidase capable of oxidizing an amine compound of structural Formula I to the corresponding imine compound of structural Formula II(a) is derived from the *Aspergillus* monoamine oxidase of SEQ ID NO:2 and has two or more amino acid substitutions as compared to the amino acid sequence of the *Aspergillus niger* monoamine oxidase of SEQ ID NO:2. In specific embodiments, the monoamine oxidase capable of oxidizing an amine compound of structural Formula I to the corresponding imine compound of structural Formula II comprises the amino acid sequence of SEQ ID NO:4 or SEQ ID NO:8.

In other embodiments, the monoamine oxidase capable of oxidizing an amine compound of structural Formula I to the corresponding imine compound of structural Formula II(a) is a fusion protein in which the amino-terminal amino acid sequence is derived from a first *Aspergillus* monoamine oxidase while the carboxy-terminal amino acid sequences is derived from that of another *Aspergillus* monoamine oxidase. In certain non-limiting embodiments, both the amino-terminal and the carboxyl-terminal portions of such a fusion protein could be independently selected from among selected from the group consisting of SEQ ID NO: 22, 24, 26, 28, 30, 32, and 34. In a particular embodiment, the amino terminal portion of the fusion protein is derived from the protein of SEQ ID NO: 32 while the carboxy terminal portion of the fusion protein is derived from the protein of SEQ ID NO: 2.

In certain embodiments, the present disclosure provides a method of preparing an aminosulfonate compound according to structural Formula III(a) or III(b), including salts and hydrates thereof, A, M, and M', are as described above. These methods comprise contacting a symmetrical bicyclic amine compound according to structural Formula I, A, M, and M', are as described above, with oxygen, a monoamine oxidase enzyme, and bisulfite under conditions which yield the aminosulfonate (the imine-bifulfite adduct) compound. In particular embodiments, the oxidation reaction mixture further comprises the enzyme catalase.

The present disclosure further provides a method of preparing a substantially stereometrically pure aminonitrile compound according to structural Formula IV(a), including salts and hydrates thereof, in which A, M, and M' are as described above. The method comprises contacting a symmetric bicyclic amine according to structural Formula I in which A, M, and M', are as described above, with oxygen, a monoamine oxidase enzyme, and bisulfite, followed by contact with cyanide under conditions which yield the aminonitrile compound. In particular embodiments, the oxidation reaction mixture further comprises the enzyme catalase.

The present disclosure further provides a method of preparing a substantially stereometrically pure aminonitrile compound according to structural Formula IV, including salts thereof, in which A, M, and M' are as described above. The method comprises contacting a symmetric bicyclic amine according to structural Formula I in which A, M, and M', are as described above, with oxygen and a monoamine oxidase enzyme to form the imine of structural formula II(a), a dimer thereof of structural formula II(b), or mixtures thereof, followed by contact with cyanide under conditions which yield the aminonitrile compound. In particular embodiments, the oxidation reaction mixture further comprises the enzyme catalase.

The present disclosure also provides a method of preparing a substantially stereometrically pure amino acid compound according to structural Formula VI, including salts thereof, in which A, M, and M' are as described above, starting from the compounds of structural formula II(a) (or the compounds of structural formula II(b)) or from the aminonitrile compounds of structural formula IV(a). The method comprises contacting a substantially stereometrically pure aminonitrile compound according to structural Formula IV, in which A, M, and M' are as described above, with an acid and water under conditions in which the aminonitrile compound is converted to the amino acid compound of structural Formula VI.

The disclosure further provides a method of preparing a substantially stereometrically pure amino acid compound according to structural Formula VI, including salts and co-crystals (e.g. $NH_4Cl$) thereof, in which A, M, and M' are as described above. The method comprises contacting a symmetrical (achiral) amine compound according to structural Formula I in which A, M, and M' are as described above, with oxygen and a monoamine oxidase enzyme, followed by contact with cyanide under conditions suitable to yield a substantially stereometrically pure aminonitrile compound according to structural Formula IV. In certain embodiments, the oxidation reaction mixture further comprises the enzyme catalase. The aminonitrile compound so formed is contacted with an acid and water under conditions in which the aminonitrile compound is converted to the amino acid compound of structural Formula VI.

The disclosure further provides a method of preparing a substantially stereometrically pure amino acid compound according to structural Formula VI, including salts and co-crystals (e.g. $NH_4Cl$) thereof, in which A, M, and M' are as described above. The method comprises contacting a symmetrical (achiral) amine compound according to structural Formula I, in which A, M, and M' are as described above, with oxygen, a monoamine oxidase enzyme and bisulfite, followed by contact with cyanide under conditions suitable to yield a substantially enantiomerically pure aminonitrile compound according to structural Formula IV. In certain embodiments, the oxidation reaction mixture further comprises the enzyme catalase. The aminonitrile compound so formed is contacted with an acid and water under conditions in which the aminonitrile compound is converted to the amino acid compound of structural Formula VI. In other embodiments, the aminonitrile compound so formed is contacted with an acid and alcohol under conditions in which the aminonitrile compound is converted to the amino ester compound of structural Formula V.

In addition, the present disclosure provides a method of preparing a substantially stereometrically pure protected amino acid compound according to structural Formula V, including salts thereof, in which A, M, M', and $R^5$ are as described above, using the novel compounds and methods, including the biocatalytic methods, disclosed herein. The method comprises contacting a substantially stereometrically pure aminonitrile compound according to structural Formula IV, in which A, M, and M' are as described above, with acid and an alcohol under conditions in which the aminonitrile compound is converted to the amino acid ester compound of structural Formula V.

The present disclosure also provides a method of preparing a substantially enantiomerically pure amino acid compound according to structural Formula VI, including salts thereof, in which A, M, and M' are as described above, using the novel compounds and methods, including the biocatalytic methods, disclosed herein. The method comprises contacting a substantially enantiomerically pure aminonitrile compound according to structural Formula IV, in which A, M, and M' are as described above, with acid (e.g. HCl) under conditions in which the aminonitrile compound is converted to the amino acid compound of structural Formula VI.

The disclosure further provides a method of preparing a substantially enantiomerically pure amino acid compound according to structural Formula VI, including salts and co-crystals (e.g. $NH_4Cl$) thereof, in which A, M, and M' are as described above. The method comprises contacting a amine compound according to structural Formula I, in which A, M, and M' are as described above, with oxygen and a monoamine oxidase enzyme and $NaHSO_3$, followed by contact with cyanide under conditions suitable to yield a substantially enantiomericaly pure aminonitrile compound according to structural Formula IV. In certain embodiments, the reaction mixture further comprises the enzyme catalase. The aminonitrile compound so formed is contacted with HCl under conditions in which the aminonitrile compound is converted to the amino acid compound of structural Formula VI.

In addition, the present disclosure provides a method of preparing a substantially enantiomerically pure amino acid ester compound according to structural Formula V, including salts thereof, in which A, M, M' and $R^5$ are as described above using the novel compounds and methods, including the biocatalytic methods, disclosed herein. The method comprises contacting a substantially enantiomerically pure aminonitrile compound according to structural Formula IV, in which A, M, M' are as described above, with acid (e.g. HCl) and an alcohol under conditions in which the aminonitrile compound is converted to the amino ester compound of structural Formula V.

The present disclosure further provides a method of preparing a substantially enantiomerically pure amino amide compound according to structural Formula VII, including salts thereof, in which A, M, and M', are as described above. The method comprises contacting an amine compound according to structural Formula I, wherein A, M, M' are as described, with oxygen and a monoamine oxidase enzyme and, optionally a catalase enzyme and bisulfite, followed by contact with cyanide under conditions suitable to yield a substantially enantiomerically pure aminonitrile compound according to structural Formula IV, in which A, M, M' are as described above, and thereafter contacting the aminonitrile compound with HCl and water under conditions in which the aminonitrile compound, can be converted to the amino acid amide compound of structural Formula VII.

The monoamine oxidases of the present disclosure, which are capable of oxidizing an amine compound of structural Formula I to the corresponding imine compound of structural Formula II, have one or more amino acid substitutions as compared to the amino acid sequence of SEQ ID NO: 2, SEQ ID NO:32, and SEQ ID NO: 6. Such amino acid substitutions provide the monoamine oxidase with one or more improved properties including an increase in enzyme activity, stereoselectivity, thermostability, solvent stability, reduced product inhibition, reduced substrate inhibition, or reduced sensitivity to reaction co-products. Such amino acid substitutions may also improve the solubility, stability, and expression level of the monoamine oxidase in a host cell, e.g., as a recombinantly-expressed protein in a heterologous host cell, such as but not limited to an *E. coli* host cell.

The present disclosure also provides polynucleotides encoding such monoamine oxidases and methods for using the polypeptides in the biocatalytic processes disclosed.

In some embodiments, the monoamine oxidases disclosed in the present specification, are improved as compared to the enzyme of SEQ ID NO:2, SEQ ID NO:32 or SEQ ID NO:6 with respect to their rate of enzymatic activity, i.e., their rate of converting an amine compound of structural Formula I to the corresponding imine compound of structural Formula II. In some embodiments, the monoamine oxidases disclosed are capable of converting the substrate to the product at a rate that is at least 1.5-times, 2-times, 3-times, 4-times, 5-times, 10-times, 25-times, 50-times, 100-times, or more than 100-times the rate exhibited by the monoamine oxidase of SEQ ID NO:2, SEQ ID NO:32 or SEQ ID NO:6. Exemplary polypeptides with such properties include, but are not limited to, polypeptides which comprise an amino acid sequence corresponding to SEQ ID NO: 4, 8, 10, 12, 14, 16, 18, 20, and 36.

In some embodiments, the monoamine oxidases disclosed herein are capable of converting an amine compound of structural Formula I to the corresponding imine compound of structural Formula II with a percent enantiomeric excess of at least about 95%. Exemplary polypeptides with such properties include, but are not limited to, polypeptides which comprise an amino acid sequence corresponding to SEQ ID NO: 4, 8, 10, 12, 14, 16, 18, 20, and 36.

In some embodiments, an improved monoamine oxidase of the disclosure is based on the sequence formulas of SEQ ID NO: 4, 8, 10, 12, 14, 16, 18 and 20 and can comprise an amino acid sequence that is at least about 85%, 86%, 87%, 88%, 89%, 90%, 91%, 92%, 93%, 94%, 95%, 96%, 97%, 98%, or 99% identical thereto. These differences can be one or more amino acid insertions, deletions, substitutions, or any combination of such changes. In some embodiments, the amino acid sequence differences can comprise non-conservative, conservative, as well as a combination of non-conservative and conservative amino acid substitutions. Various amino acid residue positions where such changes can be made are described herein.

In some embodiments, an improved monoamine oxidase of the disclosure comprises an amino acid sequence in which the amino acid corresponding to residue 99 of SEQ ID NO: 2 and SEQ ID NO. 6, and residue 97 of SEQ ID NO: 32, glutamine, is substituted with an acidic amino acid, i.e., aspartic acid or glutamic acid. In a particular embodiment, that glutamine residue is replaced with a glutamic acid residue.

In some embodiments, an improved monoamine oxidase of the disclosure comprises an amino acid sequence in which the amino acid corresponding to residue 365 of SEQ ID NO: 2, and SEQ ID NO. 6, and residue 363 of SEQ ID NO: 32, tyrosine, is conservatively substituted with a different aromatic amino acid, i.e., phenylalanine or tryptophan. In a particular embodiment, that tyrosine residue is replaced with a tryptophan residue.

In some embodiments, an improved monoamine oxidase of the disclosure comprises an amino acid sequence in which the amino acid corresponding to residue 382 of SEQ ID NO: 2 and SEQ ID NO. 6, and residue 380 of SEQ ID NO: 32, phenylalanine, is substituted with a nonpolar amino acid, i.e., valine, isoleucine, alanine, glycine, methionine, or leucine. In a particular embodiment, that phenylalanine residue is replaced with a leucine residue.

In some embodiments, an improved monoamine oxidase of the disclosure comprises an amino acid sequence in which the amino acid corresponding to residue 465 of SEQ ID NO: 2 and SEQ ID NO. 6, and residue 463 of SEQ ID NO: 32, serine, is substituted with a nonpolar amino acid, i.e., valine, isoleucine, alanine, methionine, leucine, or glycine. In a particular embodiment, that serine residue is replaced with a glycine residue.

In other embodiments, an improved monoamine oxidase of the disclosure comprises an amino acid sequence in which the amino acid corresponding to residue 135 of SEQ ID NO: 2 and SEQ ID NO. 6, threonine, is conservatively substituted with another polar amino acid, i.e., serine, glutamine, or asparagine. In a particular embodiment, that threonine residue is replaced with a glutamine residue.

In some embodiments, an improved monoamine oxidase of the disclosure comprises an amino acid sequence in which the amino acid corresponding to residue 284 of SEQ ID NO: 2 and SEQ ID NO. 6, asparagine, is substituted with an acidic amino acid, i.e., aspartic acid or glutamic acid. In a particular embodiment, that asparagine residue is replaced with a glutamic acid residue.

In some embodiments, an improved monoamine oxidase of the disclosure comprises an amino acid sequence in which the amino acid corresponding to residue 289 of SEQ ID NO: 2 is conservatively substituted with another nonpolar amino acid, i.e., glycine, valine, leucine, isoleucine, or methionine. In a particular embodiment, that alanine residue is replaced with a valine residue.

In other embodiments, an improved monoamine oxidase of the disclosure comprises an amino acid sequence in which the amino acid corresponding to residue 384 of SEQ ID NO: 2, lysine, is conservatively substituted with another polar amino acid, i.e., serine, threonine, or glutamine. In a particular embodiment, that lysine residue is replaced with a glutamine residue.

In some embodiments, an improved monoamine oxidase of the disclosure is a monoamine oxidase that is a homologue of the monoamine oxidase of *Aspergillus niger* (SEQ ID NO:2) or a homologue of the monoamine oxidase of *Aspergillus oryzae* (SEQ ID NO:44) and that carries one or more of the amino acid substitutions corresponding to those disclosed herein. Illustrative homologues include the monoamine oxidases SEQ ID NO: 22, SEQ ID NO: 24, SEQ ID NO: 26, SEQ ID NO: 28, SEQ ID NO: 30, SEQ ID NO: 32, and SEQ ID NO: 34. In other embodiments, an improved monoamine oxidase of the disclosure is a monoamine oxidase selected from the enzymes of SEQ ID NO: 22, SEQ ID NO: 24, SEQ ID NO: 26, SEQ ID NO: 28, SEQ ID NO: 30, SEQ ID NO: 32, and SEQ ID NO: 34, and that carry one or more of the amino acid substitutions corresponding to those disclosed herein.

In another aspect, the present disclosure provides polynucleotides encoding the engineered monoamine oxidases described herein or polynucleotides that hybridize to such polynucleotides under highly stringent conditions. The polynucleotide can include promoters and other regulatory elements useful for expression of the encoded engineered monoamine oxidase, and can utilize codons optimized for specific desired expression systems. Exemplary polynucleotides include, but are not limited to, SEQ ID NO: 1, 5, 7, 9, 11, 13, 15, 17, 19, 31, and 35.

In another aspect, the present disclosure provides host cells comprising the polynucleotides and/or expression vectors described herein. The host cells may be cells of an *Aspergillus* species, e.g. *Aspergillus niger*, *Aspergillus oryzae*, or *Aspergillus nidulans*, or they may be a different organism, e.g. *E. coli* or *S. cerevisiae*. The host cells can be used for the expression and isolation of the engineered monoamine oxidase enzymes described herein, or, alternatively, they can be used directly for the conversion of the substrate to the stereoisomeric product.

Whether carrying out the method with whole cells, cell extracts or purified monoamine oxidases, a single monoamine oxidase may be used or, alternatively, mixtures of two or more monoamine oxidases may be used.

The monoamine oxidase enzymes described herein are capable of catalyzing the oxidation of a compound of structural Formula) to a compound of structural formula II(a):

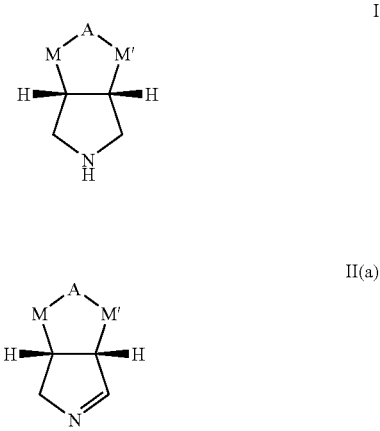

In a particular embodiment, the monoamine oxidase enzymes described herein are capable of catalyzing the oxidation of (1R,5S)-6,6-dimethyl-3-azabicyclo[3.1.0]hexane, compound (1) to (1R,5S)-6,6-dimethyl-3-azabicyclo[3.1.0]hex-2-ene, compound (2):

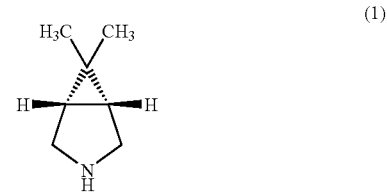

(2)

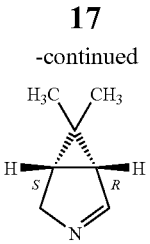

In another particular embodiment, the monoamine oxidase enzymes described herein are capable of catalyzing the oxidation of (3aR,6aS)-octahydrocyclopenta[c]pyrrole, compound (3) to (3aS,6aR)-1,3a,4,5,6,6a-hexahydrocyclopenta[c]pyrrole, compound (4):

(3)

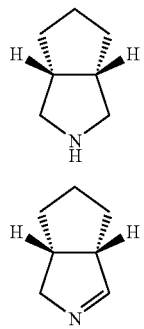

(4)

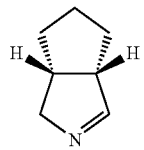

In some embodiments of the method for oxidizing a compound of structural Formula I to a compound of structural Formula II(a), the substrate is oxidized to the product in greater than about 99% stereometric excess, wherein the monoamine oxidase comprises a sequence that corresponds to SEQ ID NO: 4, 6, 8, 10, 12, 14, 16, 18, 20, or 36.

In some embodiments of this method for oxidizing a compound of structural Formula I to a compound of structural Formula II(a), at least about 10-20% of 1-100 g/L substrate is converted to the product in less than about 24 hours with about 1-10 g/L of the polypeptide, wherein the polypeptide comprises an amino acid sequence corresponding to SEQ ID NO: 4, 6, 8, 10, 12, 14 16, 18, 20, or 36.

In some embodiments of this method for reducing the substrate to the product, at least about 95% of the substrate is converted to the product in less than about 24 hours when carried out with greater than about 25-50 g/L of substrate and less than about 1-5 g/L of the polypeptide, wherein the polypeptide comprises an amino acid sequence corresponding to SEQ ID NO: 4, 6, 8, 10, 12, 14 16, 18, 20, or 36.

6. DETAILED DESCRIPTION

6.1 Fused Bicyclic Proline Compounds of the Disclosure 6.1.1 Fused Bicyclic Proline Compounds of Formula II(a) and (b)

The present disclosure provides substantially enantiomerically pure fused bicyclic proline compounds of structural Formula II(a) and the dimers thereof, compounds of structural Formula II (b), and to mixtures thereof:

II(a)

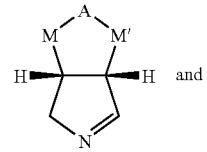

and

II(b)

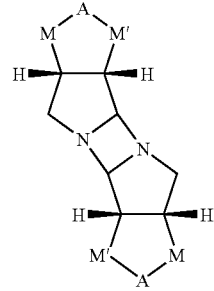

including salts and hydrates thereof, wherein A is O, $CR^1R^2$, —C=C—, or —$CH_2$—$CH_2$—, wherein $R^1$ and $R^2$ are each independently selected from —H, —COOH, —X, —$NH_2$, —$CH_2NHC(NH)NH_2$, —$CX_3$, —$CH_3$, —$CH_2CH_3$, and wherein X is selected from F, Cl, and Br. M and M' may both be present or may both be absent and when both M and M' are present M and M' are the same and are selected from O and $CR^3R^4$ wherein $R^3$ and $R^4$ are H, or $R^3$ or $R^4$ of M and $R^3$ or $R^4$ of M' form a methylene bridge, with the provisos that: (a) when M and M' are O, A is not O; and when A is O, M and M' are not O; (b) A can be —CH=CH— or —$CH_2$—$CH_2$— when M and M' are $CR^3R^4$; and (c) when M and M' are $CR^3R^4$ and have one or more stereocenters, the stereocenters of M and M' are of opposite stereochemistry.

In one embodiment, A is —$CH_2$—.
In another embodiment A is —$CH(CH_3)$—.
In another embodiment A is —$C(CH_3)_2$—.
In another embodiment A is —$CH(CH_2CH_3)$—.
In another embodiment A is —$C(CH_2CH_3)_2$—.
In another embodiment A is —$C(CH_2CH_3)(CH_3)$—.

In one embodiment M and M' are absent and A is selected from the group consisting of —$CH_2$—, —$CH(CH_3)$—, —$CH(C_2H_5)$—, —$C(CH_3)_2$—, —$C(C_2H_5)_2$—, —$CF_2$—, —$CCl_2$—, —$CBr_2$—, —$C(CF_3)_2$—, —$CH(COOH)$—, —$C(COOH)_2$—, —$CH(NH_2)$—, and —$CH(CH_2NHC(NH)NH_2)$—.

In another embodiment M and M' are absent and A is selected from the group consisting of —$CH_2$—, —$C(CH_3)_2$—, —$C(CH_3)_2$—, and —$C(C_2H_5)_2$—.

In another embodiment, M and M' are —$CH_2$— and A is selected from the group consisting of —O—, —$CH_2$—, —$C(CH_3)_2$—, —$CH(CH_3)$—, —$C(C_2H_5)_2$—, —$CH(C_2H_5)$—, —$CF_2$—, —$CCl_2$—, —$CBr_2$—, —$C(CF_3)_2$—, —$CH(COOH)$—, —$C(COOH)_2$—, —$CH(NH_2)$—, and —$C(H_2)NHC(NH)NH_2$—.

In a further embodiment, M and M' are —$CH_2$— and A is selected from the group consisting of —O—, —$CH_2$—, and —$C(CH_3)_2$—.

In a still further embodiment, M and M' are —O— and A is selected from the group consisting of —$CH_2$—, —$CH(CH_3)$—, —$CH(C_2H_5)$—, —$C(CH_3)_2$—, —$C(C_2H_5)_2$—, —$CF_2$—, —$CCl_2$—, —$CBr_2$—, —$C(CF_3)_2$—, —$CH(COOH)$—, —$C(COOH)_2$—, —$CH(NH_2)$—, and —$CH(CH_2NHC(NH)NH_2)$—.

In another embodiment, M and M' are —O— and A is selected from the group consisting of —$CH_2$—, —$C(CH_3)_2$—, and —$C(C_2H_5)_2$—.

Many imines of pyrrolidine compounds (e.g., 3,4-dihydro-2H-pyrrole) are known to form a thermodynamically favored trimer due to ring strain in addition to, or instead of a dimer. Accordingly, in certain embodiments any of the above compounds of Formula II(a) can also exist in a trimer form having structural Formula II(c)

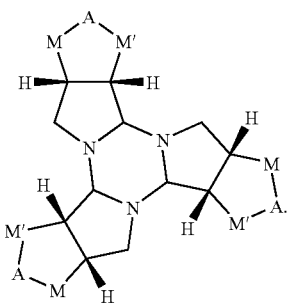

In certain embodiments, the disclosure provides trimer of compounds of Formula II(a), e.g., compounds of Formula II(c), and mixtures thereof with compounds of Formula II(a) and/or Formula II(b).

6.1.2 Aminosulfonate of Structural Formula III

The present disclosure further provides substantially enantiomerically pure aminosulfonate compounds of structural Formula III(a) and (b):

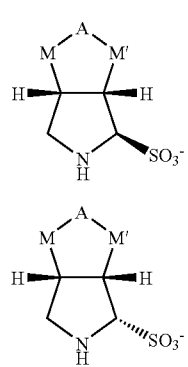

including salts, hydrates, and mixtures thereof, wherein A is O, $CR^1R^2$, —C=C—, or —$CH_2$—$CH_2$—, wherein $R^1$ and $R^2$ are each independently selected from —H, —COOH, —X, —$NH_2$, —$CH_2NHC(NH)NH_2$, —$CX_3$, —$CH_3$, —$CH_2CH_3$, and wherein X is selected from F, Cl, and Br. M and M' may both be present or may both be absent and when both M and M' are present M and M' are the same and are selected from O and $CR^3R^4$ wherein $R^3$ and $R^4$ are H, or $R^3$ or $R^4$ of M and $R^3$ or $R^4$ of M' form a methylene bridge, with the provisos that: (a) when M and M' are O, A is not O; and when A is O, M and M' are not O; (b) A can be CH=CH— or $CH_2$—$CH_2$— when M and M' are $CR^3R^4$; and (c) when M and M' are $CR^3R^4$ and have one or more stereocenters, the stereocenters of M and M' are of opposite stereochemistry.

In one embodiment, A is $CH_2$—.
In another embodiment A is $CH(CH_3)$—.
In another embodiment A is —$C(CH_3)_2$—.
In another embodiment A is —$CH(CH_2CH_3)$—.
In another embodiment A is —$C(CH_2CH_3)_2$—.
In another embodiment A is —$C(CH_2CH_3)(CH_3)$—.

In one embodiment M and M' are absent and A is selected from the group consisting of —$CH_2$—, —$CH(CH_3)$—, —$CH(C_2H_5)$—, —$C(CH_3)_2$—, —$C(C_2H_5)_2$—, —$CF_2$—, —$CCl_2$—, —$CBr_2$—, —$C(CF_3)_2$—, —$CH(COOH)$—, —$C(COOH)_2$—, —$CH(NH_2)$—, and —$CH(CH_2NHC(NH)NH_2)$—.

In another embodiment M and M' are absent and A is selected from the group consisting of —$CH_2$—, —$C(CH_3)_2$—, —$C(CH_3)_2$—, and —$C(C_2H_5)_2$—.

In another embodiment, M and M' are —$CH_2$— and A is selected from the group consisting of —O—, —$CH_2$—, —$C(CH_3)_2$—, —$CH(CH_3)$—, —$C(C_2H_5)_2$—, —$CH(C_2H_5)$—, —$CF_2$—, —$CCl_2$—, —$CBr_2$—, —$C(CF_3)_2$—, —$CH(COOH)$—, —$C(COOH)_2$—, —$CH(NH_2)$—, and —$C(H_2)NHC(NH)NH_2$—.

In a further embodiment, M and M' are —$CH_2$— and A is selected from the group consisting of —O—, —$CH_2$—, and —$C(CH_3)_2$—.

In a still further embodiment, M and M' are —O— and A is selected from the group consisting of —$CH_2$—, —$CH(CH_3)$—, —$CH(C_2H_5)$—, —$C(CH_3)_2$—, —$C(C_2H_5)_2$—, —$CF_2$—, —$CCl_2$—, —$CBr_2$—, —$C(CF_3)_2$—, —$CH(COOH)$—, —$C(COOH)_2$—, —$CH(NH_2)$—, and —$CH(CH_2NHC(NH)NH_2)$—.

In another embodiment, M and M' are —O— and A is selected from the group consisting of —$CH_2$—, —$C(CH_3)_2$—, and —$C(C_2H_5)_2$—.

6.1.3 Aminonitrile Compounds of Structural Formula IV

In addition, the present disclosure provides substantially enantiomerically pure aminonitrile compounds of structural Formula IV(a) and (b)

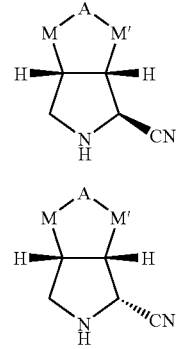

including salts, hydrates, and mixtures thereof, wherein A is O, $CR^1R^2$, —C=C—, or —$CH_2$—$CH_2$—, wherein $R^1$ and $R^2$ are each independently selected from —H, —COOH, —X, —$NH_2$, —$CH_2NHC(NH)NH_2$, —$CX_3$, —$CH_3$, —$CH_2CH_3$, and wherein X is selected from F, Cl, and Br. M and M' may both be present or may both be absent and when both M and M' are present M and M' are the same and are selected from O and $CR^3R^4$ wherein $R^3$ and $R^4$ are H, or $R^3$ or $R^4$ of M and $R^3$ or $R^4$ of M' form a methylene bridge, with the provisos that: (a) when M and M' are O, A is not O; and when A is O, M and M' are not O; (b) A can be —CH=CH— or —$CH_2$—$CH_2$— when M and M' are $CR^3R^4$; and (c) when M and M' are $CR^3R^4$ and have one or more stereocenters, the stereocenters of M and M' are of opposite stereochemistry.

In one embodiment, A is —$CH_2$—.
In another embodiment A is —$CH(CH_3)$—.
In another embodiment A is —$C(CH_3)_2$—.
In another embodiment A is —$CH(CH_2CH_3)$—.

In another embodiment A is —C(CH₂CH₃)₂—.
In another embodiment A is —C(CH₂CH₃)(CH₃)—.
In one embodiment M and M' are absent and A is selected from the group consisting of —CH₂—, —CH(CH₃)—, —CH(C₂H₅)—, —C(CH₃)₂—, —C(C₂H₅)₂—, —CF₂—, —CCl₂—, —CBr₂—, —C(CF₃)₂—, —CH(COOH)—, —C(COOH)₂—, —CH(NH₂)—, and —CH(CH₂NHC(NH)NH₂)—.

In another embodiment M and M' are absent and A is selected from the group consisting of —CH₂—, —C(CH₃)₂—, —C(CH₃)₂—, and —C(C₂H₅)₂—.

In another embodiment, M and M' are —CH₂— and A is selected from the group consisting of —O—, —CH₂—, —C(CH₃)₂—, —CH(CH₃)—, —C(C₂H₅)₂—, —CH(C₂H₅)—, —CF₂—, —CCl₂—, —CBr₂—, —C(CF₃)₂—, —CH(COOH)—, —C(COOH)₂—, —CH(NH₂)—, and —C(H₂)NHC(NH)NH₂—.

In a further embodiment, M and M' are —CH₂— and A is selected from the group consisting of —O—, —CH₂—, and —C(CH₃)₂—.

6.1.4 Fused Bicyclic Proline Compounds of Structural Formula V

The present disclosure provides fused bicyclic proline compounds of structural Formula V:

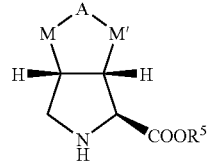

V including salts and hydrates thereof in which A, M, and M', wherein R⁵ is selected from the group consisting of a protecting group (e.g. benzyl or trimethylsilyl and the like), —(C₁-C₂)alkyl, —(C₁-C₃)alkyl, —(C₁-C₄)alkyl, and —(C₁-C₆)alkyl. In certain non-limiting embodiments R⁵ is methyl, ethyl, or t-butyl including salts and hydrates thereof, wherein A is O, CR¹R², —C=C—, or —CH₂—CH₂—, wherein R¹ and R² are each independently selected from —H, —COOH, —X, —NH₂, —CH₂NHC(NH)NH₂, —CX₃, —CH₃, —CH₂CH₃, and wherein X is selected from F, Cl, and Br. M and M' may both be present or may both be absent and when both M and M' are present M and M' are the same and are selected from O and CR³R⁴ wherein R³ and R⁴ are H, or R³ or R⁴ of M and R³ or R⁴ of M' form a methylene bridge, with the provisos that: (a) when M and M' are O, A is not O; and when A is O, M and M' are not O; (b) A can be —CH=CH— or —CH₂—CH₂— when M and M' are CR³R⁴; and (c) when M and M' are CR³R⁴ and have one or more stereocenters, the stereocenters of M and M' are of opposite stereochemistry.

In one embodiment, A is —CH₂—.
In another embodiment A is —CH(CH₃)—.
In another embodiment A is —C(CH₃)₂—.
In another embodiment A is —CH(CH₂CH₃)—.
In another embodiment A is —C(CH₂CH₃)₂—.
In another embodiment A is —C(CH₂CH₃)(CH₃)—.
In one embodiment M and M' are absent and A is selected from the group consisting of —CH₂—, —CH(CH₃)—, —CH(C₂H₅)—, —C(CH₃)₂—, —C(C₂H₅)₂—, —CF₂—, —CCl₂—, —CBr₂—, —C(CF₃)₂—, —CH(COOH)—, —C(COOH)₂—, —CH(NH₂)—, and —CH(CH₂NHC(NH)NH₂)—.

In another embodiment M and M' are absent and A is selected from the group consisting of —CH₂—, —C(CH₃)₂—, —C(CH₃)₂—, and —C(C₂H₅)₂—.

In another embodiment, M and M' are —CH₂— and A is selected from the group consisting of —O—, —CH₂—, —C(CH₃)₂—, —CH(CH₃)—, —C(C₂H₅)₂—, —CH(C₂H₅)—, —CF₂—, —CCl₂—, —CBr₂—, —C(CF₃)₂—, —CH(COOH)—, —C(COOH)₂—, —CH(NH₂)—, and —C(H₂)NHC(NH)NH₂—.

In a further embodiment, M and M' are —CH₂— and A is selected from the group consisting of —O—, —CH₂—, and —C(CH₃)₂—.

In one embodiment, R⁵ is benzyl.
In one embodiment, R⁵ is trimethylsilyl.
In another embodiment, R⁵ is methyl.
In a further embodiment, R⁵ is ethyl.
In another embodiment, R⁵ is t-butyl.

6.1.5 Fused Bicyclic Proline Compounds of Structural Formula VI

The present disclosure also provides substantially enantiomerically pure compounds according to structural Formula VI:

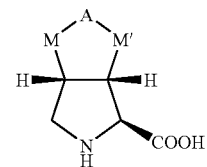

VI including salts and hydrates thereof, wherein A is O, CR¹R², —C=C—, or —CH₂—CH₂—, wherein R¹ and R² are each independently selected from —H, —COOH, —X, —NH₂, —CH₂NHC(NH)NH₂, —CX₃, —CH₃, —CH₂CH₃, and wherein X is selected from F, Cl, and Br. M and M' may both be present or may both be absent and when both M and M' are present M and M' are the same and are selected from O and CR³R⁴ wherein R³ and R⁴ are H, or R³ or R⁴ of M and R³ or R⁴ of M' form a methylene bridge, with the provisos that: (a) when M and M' are O, A is not O; and when A is O, M and M' are not O; (b) A can be —CH=CH— or —CH₂—CH₂— when M and M' are CR³R⁴; and (c) when M and M' are CR³R⁴ and have one or more stereocenters, the stereocenters of M and M' are of opposite stereochemistry.

In one embodiment, A is —CH₂—.
In another embodiment A is —CH(CH₃)—.
In another embodiment A is —C(CH₃)₂—.
In another embodiment A is —CH(CH₂CH₃)—.
In another embodiment A is —C(CH₂CH₃)₂—.
In another embodiment A is —C(CH₂CH₃)(CH₃)—.
In one embodiment M and M' are absent and A is selected from the group consisting of —CH₂—, —CH(CH₃)—, —CH(C₂H₅)—, —C(CH₃)₂—, —C(C₂H₅)₂—, —CF₂—, —CCl₂—, —CBr₂—, —C(CF₃)₂—, —CH(COOH)—, —C(COOH)₂—, —CH(NH₂)—, and —CH(CH₂NHC(NH)NH₂)—.

In another embodiment M and M' are absent and A is selected from the group consisting of —CH₂—, —C(CH₃)₂—, —C(CH₃)₂—, and —C(C₂H₅)₂—.

In another embodiment, M and M' are —CH₂— and A is selected from the group consisting of —O—, —CH₂—, —C(CH₃)₂—, —CH(CH₃)—, —C(C₂H₅)₂—, —CH (C₂H₅)—, —CF₂—, —CCl₂—, —CBr₂—, —C(CF₃)₂—, —CH(COOH)—, —C(COOH)₂—, —CH(NH₂)—, and —C(H₂)NHC(NH)NH₂—.

In a further embodiment, M and M' are —CH₂— and A is selected from the group consisting of —O—, —CH₂—, and —C(CH₃)₂—.

6.1.6 Fused Bicyclic Proline Compounds of Structural Formula VII

In addition, the present disclosure provides substantially enantiomerically pure heterobicyclic imino acid compounds of structural Formula VII:

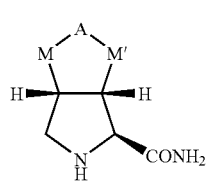

VII including salts and hydrates thereof, wherein A is O, CR¹R², —C═C—, or —CH₂—CH₂—, wherein R¹ and R² are each independently selected from —H, —COOH, —X, —NH₂, —CH₂NHC(NH)NH₂, —CX₃, —CH₃, —CH₂CH₃, and wherein X is selected from F, Cl, and Br. M and M' may both be present or may both be absent and when both M and M' are present M and M' are the same and are selected from O and CR³R⁴ wherein R³ and R⁴ are H, or R³ or R⁴ of M and R³ or R⁴ of M' form a methylene bridge, with the provisos that: (a) when M and M' are O, A is not O; and when A is O, M and M' are not O; (b) A can be —CH═CH— or —CH₂—CH₂— when M and M' are CR³R⁴; and (c) when M and M' are CR³R⁴ and have one or more stereocenters, the stereocenters of M and M' are of opposite stereochemistry.

In one embodiment, R⁶ and R⁷ are both H.
In one embodiment, A is —CH₂—.
In another embodiment A is —CH(CH₃)—.
In another embodiment A is —C(CH₃)₂—.
In another embodiment A is —CH(CH₂CH₃)—.
In another embodiment A is —C(CH₂CH₃)₂—.
In another embodiment A is —C(CH₂CH₃)(CH₃)—.

In one embodiment M and M' are absent and A is selected from the group consisting of —CH₂—, —CH(CH₃)—, —CH(C₂H₅)—, —C(CH₃)₂—, —C(C₂H₅)₂—, —CF₂—, —CCl₂—, —CBr₂—, —C(CF₃)₂—, —CH(COOH)—, —C(COOH)₂—, —CH(NH₂)—, and —CH(CH₂NHC(NH)NH₂)—.

In another embodiment M and M' are absent and A is selected from the group consisting of —CH₂—, —C(CH₃)₂—, —C(CH₃)₂—, and —C(C₂H₅)₂—.

In another embodiment, M and M' are —CH₂— and A is selected from the group consisting of —O—, —CH₂—, —C(CH₃)₂—, —CH(CH₃)—, —C(C₂H₅)₂—, —CH(C₂H₅)—, —CF₂—, —CCl₂—, —CBr₂—, —C(CF₃)₂—, —CH(COOH)—, —C(COOH)₂—, —CH(NH₂)—, and —C(H₂)NHC(NH)NH₂—.

In a further embodiment, M and M' are —CH₂— and A is selected from the group consisting of —O—, —CH₂—, and —C(CH₃)₂—.

6.2 Monoamine Oxidases of the Disclosure

The monoamine oxidases of the present disclosure, which are capable of oxidizing an amine compound of structural Formula I to the corresponding imine compound of structural Formula II, have one or more amino acid substitutions as compared to the amino acid sequence of SEQ ID NO: 2, SEQ ID NO:6, and SEQ ID NO: 32. Such amino acid substitutions provide the monoamine oxidase with one or more improved properties including an increase in enzyme activity, stereospecificity, thermostability, solvent stability, reduced product inhibition, reduced substrate inhibition, or reduced sensitivity to reaction by-products. Such amino acid substitutions may also improve the expression level, solubility, and/or the stability of the monoamine oxidase in a host cell, e.g., as a recombinantly-expressed protein in a heterologous host cell, such as but not limited to an E. coli host cell. In one embodiment, an amino acid substitution S465G provides a substantial increase in the expression level, solubility, and/or the stability of a monoamine oxidase of the present disclosure in E. coli.

The present disclosure also provides polynucleotides encoding such monoamine oxidases and methods for using the polypeptides in the biocatalytic processes disclosed.

In some embodiments, the monoamine oxidases disclosed in the present specification, are improved as compared to the enzyme of SEQ ID NO:2, SEQ ID NO:6 or SEQ ID NO:32 with respect to their rate of enzymatic activity, i.e., their rate of converting an amine compound of structural Formula I to the corresponding imine compound of structural Formula II. In some embodiments, the monoamine oxidases disclosed are capable of converting the substrate to the product at a rate that is at least 1.5-times, 2-times, 3-times, 4-times, 5-times, 10-times, 25-times, 50-times, 100-times, or more than 100-times the rate exhibited by the monoamine oxidase of SEQ ID NO:2, SEQ ID NO:6 and SEQ ID NO:32. Exemplary polypeptides with such properties include, but are not limited to, polypeptides which comprise an amino acid sequence corresponding to SEQ ID NO: 4, 8, 10, 12, 14, 16, 18, 20, or 36.

In some embodiments, the monoamine oxidases disclosed herein are capable of converting an amine compound of structural Formula I to the corresponding imine compound of structural Formula II with a percent diastereometric excess of at least about 95%. Exemplary polypeptides with such properties include, but are not limited to, polypeptides which comprise an amino acid sequence corresponding to SEQ ID NO: 4, 8, 10, 12, 14, 16, 18, 20, or 36.

In some embodiments, an improved monoamine oxidase of the disclosure is based on the sequence formulas of SEQ ID NO: 4, 8, 10, 12, 14, 16, 18, or 20 and can comprise an amino acid sequence that is at least about 85%, 86%, 87%, 88%, 89%, 90%, 91%, 92%, 93%, 94%, 95%, 96%, 97%, 98%, or 99% identical thereto. These differences can be an amino acid insertion, deletion, substitution, or any combination of such changes. In some embodiments, the amino acid sequence differences can comprise non-conservative, conservative, as well as a combination of non-conservative and conservative amino acid substitutions. Various amino acid residue positions where such changes can be made are described herein.

In some embodiments, an improved monoamine oxidase of the disclosure comprises an amino acid sequence in which the amino acid corresponding to residue 99 of SEQ ID NO: 2 and SEQ ID NO: 6, and residue 97 of SEQ ID NO: 32, glutamine, is substituted with an acidic amino acid, i.e., aspartic acid or glutamic acid. In a particular embodiment, that glutamine residue is replaced with a glutamic acid residue.

In some embodiments, an improved monoamine oxidase of the disclosure comprises an amino acid sequence in which the amino acid corresponding to residue 365 of SEQ ID NO: 2, and SEQ ID NO: 6, and residue 363 of SEQ ID NO: 32, tyrosine, is conservatively substituted with a different aromatic amino acid, i.e., phenylalanine or tryptophan. In a particular embodiment, that tyrosine residue is replaced with a tryptophan residue.

In some embodiments, an improved monoamine oxidase of the disclosure comprises an amino acid sequence in which the amino acid corresponding to residue 382 of SEQ ID NO: 2 and SEQ ID NO: 6, and residue 380 of SEQ ID NO: 32, phenylalanine, is substituted with a nonpolar amino acid, i.e., valine, isoleucine, alanine, glycine, methionine, or leucine. In a particular embodiment, that phenylalanine residue is replaced with a leucine residue.

In some embodiments, an improved monoamine oxidase of the disclosure comprises an amino acid sequence in which the amino acid corresponding to residue 465 of SEQ ID NO: 2 and SEQ ID NO: 6, and residue 463 of SEQ ID NO: 32, serine, is substituted with a nonpolar amino acid, i.e., valine, isoleucine, alanine, methionine, leucine, or glycine. In a particular embodiment, that serine residue is replaced with a glycine residue.

In other embodiments, an improved monoamine oxidase of the disclosure comprises an amino acid sequence in which the amino acid corresponding to residue 135 of SEQ ID NO: 2 and SEQ ID NO: 6, threonine, is conservatively substituted with another polar amino acid, i.e., serine, glutamine, or asparagine. In a particular embodiment, that threonine residue is replaced with a glutamine residue.

In some embodiments, an improved monoamine oxidase of the disclosure comprises an amino acid sequence in which the amino acid corresponding to residue 284 of SEQ ID NO: 2 and SEQ ID NO: 6, asparagine, is substituted with an acidic amino acid, i.e., aspartic acid or glutamic acid. In a particular embodiment, that asparagine residue is replaced with a glutamic acid residue.

In some embodiments, an improved monoamine oxidase of the disclosure comprises an amino acid sequence in which the amino acid corresponding to residue 289 of SEQ ID NO: 2 and SEQ ID NO: 6, alanine, is conservatively substituted with another nonpolar amino acid, i.e., glycine, valine, leucine, isoleucine, or methionine. In a particular embodiment, that alanine residue is replaced with a valine residue.

In other embodiments, an improved monoamine oxidase of the disclosure comprises an amino acid sequence in which the amino acid corresponding to residue 384 of SEQ ID NO: 2, lysine, is conservatively substituted with another polar amino acid, i.e., serine, threonine, or glutamine. In a particular embodiment, that lysine residue is replaced with a glutamine residue.

In some embodiments, an improved monoamine oxidase of the disclosure is a monoamine oxidase that is a homologue of the monoamine oxidase of *Aspergillus niger* (SEQ ID NO:2) or a homologue of the monoamine oxidase of *Aspergillus oryzae* (SEQ ID NO:32) and that carries one or more of the amino acid substitutions corresponding to those disclosed herein. Illustrative homologues include the monoamine oxidases of SEQ ID NO: 22, SEQ ID NO: 24, SEQ ID NO: 26, SEQ ID NO: 28, SEQ ID NO: 30, SEQ ID NO: 32, and SEQ ID NO: 34. Therefore, in certain embodiments, an improved monoamine oxidase of the disclosure is a monoamine oxidase selected from the enzymes of SEQ ID NO: 22, SEQ ID NO: 24, SEQ ID NO: 26, SEQ ID NO: 28, SEQ ID NO: 30, SEQ ID NO: 32, and SEQ ID NO: 34 that carries one or more of the amino acid substitutions corresponding to those disclosed herein

6.3 Definitions

As used herein, the following terms are intended to have the following meanings.

"Monoamine oxidase" refers to a polypeptide having an enzymatic capability of oxidizing a compound of structural Formula I, supra to the corresponding product of structural Formula II, supra. The polypeptide typically utilizes an oxidized cofactor, such as but not limited to flavin adenine dinucleotide (FAD), flavin adenine mononucleotide (FMN), nicotinamide adenine dinucleotide (NAD), or nicotinamide adenine dinucleotide phosphate (NADP). In a particular embodiment, the oxidized cofactor is FAD. Monoamine oxidases as used herein include naturally occurring (wild type) monoamine oxidases as well as non-naturally occurring engineered polypeptides generated by human manipulation.

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, *Current Protocols in Molecular Biology*, F. M.

Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, *J. Mol. Biol.* 215: 403-410 and Altschul et al., 1977, *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Natl Acad Sci USA* 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to," "reference to," or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered monoamine oxidase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diasteromers, commonly alternatively reported as the diastereometric excess (d.e.). Enantiomeric excess and diastereometric excess are types of stereometric excess.

"Highly stereoselective": refers to a monoamine oxidase polypeptide that is capable of converting the substrate to the corresponding product with at least about 99% stereometric excess.

"Stereospecificity" refers to the preferential conversion in a chemical or enzymatic reaction of one stereoisomer over another. Stereospecificity can be partial, where the conversion of one stereoisomer is favored over the other, or it may be complete where only one stereoisomer is converted.

"Chemoselectivity" refers to the preferential formation in a chemical or enzymatic reaction of one product over another.

"Improved enzyme property" refers to a monoamine oxidase polypeptide that exhibits an improvement in any enzyme property as compared to a reference monoamine oxidase. For the engineered monoamine oxidase polypeptides described herein, the comparison is generally made to the wild-type monoamine oxidase enzyme, although in some embodiments, the reference monoamine oxidase can be another improved engineered monoamine oxidase. Enzyme properties for which improvement is desirable include, but are not limited to, enzymatic activity (which can be expressed in terms of percent conversion of the substrate), thermal stability, pH activity profile, cofactor requirements, refractoriness to inhibitors (e.g., product inhibition), stereospecificity, stereoselectivity (including enantioselectivity), solubility, and stability and expression level in a host cell.

"Increased enzymatic activity" refers to an improved property of the engineered monoamine oxidase polypeptides, which can be represented by an increase in specific activity (e.g., product produced/time/weight protein) or an increase in percent conversion of the substrate to the product (e.g., percent conversion of starting amount of substrate to product in a specified time period using a specified amount of monoamine oxidase) as compared to the reference monoamine oxidase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.5 times the enzymatic activity of the corresponding wild-type monoamine oxidase, to as much as 2 times. 5 times, 10 times, 20 times, 25 times, 50 times, 75 times, 100 times or more enzymatic activity than the naturally occurring monoamine oxidase or another engineered monoamine oxidase from which the monoamine oxidase polypeptides were derived. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10^9$ ($M^{-1}s^{-1}$). Hence, any improvements in the enzyme activity of the monoamine oxidase will have an upper limit related to the diffusion rate of the substrates acted on by the monoamine oxidase enzyme. Monoamine oxidase activity can be measured using published methods, or adaptations thereof, for measuring monoamine oxidase, such as, but not limited to those disclosed by Zhou et al. (Zhou et al. "A One-Step Fluorometric Method for the Continuous Measurement of Monoamine Oxidase Activity," 1997 *Anal. Biochem.* 253:169-74) and Szutowicz et al. (Szutowicz et al., "Colorimetric Assay for Monoamine Oxidase in Tissues Using Peroxidase and 2,2'-Azino(3-ethylbenzthaizoline-6-sulfonic Acid) as Chromogen," 1984, *Anal. Biochem.* 138:86-94). Comparisons of enzyme activities are made using a defined preparation of enzyme, a defined assay under a set condition, and one or more defined substrates, as further described in detail herein or using the methods of, e.g., Zhou and Szutowicz. Generally, when lysates are compared, the numbers of cells and the amount of protein assayed are determined as well as use of identical expression systems and identical host cells to minimize variations in amount of enzyme produced by the host cells and present in the lysates.

"Conversion": refers to the enzymatic oxidation of the substrate to the corresponding product. "Percent conversion" refers to the percent of the substrate that is oxidized to the product within a period of time under specified conditions. Thus, the "enzymatic activity" or "activity" of a monoamine oxidase polypeptide can be expressed as "percent conversion" of the substrate to the product.

"Thermostable" refers to a monoamine oxidase polypeptide that maintains similar activity (more than 60% to 80% for example) after exposure to elevated temperatures (e.g. 40-80° C.) for a period of time (e.g. 0.5-24 hrs) compared to the untreated enzyme.

"Solvent stable" refers to a monoamine oxidase polypeptide that maintains similar activity (more than e.g. 60% to 80%) after exposure to varying concentrations (e.g. 5-99%) of solvent (isopropyl alcohol, tetrahydrofuran, 2-methyltetrahydrofuran, acetone, toluene, butylacetate, methyl tert-butylether, etc.) for a period of time (e.g. 0.5-24 hrs) compared to the untreated enzyme.

"pH stable" refers to a monoamine oxidase polypeptide that maintains similar activity (more than e.g. 60% to 80%) after exposure to high or low pH (e.g. 4.5-6 or 8 to 12) for a period of time (e.g. 0.5-24 hrs) compared to the untreated enzyme.

"Thermo- and solvent stable" refers to a monoamine oxidase polypeptide that is both thermostable and solvent stable.

"Derived from" as used herein in the context of engineered monoamine oxidase enzymes, identifies the originating monoamine oxidase enzyme, and/or the gene encoding such monoamine oxidase enzyme, upon which the engineering was based. For example, the engineered monoamine oxidase enzyme of SEQ ID NO:8 was obtained by artificially evolving, over multiple generations the gene encoding the *Aspergillus niger* monoamine oxidase enzyme of SEQ ID NO:2. Thus, this engineered monoamine oxidase enzyme is "derived from" the wild-type monoamine oxidase of SEQ ID NO:2.

"Hydrophilic Amino Acid or Residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include L-Thr (T), L-Ser (S), L-His (H), L-Glu (E), L-Asn (N), L-Gln (O), L-Asp (D), L-Lys (K) and L-Arg (R).

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (O), L-Ser (S) and L-Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic Amino Acid or Residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-pro (P) and L-his (H). Histidine has a constrained geometry because it has a relatively small imidazole ring. Proline has a constrained geometry because it also has a five membered ring.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic Amino Acid or Residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine." The amino acid L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small Amino Acid or Residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing Amino Acid or Residue" refers to an amino acid containing a hydroxyl (—OH) moiety. Genetically-encoded hydroxyl-containing amino acids include L-Ser (S) L-Thr (T) and L-Tyr (Y).

"Conservative" amino acid substitutions or mutations refer to the interchangeability of residues having similar side chains, and thus typically involves substitution of the amino acid in the polypeptide with amino acids within the same or similar defined class of amino acids. However, as used herein, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. Table 1 below shows exemplary conservative substitutions.

TABLE 1

Conservative Substitutions

| Residue | Possible Conservative Mutations |
| --- | --- |
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar (N, Q, S, T) |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered monoamine oxidase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered monoamine oxidase enzymes comprise insertions of one or more amino acids to the naturally occurring monoamine oxidase as well as insertions of one or more amino acids to other improved monoamine oxidase polypeptides. Insertions can be in the internal portions of the polypeptide, or to the carboxy or amino terminus Insertions as used herein include fusion proteins as is known in the art. The insertion can be a contiguous segment of amino acids or separated by one or more of the amino acids in the naturally occurring polypeptide.

"Different from" or "differs from" with respect to a designated reference sequence refers to difference of a given amino acid or polynucleotide sequence when aligned to the reference sequence. Generally, the differences can be determined when the two sequences are optimally aligned. Differences include insertions, deletions, or substitutions of amino acid residues in comparison to the reference sequence.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length monoamine oxidase polypeptide.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved monoamine oxidase may be present within a cell, present in the cellular medium, or prepared in various forms, such as lysates or isolated preparations. As such, in some embodiments, the improved monoamine oxidase can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure monoamine oxidase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved monoamine oxidase polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$, values for polynucleotides can be calculated using known methods for predicting melting temperatures (see, e.g., Baldino et al., *Methods Enzymology* 168:761-777; Bolton et al., 1962, *Proc. Natl. Acad. Sci. USA* 48:1390; Bresslauer et al., 1986, *Proc. Natl. Acad. Sci. USA* 83:8893-8897; Freier et al., 1986, *Proc. Natl. Acad. Sci. USA* 83:9373-9377; Kierzek et al., *Biochemistry* 25:7840-7846; Rychlik et al., 1990, *Nucleic Acids Res* 18:6409-6412 (erratum, 1991, *Nucleic Acids Res* 19:698); Sambrook et al., supra); Suggs et al., 1981, In *Developmental Biology Using Purified Genes* (Brown et al., eds.), pp. 683-693, Academic Press; and Wetmur, 1991, *Crit. Rev Biochem Mol Biol* 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered monoamine oxidase enzyme of the present disclosure.

"Hybridization stringency" relates to such washing conditions of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA; with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the monoamine oxidase enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariat analysis, for example, using cluster analysis or correspondence analysis, and the effective number of codons used in a gene (see GCG CodonPreference, Genetics Computer Group Wisconsin Package; Codon W, John Peden, University of Nottingham; McInerney, J. O, 1998, Bioinformatics 14:372-73; Stenico et al., 1994, *Nucleic Acids Res.* 222437-46; Wright, F., 1990, *Gene* 87:23-29). Codon usage tables are available for a growing list of organisms (see for example, Wada et al., 1992, *Nucleic Acids Res.* 20:2111-2118; Nakamura et al., 2000, *Nucl. Acids Res.* 28:292; Duret, et al., supra; Henaut and Danchin, "*Escherichia coli* and *Salmonella*," 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., *Bioinformatics: Sequence and Genome Analysis*, Chapter 8, Cold Spring Harbor Laboratory Press, Cold Spring Harbor, N.Y., 2001; Uberbacher, E. C., 1996, *Methods Enzymol.* 266:259-281; Tiwari et al., 1997, *Comput. Appl. Biosci.* 13:263-270).

"Control sequence" is defined herein to include all components, which are necessary or advantageous for the expression of a polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed at a position relative to the coding sequence of the DNA sequence such that the control sequence directs the expression of a polynucleotide and/or polypeptide.

"Promoter sequence" is a nucleic acid sequence that is recognized by a host cell for expression of the coding region. The control sequence may comprise an appropriate promoter sequence. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"—$(C_1$-$C_{10})$alkyl" means a straight chain or branched non cyclic hydrocarbon having from 1 to 10 carbon atoms. Representative straight chain —$(C_1$-$C_{10})$alkyls include -methyl, -ethyl, -n propyl, -n-butyl, -n-pentyl, -n-hexyl, -n-heptyl, -n-octyl, -n-nonyl, and -n-decyl. A branched alkyl means that one or more straight chain —$(C_1$-$C_8)$alkyl groups, such as -methyl, -ethyl or -propyl, replace one or both hydrogens in a —$CH_2$— group of a straight chain alkyl. A branched non cyclic hydrocarbon means that one or more straight chain —$(C_1$-$C_{10})$alkyl groups, such as -methyl, -ethyl or -propyl, replace one or both hydrogens in a —$CH_2$— group of a straight chain non cyclic hydrocarbon. Representative branched —$(C_1$-$C_{10})$alkyls include iso-propyl, sec-butyl, iso-butyl, tert-butyl, iso-pentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—$(C_1$-$C_6)$alkyl" means a straight chain or branched non cyclic hydrocarbon having from 1 to 6 carbon atoms. Representative straight chain —$(C_1$-$C_6)$alkyls include -methyl, -ethyl, -n-propyl, -n-butyl, -n-pentyl, and n-hexyl. Representative branched $(C_1$-$C_6)$alkyls include iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—$(C_1$-$C_4)$alkyl" means a straight chain or branched non cyclic hydrocarbon having from 1 to 4 carbon atoms. Representative straight chain —$(C_1$-$C_4)$alkyls include -methyl, -ethyl, -n-propyl, and -n-butyl. Representative branched —$(C_1$-$C_4)$alkyls include -iso-propyl, -sec-butyl, -iso-butyl, and -tert-butyl.

"—$(C_1$-$C_3)$alkyl" means a straight chain or branched non cyclic hydrocarbon having from 1 to 3 carbon atoms. Representative straight chain $(C_1$-$C_3)$alkyls include -methyl, -ethyl, and n-propyl. Representative branched —$(C_1$-$C_3)$alkyls include -iso-propyl.

"—$(C_1$-$C_2)$alkyl" means a straight chain non cyclic hydrocarbon having 1 or 2 carbon atoms. Representative straight chain —$(C_1$-$C_2)$alkyls include -methyl and -ethyl.

"—$(C_2$-$C_{10})$alkenyl" means a straight chain or branched non cyclic hydrocarbon having from 2 to 10 carbon atoms and including at least one carbon-carbon double bond. A branched alkenyl means that one or more straight chain —$(C_1$-$C_8)$alkyl groups, such as -methyl, -ethyl or -propyl, replace one or both hydrogens in a —$CH_2$— or —$CH=$ group of a straight chain alkenyl. Representative straight chain and branched $(C_2$-$C_{10})$alkenyls include -vinyl, -allyl, 1-butenyl, -2-butenyl, -iso-butylenyl, -1-pentenyl, -2-pentenyl, -3-methyl-1-butenyl, 2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

"—$(C_2$-$C_6)$alkenyl" means a straight chain or branched non cyclic hydrocarbon having from 2 to 6 carbon atoms and including at least one carbon-carbon double bond. Representative straight chain and branched —$(C_2$-$C_6)$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, and the like.

"—$(C_2$-$C_{10})$alkynyl" means a straight chain or branched non cyclic hydrocarbon having from 2 to 10 carbon atoms and including at least one carbon-carbon triple bond. A branched alkynyl means that one or more straight chain —$(C_1$-$C_8)$alkyl groups, such as -methyl, -ethyl or -propyl, replace one or both hydrogens in a —$CH_2$— group of a straight chain alkynyl. Representative straight chain and branched —$(C_2$-$C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—$(C_2$-$C_6)$alkynyl" means a straight chain or branched non cyclic hydrocarbon having from 2 to 6 carbon atoms and including at least one carbon-carbon triple bond. Representative straight chain and branched $(C_2$-$C_6)$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—($C_1$-$C_6$)alkoxy" means a straight chain or branched non cyclic hydrocarbon having one or more ether groups and from 1 to 6 carbon atoms. Representative straight chain and branched ($C_1$-$C_6$)alkoxys include -methoxy, -ethoxy, -methoxymethyl, -2-methoxyethyl, -5-methoxypentyl, -3-ethoxybutyl and the like.

"—($C_3$-$C_{12}$)cycloalkyl" means a saturated monocyclic hydrocarbon having from 3 to 12 carbon atoms. Representative ($C_3$-$C_{12}$)cycloalkyls are -cyclopropyl, -cyclobutyl, -cyclopentyl, -cyclohexyl, -cycloheptyl, -cyclooctyl, -cyclononyl, -cyclodecyl, and -cyclododecyl.

"—($C_4$-$C_8$)cycloalkyl" or "4- to 8-member cycloalkyl ring" means a saturated monocyclic hydrocarbon having from 4 to 8 carbon atoms. Representative —($C_4$-$C_8$)cycloalkyls are -cyclobutyl, -cyclopentyl, -cyclohexyl, -cycloheptyl, and -cyclooctyl.

"—($C_3$-$C_8$)cycloalkyl" means a saturated monocyclic hydrocarbon having from 3 to 8 carbon atoms. Representative —($C_3$-$C_8$)cycloalkyls include -cyclopropyl, -cyclobutyl, -cyclopentyl, -cyclohexyl, -cycloheptyl, and -cyclooctyl.

"—($C_3$-$C_7$)cycloalkyl" means a saturated monocyclic hydrocarbon having from 3 to 7 carbon atoms. Representative ($C_3$-$C_7$)cycloalkyls include -cyclopropyl, -cyclobutyl, -cyclopentyl, -cyclohexyl, and -cycloheptyl.

"-(6- to 10-membered)heterobicyclic" or "-(6- to 10-membered)bicycloheterocyclo" means a 6 to 10 membered bicyclic, heterocyclic ring which is either saturated, unsaturated non-aromatic, or aromatic. A -(6- to 10-membered)heterobicyclic contains from 1 to 4 heteroatoms independently selected from nitrogen, which can be quaternized; oxygen; and sulfur, including sulfoxide and sulfone. The -(6- to 10-membered)heterobicyclic can be attached via a nitrogen or carbon atom. Representative -(6- to 10-membered)heterobicyclics include-3-azabicyclo[3.1.0]hexane, -quinolinyl, -isoquinolinyl, -chromonyl, -coumarinyl, -indolyl, -indolizinyl, benzo[b]furanyl, benzo[b]thiophenyl, -indazolyl, -purinyl, -4H-quinolizinyl, isoquinolyl, -quinolyl, -phthalazinyl, -naphthyridinyl, -carbazolyl, β-carbolinyl, -indolinyl, -isoindolinyl, -1,2,3,4-tetrahydroquinolinyl, -1,2,3,4-tetrahydroisoquinolinyl, pyrrolopyrrolyl and the like.

"—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

"—CH(halo)$_2$" means a methyl group where two of the hydrogens of the methyl group have been replaced with a halogen. Representative —CH(halo)$_2$ groups include —$CHF_2$, —$CHCl_2$, —$CHBr_2$, —$CHBrCl$, —$CHClI$, and —$CHI_2$.

"—C(halo)$_3$" means a methyl group where each of the hydrogens of the methyl group has been replaced with a halogen. Representative —C(halo)$_3$ groups include —$CF_3$, —$CCl_3$, —$CBr_3$, and —$Cl_3$.

"-Halogen" or "-halo" means —F, —Cl, —Br, or —I.

"Oxo", "=O", and the like as used herein mean an oxygen atom doubly bonded to carbon or another element.

When a first group is "substituted with one or more" second groups, one or more hydrogen atoms of the first group are replaced with a corresponding number of second groups. When the number of second groups is two or greater, each second group can be the same or different.

In one embodiment, a first group is substituted with up to three second groups.

In another embodiment, a first group is substituted with one or two second groups.

In another embodiment, a first group is substituted with only one second group.

As used herein, the terms "stereoisomer," "stereoisomeric form," and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is non-superimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule.

"Substantially enantiomerically pure," as used herein means that the indicated enantiomer of a compound is present to a greater extent or degree than another enantiomer of the same compound. Accordingly, in particular embodiments, a substantially enantiomerically pure compound is present in 80%, 85%, 90%, 91%, 92%, 93%, 94%, 95%, 96%, 97%, 98%, or 99% enantiomeric excess over another enantiomer of the same compound.

"Substantially stereometrically pure," as used herein means that the indicated enantiomer or diastereomer of a compound is present to a greater extent or degree than another enantiomer or diastereomer of the same compound. As noted above with respect to "stereoselectivity," enantiomeric excess and diastereometric excess are types of stereometric excess. Accordingly, in particular embodiments, a substantially stereometrically pure compound is present in 80%, 85%, 90%, 91%, 92%, 93%, 94%, 95%, 96%, 97%, 98%, or 99% stereometric excess over another enantiomer or diastereomer of the same compound.

6.4 Methods for Making the Heterobicyclic Compounds of the Disclosure

The heterobicyclic compounds of the disclosure are assembled using the biocatalyic processes disclosed below, using the monoamine oxidases disclosed herein as the biological catalysts.

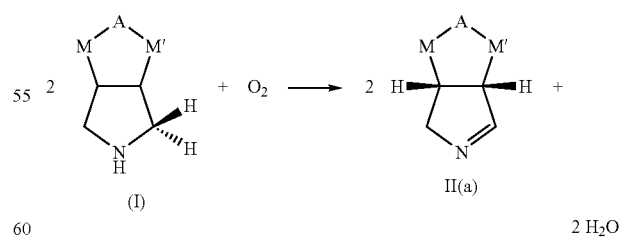

Scheme 1 depicts the reaction catalyzed by the monoamine oxidases of the disclosure whereby a secondary amine, i.e., a heterobicyclic compound according to structural Formula I is oxidized to the corresponding imine compound of structural Formula II(a).

SCHEME 2

Reaction (1):

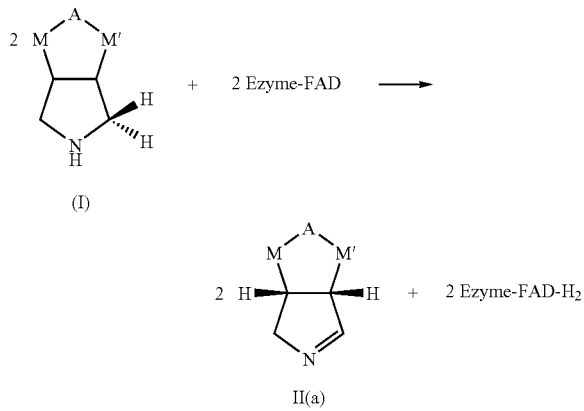

Reaction (2):

2 O$_2$ + 2 Ezyme-FAD-H$_2$ ⟶ 2 Ezyme-FAD-H$_2$O$_2$

Reaction (3):

2 H$_2$O$_2$ ⟶ 2 H$_2$O + O$_2$

Scheme 2 depicts the three elementary reactions that, together, provide the overall net reaction depicted in Scheme 1. In the first reaction of Scheme 2, the secondary amine, a heterobicyclic compound according to structural Formula I is enantioselectively oxidized to the corresponding imine compound of structural Formula II(a) by a monoamine oxidase of the disclosure (which is complexed with a flavin adenine nucleotide co-factor (FAD)) to provide the corresponding substantially enantiomerically pure imine of structural Formula II and the reduced monoamine oxidase FAD complex (Enzyme-FAD-H$_2$). In the second step, the reduced monoamine oxidase (Enzyme-FAD-H$_2$ complex) is re-oxidized by molecular oxygen, yielding hydrogen peroxide (H$_2$O$_2$) as a byproduct. In the third reaction (which is not catalyzed by the monoamine oxidase), hydrogen peroxide (H$_2$O$_2$) breaks down to water and oxygen.

Substrate secondary amines of structural Formula I are commercially available or are readily synthesized using methods and reagents either known in the art or readily adapted, in light of the present disclosure, from methods and reagents known in the art (see e.g. Delalu et al. (1999) *J. Heterocyclic Chem.* 36, 681; WO 2007/022459; and WO 2007/075790, and references cited therein).

Hydrogen peroxide is a strong oxidizing agent capable of irreversibly inactivating the monoamine oxidase enzyme. Accordingly, in certain embodiments, a component useful for facilitating the disproportionation reaction depicted in step 3 of Scheme 2, above, in which hydrogen peroxide (H$_2$O$_2$) is broken down to molecular oxygen and water. In certain embodiments, that component is selected from among chemical agents, such as but not limited to Pd, Fe, and the like, while in other embodiments, that component is an enzyme, such as the enzyme catalase. In a particular embodiment, the reaction mixture further comprises the enzyme catalase to catalyze the disproportionation reaction of step 3 of Scheme 2, in which two molecules of hydrogen peroxide are broken down to provide two molecules of water and one of molecular oxygen. In particular embodiments the catalase is an *Aspergillus niger* catalase that is included in the reaction at a concentration of from about 0.01% to about 1% (w/v), from about 0.05% to about 0.5% (w/v), or from about 0.1% to about 0.2% (w/v).

In those instances in which the compound of structural Formula I is volatile liquid, to facilitate handling, it may be provided as a salt. In one aspect of this embodiment, the amine substrate is converted to an acetate salt by addition of one equivalent of acetic acid to a 10% solution of the free base dissolved, e.g., in heptane. The precipitated salt is collected, washed with solvent (e.g., the solvent from which the salt is precipitated, e.g., heptane) and dried at room temperature (about 21° C.) under reduced pressure.

As indicated in Scheme 1, the ultimate oxidant is molecular oxygen. In view of the limited solubility of oxygen in water and in light of the decrease in that solubility as the temperature and salinity (solute concentration) increase, molecular oxygen in solution for reaction must be replenished by gas-liquid mass transfer from a gas phase. Typically, the activity and amount of preferred monoamine oxidases provided for practical reaction rates are sufficient for the reaction to become limited by the rate of gas-liquid mass transfer. As is well known, the rate of gas-liquid mass transfer is dependent on the partial pressure of the gas in the liquid, the solubility of the gas in the liquid, and the gas-liquid interfacial area. According, the rate of a gas-liquid mass transfer rate-limited reaction can be increased by engineering environments that provide aggressive gas-liquid mixing, including by sparging, hollow shaft impeller aspiration, countercurrent gas-liquid circulation, vertically serpentine tubular flow, and the like. Additionally, in any engineering environment, the rate of an oxygen gas-liquid mass transfer rate-limited reaction can be increased by increasing the partial pressure of oxygen, either by increasing the total gas pressure, increasing the fraction of oxygen in the gas (such as enriching or replacing air with purified oxygen, of both. In particular embodiments, the concentration of dissolved oxygen and/or the rate of oxygen consumption from the gas phase is continuously monitored and the oxygen feed rate, partial pressure, mixing efficiency, or combinations thereof are adjusted to provide a beneficial rate of reaction or overall reaction time to completion.

In certain embodiments, the reaction mixture may also comprise at least one antifoam. In a particular embodiment, the antifoam is a commercially-available material such as but not limited to Antifoam-204 or Antifoam Y-30 (Sigma, St. Louis Mo.), or the like. In other embodiments, the reaction may comprise more than one antifoam. The antifoam may be included in the reaction at a concentration of from about 0.01% to about 1% (w/v if solid or v/v if a liquid), from about 0.05% to about 0.5%, or from about 0.1% to about 0.2%.

In certain embodiments, the oxidized imine compounds of structural Formula II may be isolated from the reaction mixture, purified, and characterized. In other embodiments, described below, the imine compounds of structural Formula II may be converted to another adduct or intermediate and used in a subsequent step without isolation or purification.

SCHEME 3

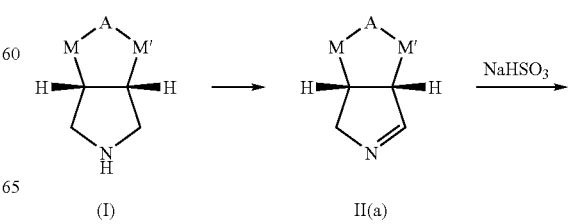

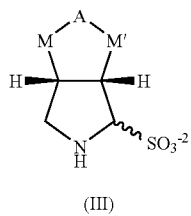

(III)

In certain embodiments, the monoamine oxidase of the disclosure may be inhibited by the product imine of structural Formula II. Accordingly, in particular embodiments, the reaction in which a compound of structural Formula I is oxidized to a compound of structural Formula II further comprises an agent that will react with the imine compound of structural Formula II to form an adduct with a reduced or eliminated ability to inhibit a monoamine oxidase of the disclosure, as depicted in Scheme 3. In one aspect of this embodiment, the agent is added at the beginning of the reaction or is added intermittently or continuously in amounts sufficiently high to prevent accumulation of an inhibitory amount of the imine compound of structural Formula II but low enough to avoid accumulation of an enzyme-inhibitory amount of that agent. In one embodiment, the agent is sodium bisulfite, which may be conveniently supplied as sodium metabisulfite, which hydrates in water to sodium bisulfite. Reaction of bisulfite with the imine compound of structural Formula II provides the sulfite adducts of structural Formula III. In certain embodiments, sodium bisulfite is added continuously to the reaction at a rate whereby this reagent is "instantaneously" consumed and the potentially inhibitory imine product of structural Formula II is "trapped" as the less inhibitory or non inhibitory sulfite adduct compound of structural Formula III.

Whether the monoamine oxidase is inhibited by the imine product or not, the addition of bisulfite to react the imine product also provides practical process engineering options. Certain imines of the invention are highly volatile and among those, some are malodorous and/or noxious. Their containment as free bases requires closed reactions, without gas flow, or efficient condensation of chemical trapping (e.g. by a bisulfite solution). In situ reaction to their bisulfite adducts (the aminosulfonates), obviates these engineering constraints while also providing the option to conduct the subsequent reaction with cyanide in the same reaction vessel.

Formation of the bisulfite adduct compound structural Formula III can be reversed at elevated pH, whereby the corresponding imine of structural Formula II is regenerated. Accordingly, in certain embodiments, the reaction of Scheme 3 is quenched by addition of base, e.g., 10 N NaOH, to raise the pH to about 13, regenerating the imine of structural Formula II which can be extracted, e.g., with methyl t-butyl ether ("MBTE") and, in certain embodiments, isolated by distillation to provide an imine of structural Formula II as a colorless oil.

In certain embodiments, the rates of addition the substrate of structural Formula I, the sequestration agent (e.g., sodium bisulfite), and a pH control agent (e.g. NaOH) are monitored and controlled, in part, to minimize or obviate both substrate and product inhibition of the monoamine oxidase used as the biocatalyst for conversion of a compound of structural Formula I to a compound of structural Formula II.

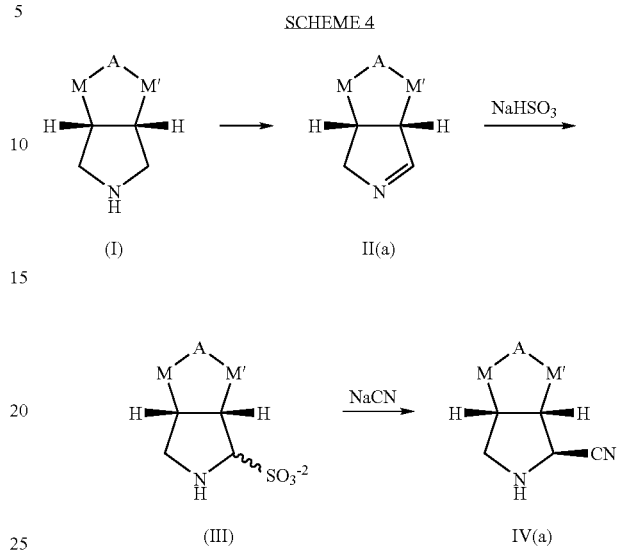

SCHEME 4

In another embodiment, NaCN is added to the reaction of Scheme 3 and the pH allowed to rise to about pH 10, whereby the sulfite adducts of structural Formula III are stereoselectively converted to the trans aminonitrile compounds of structural Formula IV(a), as depicted in Scheme 4. In aspects of this embodiment, about 1 to about 3 equivalents, about 1 to about 2, about 1.05 to about 1.5 equivalents, or about 1.1 to about 1.2 equivalents of NaCN (relative to the imine compound of structural Formula II are added to the reaction to convert the sulfite adducts of structural Formula III to the trans aminonitrile compounds of structural Formula IV(a). Additionally, the reaction of the compound of Formula III produces the cis aminonitrile compounds of structural Formula IV(b).

The trans aminonitrile compounds of structural Formula IV(a) can be extracted from the reaction mixture (1:1 organic solvent: aqueous reaction mixture) using, e.g., 2-methyl tetrahydrofuran, MTBE, or iso-propyl acetate. The trans aminonitrile compound can be recovered from the organic solvent extract, e.g. the organic extract, with optional intermediate further clarifications, can be concentrated under reduced pressure to provide the aminonitrile compounds of structural Formula IV.

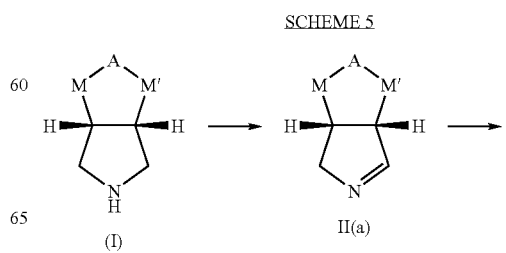

SCHEME 5

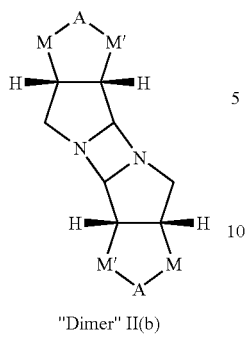

"Dimer" II(b)

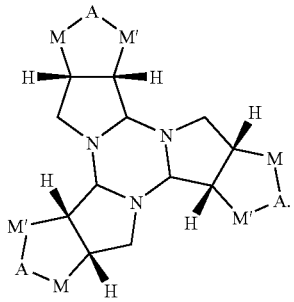

II(c)

In certain embodiments, the imine compounds of structural Formula II react to form the dimeric structures depicted in Scheme 5 (see e.g., *Int. J. Chem. Kinet.* 1998, 30(2), 129-136), thereby minimizing or obviating product inhibition of the monoamine oxidase of the disclosure. Whether the monoamine oxidase is inhibited by the imine product or not, dimerization can also provides practical process engineering options. The dimers are far less volatile, if at all, than the corresponding imines, substantially mitigating the need for engineering containment volatile imines. Moreover, the dimers can typically be readily recovered from the reaction mixture by filtration, extraction, or steam distillation, and typically can be used directly in the subsequent step of the process. Alternatively, the dimers can typically be dissolved in acidic solutions to provide monomeric iminium salt solutions suitable for use in subsequent steps to produce the desired bicyclic proline analogs and derivatives.

The favorability of formation of such trimers can depend on substituent groups. However, such trimer compounds of Formula II(c) would be expected to exhibit little difference in reactivity relative to the dimer when used in the reactions of the present disclosure. Thus, without being bound by mechanism, it is expected that any compounds of Formula II(a) that undergo formation of the trimer of Formula II(c), will exhibit equivalent reactivity to the dimer form.

Upon extraction into a solvent, e.g., MTBE or toluene, the dimer formed according to Scheme 5 can be contacted either with NaCN and acid (e.g., citric, acetic, or hydrochloric acid) or with HCN (at 0° C.) to provide the trans aminonitrile compounds of structural Formula IV(a) and the cis aminonitrile compounds of Formula IV(b).

SCHEME 6

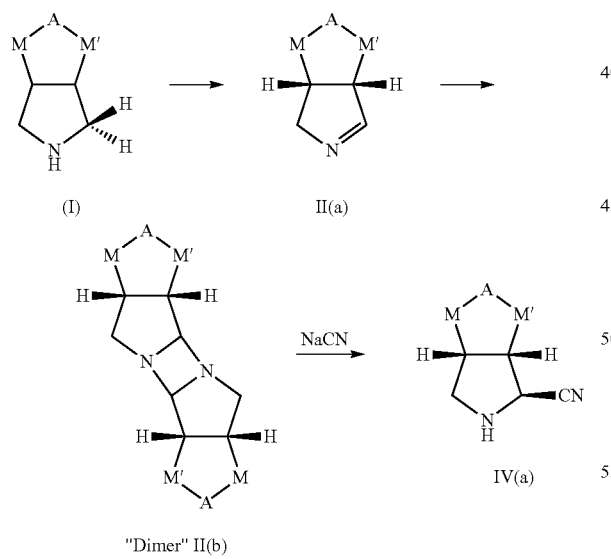

"Dimer" II(b)

It is known that under some conditions imines of pyrrolidine monomer compounds (e.g., 3,4-dihydro-2H-pyrrole) form a dimer and then a thermodynamically favorable trimer structure. Accordingly, certain compounds of Formula II(a) may form not only a dimer, but then go on to form a trimer (e.g., a compound of Formula II(c)) exclusively, or in some mixture with the monomeric and dimeric compounds.

SCHEME 7

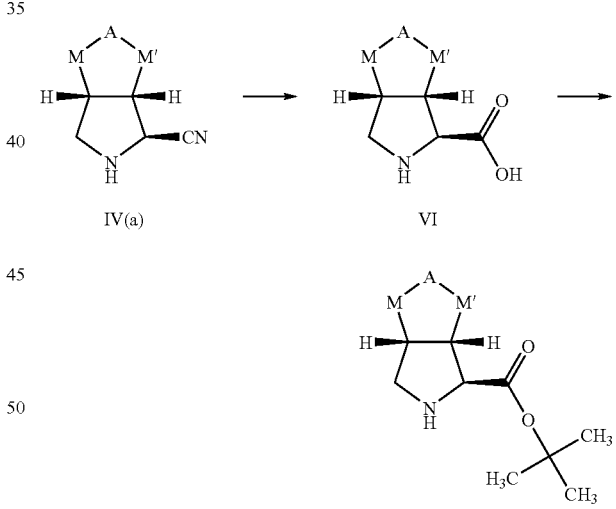

The trans aminonitrile compounds of structural Formula IV(a) prepared e.g. according to Scheme 4 or Scheme 6 can be contacted with aqueous acid (e.g. HCl or $H_2SO_4$) to provide the amino acids of structural Formula VI. The corresponding t-butyl esters of structural Formula V, in which moiety $R^5$ is -t-butyl, are prepared by contacting the amine compounds of structural Formula VI with an acid (e.g., methane sulfonic acid) and isobutylene or a t-butyl ester (e.g., t-butyl acetate), as depicted in Scheme 7.

SCHEME 8

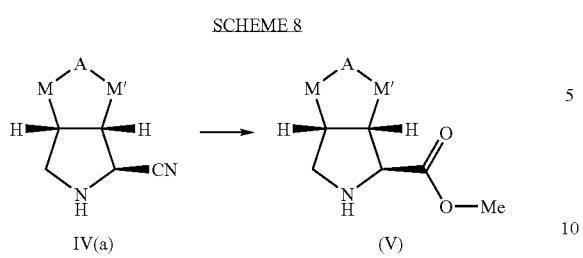

In another embodiment, the trans aminonitrile compounds of structural Formula IV(a) prepared e.g., according to Scheme 4 or Scheme 6 can be contacted with HCl and methanol in a Pinner reaction to provide the methyl esters of structural Formula V, in which moiety $R^5$ is $CH_3$, as shown in Scheme 8.

SCHEME 9

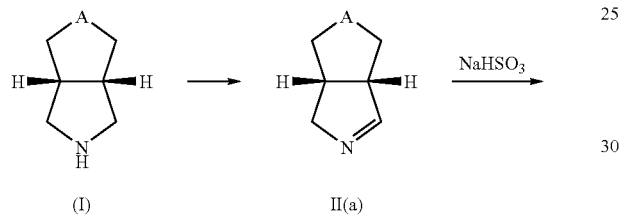

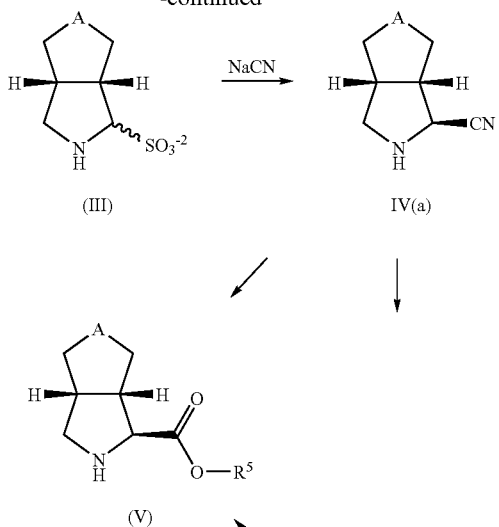

Scheme 9 depicts an overall process for the preparation of compounds according to structural Formulae V and VI from the secondary amines of structural Formula I, in which the imine product of structural Formula II is kept in aqueous solution as the sulfite adduct of structural Formula III en route to its conversion to the aminonitrile of structural Formula IV.

SCHEME 10

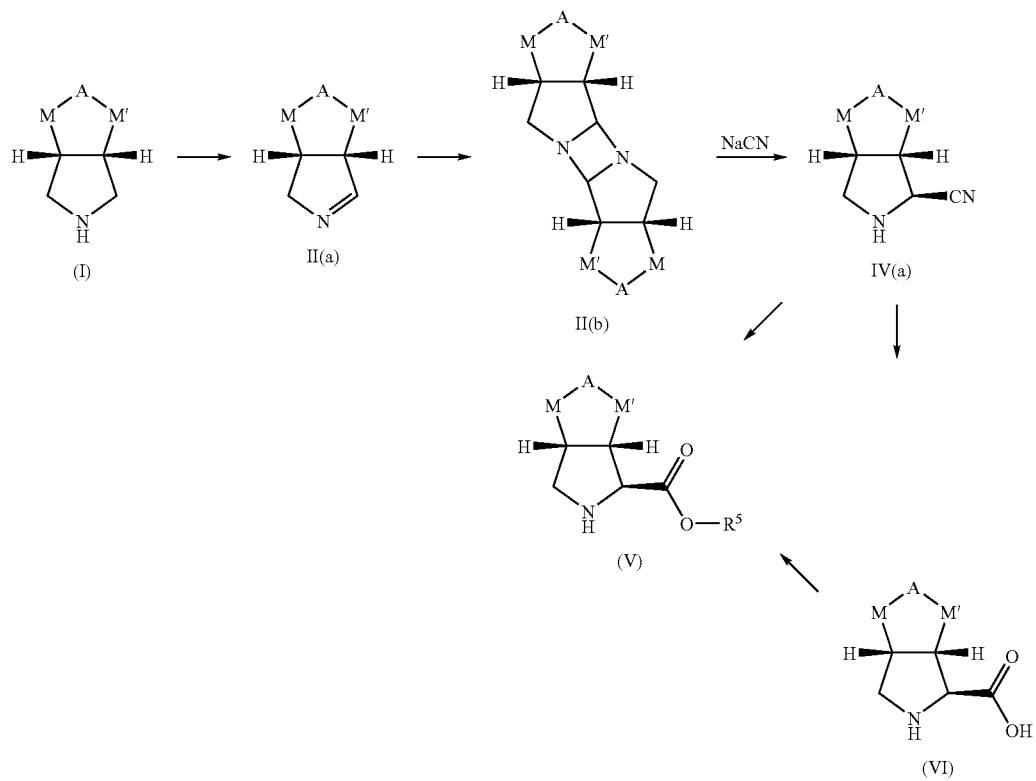

Scheme 10 depicts an overall process for the preparation of compounds according to structural Formulae V and VI from the secondary amines of structural Formula I, in which the imine product of structural Formula II is dimerized to the compound of structural Formula II(b) en route to its conversion to the aminonitrile of structural formula IV.

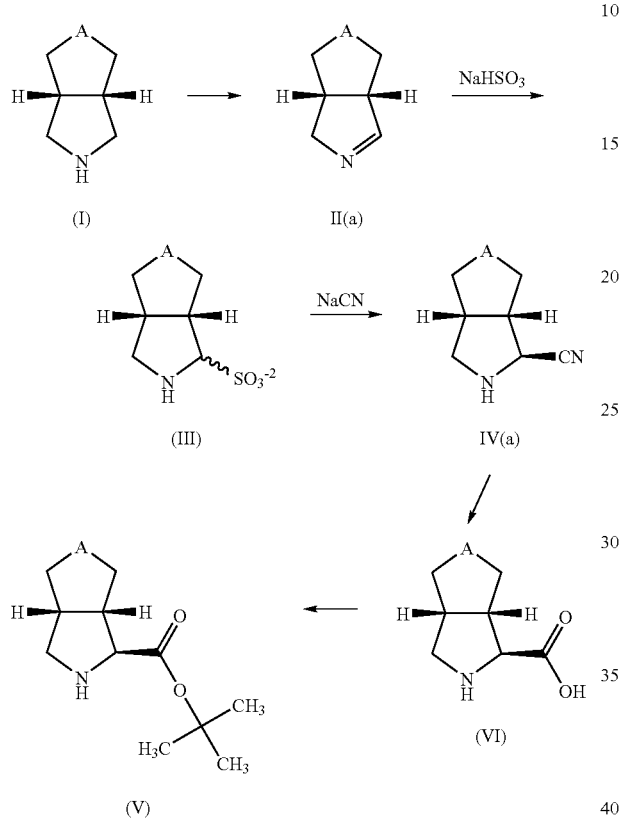

Scheme 11 depicts an overall process for the preparation of compounds according to structural Formula VI and structural Formula V (in which moiety $R^5$ is -t-butyl) from the secondary amines of structural Formula I that combines the reactions of Schemes 4 and 7.

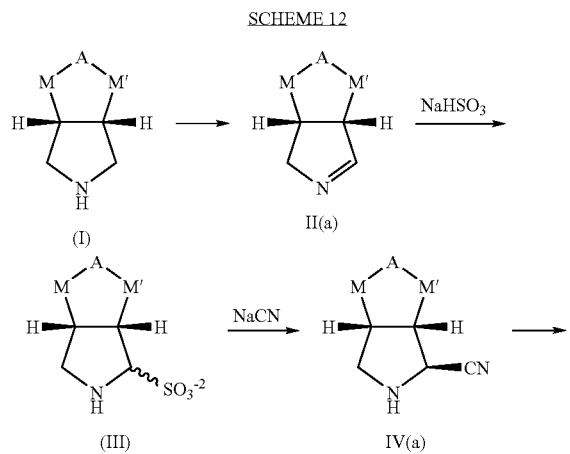

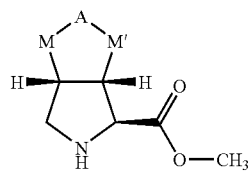

Scheme 12 depicts an overall process for the preparation of compounds according to structural Formula V (in which moiety $R^5$ is $CH_3$) from the secondary amines of structural Formula I that combines the reactions of Schemes 4 and 8.

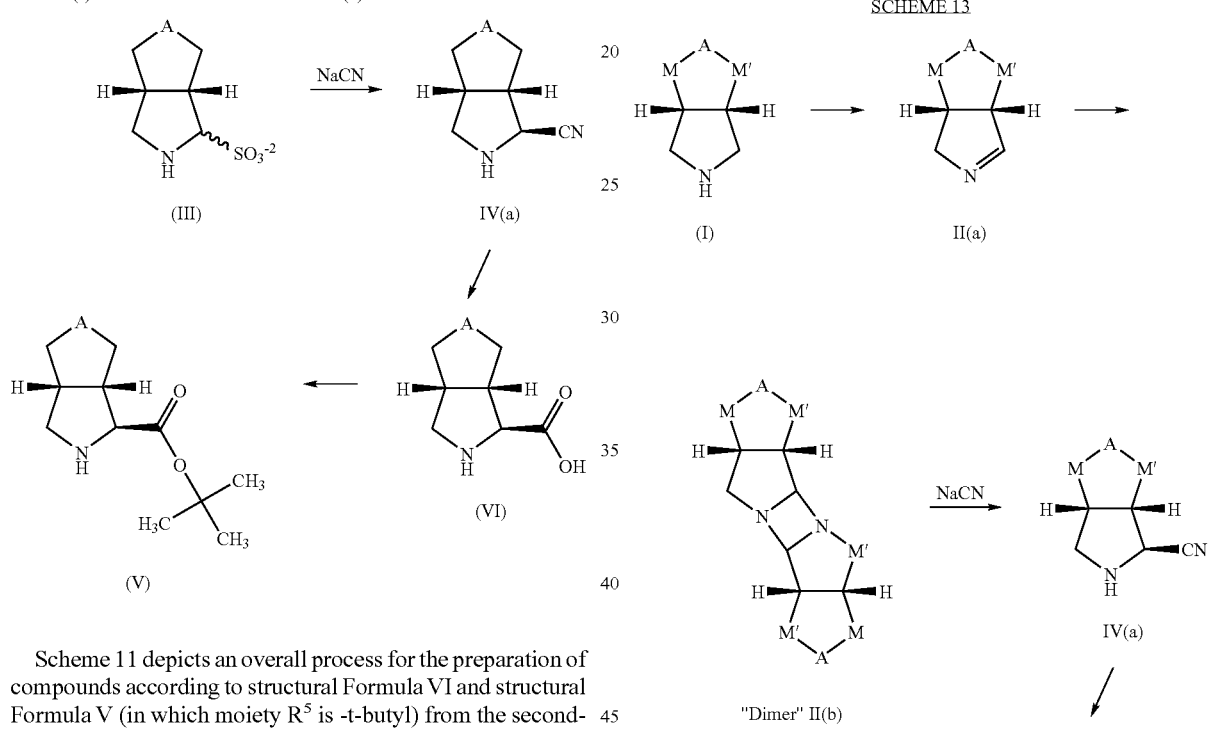

Scheme 13 depicts an overall process for the preparation of compounds according to structural Formula V (in which moiety $R^5$ is -t-butyl) from the secondary amines of structural Formula I that combines the reactions of Schemes 6 and 7.

SCHEME 14

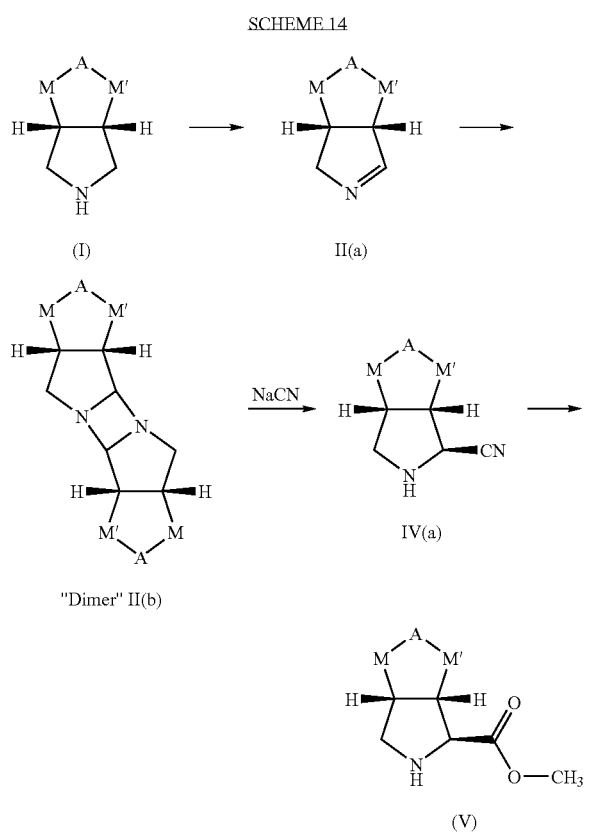

Scheme 14 depicts an overall process for the preparation of compounds according to structural Formula V (in which moiety $R^5$ is $CH_3$) from the secondary amines of structural Formula I that combines the reactions of Schemes 6 and 8.

SCHEME 15

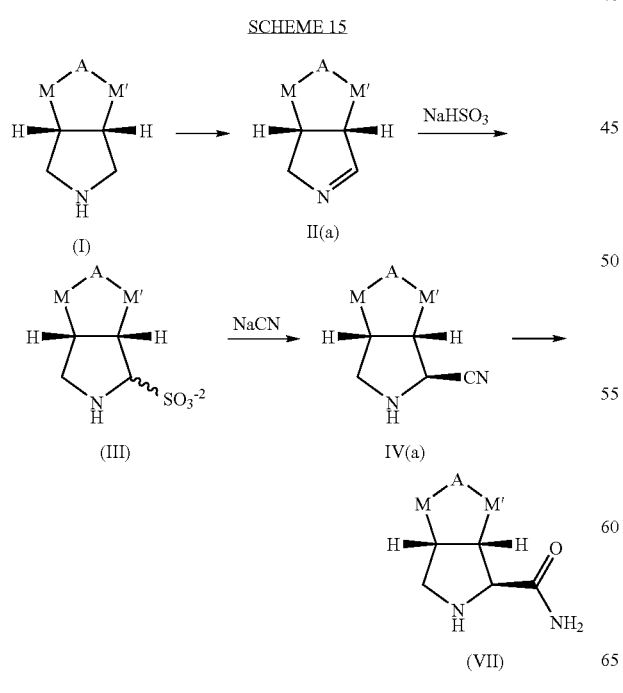

Scheme 15 depicts an overall process for the preparation of compounds according to structural Formula VII from the secondary amines of structural Formula I that includes the reactions of Scheme 4.

SCHEME 16

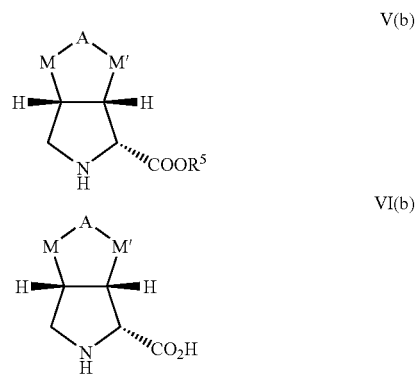

Scheme 16 depicts an overall process for the preparation of compounds according to structural Formula VII from the secondary amines of structural Formula I that includes the reactions of Scheme 6.

In another embodiment, any of the processes of Schemes 7-16 involving the trans-aminonitrile compounds of Formula IV(a) can be carried out with the cis-aminonitrile compounds of Formula IV(b). Where the reactions corresponding to Schemes 7-16 are carried using the cis-aminonitrile compounds of Formula IV(b), the resulting cis amino acids and amides of structural Formulae V(b), VI(b), and VII(b) are formed.

VII(b)

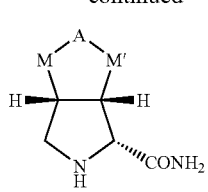

Without being bound by mechanism, it is recognized that an imidate intermediate forms during the reaction to form the compounds of structural Formulas V, VI, VII of Schemes 8, 9, 10, 11, 12, 13, 14, 15, and 16. Accordingly, in another embodiment the disclosure provide an imidate compound of structural Formula VIII, where $R^6$ is an H or an alkyl group.

VIII

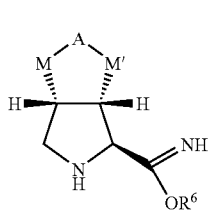

Accordingly, in some embodiments of the methods above, an imidate compound of structural Formula VIII can used in the preparation of a compound of structural Formula V, VI, and VII.

6.5 Monoamine Oxidase Enzymes

The present disclosure provides engineered monoamine oxidase enzymes that are capable of stereoselectively oxidizing or converting the substrate, a compound of structural Formula I to a compound of structural Formula II. In particular embodiments, the present disclosure provides engineered monoamine oxidase enzymes that are capable of stereoselectively oxidizing or converting the substrate, compound (1) to compound (2). In other embodiments, the present disclosure provides engineered monoamine oxidase enzymes that are capable of stereoselectively oxidizing or converting the substrate, compound (3) to compound (4). In both instances, a monoamine oxidase of present disclosure will also exhibit an improved property when compared with the naturally-occurring, wild-type monoamine oxidase of *Aspergillus niger* (SEQ ID NO:2) or *Aspergillus oryzae* (SEQ ID NO:32), or a hybrid thereof (SEQ ID NO:6) or when compared with other engineered monoamine oxidase enzyme (e.g. that of SEQ ID NO:8). Enzyme properties for which improvement is desirable include, but are not limited to, enzymatic activity, thermal stability, pH activity profile, cofactor requirements, refractoriness to inhibitors (e.g., product inhibition), sterospecificity, stereoselectivity, solvent stability, solubility, and stability and expression level within a host cell. The improvements can relate to a single enzyme property, such as enzymatic activity, or a combination of different enzyme properties, such as enzymatic activity and stereoselectivity.

The polynucleotide sequence encoding the naturally occurring monoamine oxidases of *Aspergillus niger* and *Aspergillus oryzae*, and thus the corresponding amino acid sequences, are available from Genbank accession no. L38858 for *Aspergillus niger*, and Genbank accession no. XM_001822832 for *Aspergillus oryzae*.

In some embodiments, the monoamine oxidases disclosed herein can have a number of modifications to the reference sequence (e.g., naturally occurring polypeptide or an engineered polypeptide) to result in an improved monoamine oxidase property. In such embodiments, the number of modifications to the amino acid sequence can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 20% of the total number of amino acids, or up to 30% of the total number of amino acids of the reference enzyme sequence. In some embodiments, the number of modifications to the naturally occurring polypeptide or an engineered polypeptide that produces an improved monoamine oxidase property may comprise from about 1-2, 1-3, 1-4, 1-5, 1-6, 1-7, 1-8, 1-9, 1-10, 1-15, 1-20, 1-21, 1-22, 1-23, 1-24, 1-25, or about 1-30 modifications on the reference sequence. The modifications can comprise insertions, deletions, substitutions, or combinations thereof.

In some embodiments, the modifications comprise amino acid substitutions to the reference sequence. Substitutions that can produce an improved monoamine oxidase property may be at one or more amino acids, 2 or more amino acids, 3 or more amino acids, 4 or more amino acids, 5 or more amino acids, 6 or more amino acids, 8 or more amino acids, 10 or more amino acids, or 20 or more amino acids, up to 10% of the total number of amino acids, up to 20% of the total number of amino acids, or up to 30% of the total number of amino acids of the reference enzyme sequence. In some embodiments, the number of substitutions to the naturally occurring polypeptide or an engineered polypeptide that produces an improved monoamine oxidases property can comprise from about 1-2, 1-3, 1-4, 1-5, 1-6, 1-7, 1-8, 1-9, 1-10, 1-15, 1-20, 1-21, 1-22, 1-23, 1-24, 1-25, or about 1-30 amino acid substitutions of the reference sequence.

In some embodiments, the improved property, as compared to wild-type or another engineered polypeptide, of the monoamine oxidase is with respect to an increase of its stereoselectivity i.e., herein, an increase in the stereometric excess of the product, for oxidizing a compound of structural Formula I to a compound of structural Formula II, or in particular embodiments, oxidizing or converting compound (1) to compound (2), or oxidizing compound (3) to compound (4). In some embodiments, the improved property of the monoamine oxidase is with respect to an increase in its ability to convert or reduce a greater percentage of the substrate to the product. In some embodiments, the improved property of the monoamine oxidase is with respect to an increase in its rate of conversion of the substrate to the product. This improvement in enzymatic activity can be manifested by the ability to use less of the improved monoamine oxidase as compared to the wild-type or other reference sequence to oxidize or convert the same amount of product. In some embodiments, the improved property of the monoamine oxidase is with respect to its stability or thermostability. In some embodiments, the monoamine oxidase has more than one improved property.

In some embodiments, a monoamine oxidase of the disclosure is capable of converting the substrate (1R,5S)-6,6-dimethyl-3-azabicyclo[3.1.0]hexane, compound (1) to (1R,5S)-6,6-dimethyl-3-azabicyclo[3.1.0]hex-2-ene, compound (2), with a percent stereometric excess of at least about 95% and at a rate that is improved over a reference polypeptide having the amino acid sequence of SEQ ID NO:2, SEQ ID NO:32 or SEQ ID NO:6. Exemplary polypeptides with such properties include, but are not limited to, polypeptides which comprise an amino acid sequence corresponding to SEQ ID NO: 4, 8 and 10.

In some embodiments, a monoamine oxidase of the disclosure is capable of converting the substrate (3aR,6aS)-octahydrocyclopenta[c]pyrrole, compound (3) to (3aS,6aR)-1,3a,4,5,6,6a-hexahydrocyclopenta[c]pyrrole, compound (4), with a percent diastereometric excess of at least about 95% and at a rate that is improved over a reference polypeptide having the amino acid sequence of SEQ ID NO:2, SEQ ID NO:32 or SEQ ID NO:6. Exemplary polypeptides with such properties include, but are not limited to, polypeptides which comprise an amino acid sequence corresponding to SEQ ID NO: 10, 14, 16, 18, 20, and 36.

Tables 2 and 3, below provide a list of the SEQ ID NOs disclosed herein with associated activities. The sequences below are based on the wild-type *Aspergillus niger* monoamine oxidase sequences (SEQ ID NO: 1 and 2) unless otherwise specified. In Tables 2 and 3 below, each row lists two SEQ ID NOs, where the odd number refers to the nucleotide sequence that codes for the amino acid sequence provided by the even number. The column listing the number of mutations (i.e., residue changes) refers to the number of amino acid substitutions as compared to the wild-type *Aspergillus niger* monoamine oxidase amino acid sequence of SEQ ID NO:1 and 2. Each Table is followed by a caption indicating the meaning of the symbols "+" "++" "+++" and "++++" in each context.

TABLE 2

List of Sequences and Corresponding Activity Improvement With Respect to the Conversion of Compound (1) to Compound (2):

| SEQ ID NO | Number of Changes Relative to A. niger (SEQ ID NO: 2) | Activity$^a$ | % ee$^b$ |
|---|---|---|---|
| 3/4 | 2 | + | +++ |
| 7/8 | 3 | +++ | +++ |
| 9/10 | 64 | ++++ | +++ |
| 11/12 | 65 | ++++++ | +++ |

$^a$Activity: + = 0-100%; ++ = 100-300%; +++ = 300-500%; ++++ = 500-1000%; +++++ = 1000-1500%; ++++++ = 1500-2000% of the activity of the engineered monoamine oxidase of *A. niger* (SEQ ID NO: 2) with respect to conversion of compound (1) to compound (2).
$^b$Enantioselectivity: +++ = 99-100% enantiomeric excess

TABLE 3

List of Sequences and Corresponding Activity Improvement With Respect to the Conversion of Compound (3) to Compound (4):

| SEQ ID NO | Number of Changes Relative to A. niger (SEQ ID NO: 2) | Activity$^a$ | % ee$^b$ |
|---|---|---|---|
| 9/10 | 64 | + | +++ |
| 13/14 | 65 | ++ | +++ |
| 15/16 | 66 | +++ | +++ |
| 17/18 | 67 | ++++ | +++ |
| 19/20 | 68 | ++++ | +++ |
| 35/36 | 67 | ++ | +++ |

$^a$Activity: + = 0-100%; ++ = 100-300%; +++ = 300-500%; ++++ = 500-1000%; of the activity of the engineered monoamine oxidase of *A. niger* of (SEQ ID NO: 8) with respect to conversion of compound (3) to compound (4). The wild type *A. niger* monoamine oxidase did not have a detectable level of activity on the substrate, compound (3).
$^b$Enantioselectivity: +++ = 99-100% enantiomeric excess In some embodiments, a monoamine oxidase of the disclosure comprises an amino acid sequence that is at least about 85%, 86%, 87%, 88%, 89%, 90%, 91%, 92%, 93%, 94%, 95%, 96%, 97%, 98%, or 99% identical as compared a reference sequence comprising the sequence of SEQ ID NO:2 with the proviso that the polypeptide comprises an amino acid sequence in which the amino acid residue corresponding to residue position 289 is a valine, the amino acid residue corresponding to residue position 348 is glutamine, the amino acid residue corresponding to residue position 382 is leucine, and the amino acid corresponding to residue 465 is glycine. In some embodiments, these monoamine oxidases can have one or more modifications to the amino acid sequence of SEQ ID NO: 12. The modifications can include substitutions, deletions, and insertions. The substitutions can be non-conservative substitutions, conservative substitutions, or a combination of non-conservative and conservative substitutions.

In some embodiments, a monoamine oxidase of the disclosure comprises an amino acid sequence that is at least about 85%, 86%, 87%, 88%, 89%, 90%, 91%, 92%, 93%, 94%, 95%, 96%, 97%, 98%, or 99% identical as compared a reference sequence comprising the sequence of SEQ ID NO:2 with the proviso that the polypeptide comprises an amino acid sequence in which the amino acid residue corresponding to residue position 289 is a valine, the amino acid residue corresponding to residue position 348 is glutamine, the amino acid residue corresponding to residue position 365 is tryptophan, and the amino acid corresponding to residue 465 is glycine. In some embodiments, these monoamine oxidases can have one or more modifications to the amino acid sequence of SEQ ID NO: 14. The modifications can include substitutions, deletions, and insertions. The substitutions can be non-conservative substitutions, conservative substitutions, or a combination of non-conservative and conservative substitutions.

In some embodiments, a monoamine oxidase of the disclosure comprises an amino acid sequence that is at least about 85%, 86%, 87%, 88%, 89%, 90%, 91%, 92%, 93%, 94%, 95%, 96%, 97%, 98%, or 99% identical as compared a reference sequence comprising the sequence of SEQ ID NO:2 with the proviso that the polypeptide comprises an amino acid sequence in which the amino acid residue corresponding to residue at position 99 is glutamic acid, the residue corresponding to residue 289 is a valine, the amino acid residue corresponding to residue position 348 is a glutamine, the amino acid residue corresponding to residue position 365 is tryptophan, and the amino acid residue corresponding to residue position 465 is glycine. In some embodiments, these monoamine oxidases can have one or more modifications to the amino acid sequence of SEQ ID NO: 16. The modifications can include substitutions, deletions, and insertions. The substitutions can be non-conservative substitutions, conservative substitutions, or a combination of non-conservative and conservative substitutions.

In some embodiments, a monoamine oxidase of the disclosure comprises an amino acid sequence that is at least about 85%, 86%, 87%, 88%, 89%, 90%, 91%, 92%, 93%, 94%, 95%, 96%, 97%, 98%, or 99% identical as compared a reference sequence comprising the sequence of SEQ ID NO:2 with the proviso that the polypeptide comprises an amino acid sequence in which the amino acid residue corresponding to residue position 99 is glutamic acid, the residue corresponding to position 135 is glutamine, the residue corresponding to residue 289 is valine, the amino acid residue corresponding to residue position 348 is a glutamine, the amino acid residue corresponding to residue position 365 is tryptophan, and the amino acid residue corresponding to residue position 465 is glycine. In some embodiments, these monoamine oxidases can have one or more modifications to the amino acid sequence of SEQ ID NO: 18. The modifications can include substitutions, deletions, and insertions. The substitutions can be non-conservative substitutions, conservative substitutions, or a combination of non-conservative and conservative substitutions In some embodiments, a monoamine oxidase of the disclosure comprises an amino acid sequence that is at least about 85%, 86%, 87%, 88%, 89%, 90%, 91%, 92%, 93%, 94%, 95%, 96%, 97%, 98%, or 99% identical as compared a reference sequence comprising the sequence of SEQ ID NO:2 with the proviso that the polypeptide comprises an amino acid sequence in which the amino acid residue corresponding to residue position 99 is glutamic acid, the residue corresponding to position 135 is glutamine, the residue corresponding to position 284 is aspartic acid, the residue corresponding to residue 289 is valine, the amino acid residue corresponding to residue position 348 is a glutamine, the amino acid residue corresponding to position 356 is valine, the amino acid residue corresponding to residue position 365 is tryptophan, and the amino acid residue corresponding to residue position 465 is glycine. In some embodiments, these monoamine oxidases can have one or more modifications to the amino acid sequence of SEQ ID NO: 20. The modifications can include substitutions, deletions, and insertions. The substitutions can be non-conservative substitutions, conservative substitutions, or a combination of non-conservative and conservative substitutions In some embodiments, an improved monoamine oxidases comprises an amino acid sequence that is at least about 85%, 86%, 87%, 88%, 89%, 90%, 91%, 92%, 93%, 94%, 95%, 96%, 97%, 98%, or 99% identical to the amino acid sequence corresponding to SEQ ID NO: 4, 8, 10, 12, 14, 16, 18, 20, or 36, as listed in Tables 2 and 3, wherein the improved monoamine oxidase amino acid sequence includes any one set of the specified amino acid substitution combinations presented in the amino acid sequences of Tables 2 and 3. In some embodiments, these monoamine oxidase can have additionally from about 1-2, 1-3, 1-4, 1-5, 1-6, 1-7, 1-8, 1-9, 1-10, or 1-20 mutations at other amino acid residues. The mutations can comprise insertions, deletions, or substitutions, or combinations thereof. In some embodiments, the additional mutations comprise conservative substitutions.

As will be appreciated by the skilled art, the polypeptides described herein are not restricted to the genetically encoded amino acids. In addition to the genetically encoded amino acids, the polypeptides described herein may comprise, either in whole or in part, naturally-occurring and/or synthetic non-encoded amino acids. Certain commonly encountered non-encoded amino acids which the monoamine oxidases described herein may comprise include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids that the monoamine oxidases described herein may comprise will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that the monoamine oxidases disclosed herein may also comprise amino acids or residues bearing side chain protecting groups. Non-limiting examples of such protected amino acids, which in this case belong to the aromatic category, include (protecting groups listed in parentheses), but are not limited to: Arg(tos), Cys (methylbenzyl), Cys (nitropyridinesulfenyl), Glu(δ-benzylester), Gln(xanthyl), Asn(N-δ-xanthyl), His(bom), His(benzyl), His(tos), Lys(fmoc), Lys(tos), Ser(O-benzyl), Thr (O-benzyl) and Tyr(O-benzyl).

Non-encoded amino acids that are conformationally constrained that the monoamine oxidases described herein may compose include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered monoamine oxidase can be targeted to a specific property of the enzyme.

6.6 Polynucleotides Encoding Engineered Monoamine Oxidases

In another aspect, the present disclosure provides polynucleotides encoding the engineered monoamine oxidases disclosed herein. The polynucleotides may be operatively linked to one or more heterologous regulatory sequences that control gene expression to create a recombinant polynucleotide capable of expressing the polypeptide. Expression constructs containing a heterologous polynucleotide encoding the engineered monoamine oxidase can be introduced into appropriate host cells to express the corresponding monoamine oxidase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved monoamine oxidase disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Tables 2 and 3.

In some embodiments, the polynucleotide comprises a nucleotide sequence encoding a monoamine oxidase with an amino acid sequence that has at least about 80% or more sequence identity, about 85% or more sequence identity, about 90% or more sequence identity, about 95% or more sequence identity, about 96% or more sequence identity, about 97% or more sequence identity, about 98% or more sequence identity, or 99% or more sequence identity to any of the reference engineered monoamine oxidase described herein. In some embodiments, the polynucleotides encode an engineered monoamine oxidase comprising an amino acid sequence selected from SEQ ID NO: 4, 8, 10, 12, 14, 16, 18, 20, or 36.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. By way of example, the polynucleotide of SEQ ID NO: 1 has been codon optimized for expression in *E. coli*, but otherwise encodes the naturally occurring monoamine oxidase of *Aspergillus niger*.

In certain embodiments, all codons need not be replaced to optimize the codon usage of the monoamine oxidase since the natural sequence will comprise preferred codons and because use of preferred codons may not be required for all amino acid residues. Consequently, codon optimized polynucleotides encoding the monoamine oxidases may contain preferred codons at about 40%, 50%, 60%, 70%, 80%, or greater than 90% of codon positions of the full length coding region.

In some embodiments, the polynucleotides encoding the engineered monoamine oxidases are selected from SEQ ID NO: 3, 7, 9, 11, 13, 15, 17, 19, or 35. In some embodiments, the polynucleotides are capable of hybridizing under highly stringent conditions to a polynucleotide comprising SEQ ID NO: 5 or 31, where the polynucleotide capable of hybridizing under highly stringent conditions encode a functional monoamine oxidase.

In other embodiments, the polynucleotides comprise polynucleotides that encode the monoamine oxidases described herein but have about 80% or more sequence identity, about 85% or more sequence identity, about 90% or more sequence identity, about 95% or more sequence identity, about 98% or more sequence identity, or 99% or more sequence identity at the nucleotide level to a reference polynucleotide encoding an engineered monoamine oxidase. In some embodiments, the reference polynucleotide is selected from polynucleotide sequences represented by SEQ ID NO: 3, 7, 9, 11, 13, 15, 17, 19, or 35.

An isolated polynucleotide encoding an improved monoamine oxidase may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, *Molecular Cloning: A Laboratory Manual*, $3^{rd}$ Ed., Cold Spring Harbor Laboratory Press; and *Current Protocols in Molecular Biology*, Ausubel. F. ed., Greene Pub. Associates, 1998, updates to 2006.

For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in *Scientific American*, 1980, 242:74-94; and in Sambrook et al., supra.

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8:423-488.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the methods disclosed herein.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase,

*Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5'-terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the methods disclosed herein. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, *Mol Cell Bio* 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the methods disclosed herein.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiol Rev* 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the monoamine oxidase of the present disclosure would be operably linked with the regulatory sequence.

Thus, in another embodiment, the present disclosure is also directed to a recombinant expression vector comprising a polynucleotide encoding an engineered monoamine oxidase or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present disclosure preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present disclosure preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori (as shown in the plasmid of FIG. 5) or the origins of replication of plasmids pBR322, pUC19, pACYC177 (which plasmid has the P15A ori), or pACYC184 permitting replication in *E. coli*, and pUB110, pE194, pTA1060, or pAM.beta.1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, *Proc Natl Acad. Sci. USA* 75:1433).

More than one copy of a nucleic acid sequence of the present disclosure may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the methods disclosed herein are commercially available. Suitable commercial expression vectors include p3xFLAGTM™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(-) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, *Gene* 57:193-201).

6.7 Host Cells for Expression of Monoamine Oxidases

In another aspect, the present disclosure provides a host cell comprising a polynucleotide encoding an improved monoamine oxidase of the present disclosure, the polynucleotide being operatively linked to one or more control sequences for expression of the monoamine oxidase in the host cell. Host cells for use in expressing the monoamine oxidase polypeptides encoded by the expression vectors of the present disclosure are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the monoamine oxidase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. The expression vector was created by operatively linking a polynucleotide encoding an improved monoamine oxidase into the plasmid pCK110900 operatively linked to the lac promoter under control of the laI repressor. The expression vector also contained the P15a origin of replication and the chloramphenicol resistance gene. Cells containing the subject polynucleotide in *Escherichia coli* W3110 were isolated by subjecting the cells to chloramphenicol selection.

6.8 Methods of Generating Engineered Monoamine Oxidases

In some embodiments, to make the improved monoamine oxidase polynucleotides and polypeptides of the present disclosure, the naturally-occurring monoamine oxidase that catalyzes the oxidation reaction is obtained (or derived) from *Aspergillus niger* or *Aspergillus oryzae*. In some embodiments, the parent polynucleotide sequence is codon optimized to enhance expression of the monoamine oxidase in a specified host cell. As an illustration, the parental polynucleotide sequence encoding the wild-type monoamine oxidase polypeptide of *Aspergillus niger* was constructed from oligonucleotides prepared based upon the known amino acid sequence of *Aspergillus niger* monoamine oxidase sequence available in Genbank database (Genbank accession no. L38858). The parental polynucleotide sequence, designated as SEQ ID NO: 1, was codon optimized for expression in *E. coli* and the codon-optimized polynucleotide cloned into an expression vector, placing the expression of the monoamine oxidase gene under the control of the lac promoter and laI repressor gene. Clones expressing the active monoamine oxidases in *E. coli* were identified and the genes sequenced to confirm their identity. The sequence designated (SEQ ID NO: 2) was the parent sequence utilized as the starting point for most experiments and library construction of engineered monoamine oxidases evolved from the *Aspergillus niger* monoamine oxidase.

The engineered monoamine oxidases can be obtained by subjecting the polynucleotide encoding the naturally-occurring monoamine oxidase to mutagenesis and/or directed evolution methods, as discussed above. An exemplary directed evolution technique is mutagenesis and/or DNA shuffling as described in Stemmer, 1994, *Proc Natl Acad Sci USA* 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, *Nat. Biotechnol.* 16:258-261), mutagenic PCR (Caldwell et al., 1994, *PCR Methods Appl.* 3:S136-S140), and cassette mutagenesis (Black et al., 1996, *Proc Natl Acad Sci USA* 93:3525-3529).

The clones obtained following mutagenesis treatment are screened for engineered monoamine oxidase having a desired improved enzyme property. Measuring enzyme activity from the expression libraries can be performed using standard biochemistry techniques, such as, but not limited to Monoamine oxidase activity can be measured using published methods, or adaptations thereof, for measuring monoamine oxidase, such as, but not limited to those disclosed by Zhou et al. (Zhou et al. "A One-Step Fluorometric Method for the Continuous Measurement of Monoamine Oxidase Activity," 1997 *Anal. Biochem.* 253:169-74) and Szutowicz et al. (Szutowicz et al., "Colorimetric Assay for Monoamine Oxidase in Tissues Using Peroxidase and 2,2'-Azino(3-ethylbenzthaizoline-6-sulfonic Acid) as Chromogen," 1984, *Anal. Biochem.* 138:86-94). Comparisons of enzyme activities are made using a defined preparation of enzyme, a defined assay under a set condition, and one or more defined substrates, as further described in detail herein or using the methods of, e.g., Zhou and Szutowicz. Generally, when lysates are compared, the numbers of cells and the amount of protein assayed are determined as well as use of identical expression systems and identical host cells to minimize variations in amount of enzyme produced by the host cells and present in the lysates. Where the improved enzyme property desired is thermal stability, enzyme activity may be measured after subjecting the enzyme preparations to a defined temperature and measuring the amount of enzyme activity remaining after heat treatments. Clones containing a polynucleotide encoding a monoamine oxidase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides disclosed herein can be prepared by chemical synthesis using, e.g., the classical phosphoramidite method described by Beaucage et al., 1981, *Tet Lett* 22:1859-69, or the method described by Matthes et al., 1984, *EMBO J.* 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., Operon Technologies Inc., Alameda, Calif., and many others.

Engineered monoamine oxidases expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis Mo.

Chromatographic techniques for isolation of the monoamine oxidase include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved monoamine oxidase. For affinity chromatography purification, any antibody which specifically binds the monoamine oxidase may be used. For the production of antibodies, various host animals, including but not limited to rabbits, mice, rats, etc., may be immunized by injection with a compound. The compound may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

6.9 Methods of Using the Engineered Monoamine Oxidases and Compounds Prepared Therewith The monoamine oxidases described herein can catalyze the oxidation of a substrate compound of structural Formula I to a stereoisomer product of structural Formula II(a):

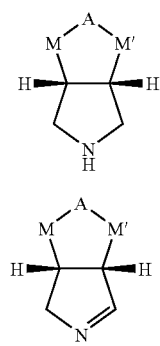

in which each A, M, and M' are as described above.

In a particular embodiment, monoamine oxidases described herein can catalyze the oxidation of the substrate (1R,5S)-6,6-dimethyl-3-azabicyclo[3.1.0]hexane, compound (1) to the stereoisomeric product, (1R,5S)-6,6-dimethyl-3-azabicyclo[3.1.0]hex-2-ene, compound (2):

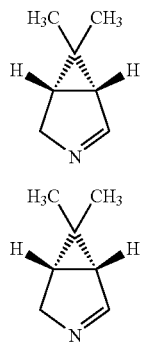

In some embodiments of this method for oxidizing the substrate, compound (1) to the product, compound (2), the monoamine oxidase polypeptide, as compared to the wild-type *A. niger* sequence of SEQ ID NO:2, must have at least the following amino acid substitutions: (1) residue 465 is glycine, (2) residue 289 is valine, (3) residue 384 is glutamine, and (4) residue 382 is leucine.

In another particular embodiment, monoamine oxidases described herein catalyze the oxidation of the substrate (3aR, 6aS)-octahydrocyclopenta[c]pyrrole, compound (3) to the stereoisomeric product, (3aS,6aR)-1,3a,4,5,6,6a-hexahydro-cyclopenta[c]pyrrole, compound (4), which can undergo further dimerization to form compound (5):

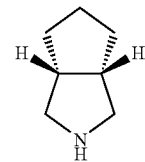

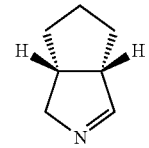

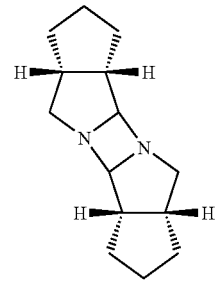

In one embodiment of this method for oxidizing the substrate, compound (3) to the product, compound (4), the monoamine oxidase polypeptide, as compared to the wild-type *A. niger* sequence of SEQ ID NO:1, must have at least one of the following amino acid substitutions: (1) residue 465 is glycine, (2) residue 289 is valine, (3) residue 384 is glutamine, and (4) residue 365 is tryptophan. In another embodiment of this method for reducing the substrate, compound (3) to the product, compound (4), the monoamine oxidase polypeptide, as compared to the wild-type *A. niger* sequence of SEQ ID NO:1, must have at least two of the following amino acid substitutions: (1) residue 465 is glycine, (2) residue 289 is valine, (3) residue 384 is glutamine, (4) residue 365 is tryptophan, and (3) residue 99 is glutamic acid. In another embodiment, the monoamine oxidase as compared to the wild-type *A. niger* sequence of SEQ ID NO:1, must have at least three of the following amino acid substitutions: (1) residue 465 is glycine, (2) residue 289 is valine, (3) residue 384 is glutamine, (4) residue 365 is tryptophan, (5) residue 99 is glutamic acid, and (4) residue 135 is glutamine. In a further embodiment, the monoamine oxidase as compared to the wild-type *A. niger* sequence of SEQ ID NO:1, must have at least the following amino acid substitutions: (1) residue 465 is glycine, (2) residue 289 is valine, (3) residue 99 is glutamic acid and (4) residue 135 is glutamine and/or residue 248 is aspartic acid.

In one embodiment of this method for oxidizing the substrate to the product, the substrate is oxidized to the product in greater than about 99% stereometric excess, wherein the monoamine oxidase comprises a sequence that corresponds to SEQ ID NO: 4, 8, 10, 12, 14, 16, 18, or 20.

In another embodiment of this method for reducing the substrate to the product, at least about 50% of the substrate is converted to the product in less than about 24 hours when carried out with greater than about 25 g/L of substrate and less than about 5 g/L of the polypeptide, wherein the polypeptide comprises an amino acid sequence corresponding to SEQ ID NO: 4, 8, 10, 12, 14, 16, 18, or 20.

In other embodiments, any one of the monamine oxidases provided herein can be used in the production of intermediates for the synthesis of Schering 505034 ((1R,2S,5S)—N-(4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide)), a protease inhibitor useful for the treatment of viral infections (Malcolm et al. (2006) *Antimicrob. Agents Chemother.* 50(3): 1013-20). An important step in the synthesis of Schering 505034 is the conversion of a compound of structural Formula I to the compound of structural Formula II, or more specifically, compound (1) to compound (2). Thus, the present disclosure provides methods for the production of Schering 505034, the methods comprising the step of converting compound (1) to compound (2) using a monoamine oxidase polypeptide of the disclosure. Methods disclosed herein for the production of Schering 505034 also may include one or more of the steps depicted and described in connection with Schemes 3, 4, 5, 6, 8, 9, 10, 12, and 14 above.

In other embodiments, any one of the monamine oxidases provided herein can be used in the production of intermediates for the synthesis of VX-950 ((N—((S)-1-cyclohexyl-2-((S)-1-((1S,3aR,6aS)-1-((R)-3-(2-(cyclopropylamino)-2-oxoacetyl)hexanoyl)hexahydrocyclopenta[c]pyrrol-2(1H)-yl)-3,3-dimethyl-1-oxobutan-2-ylamino)-2-oxoethyl)pyrazine-2-carboxamide, a protease inhibitor useful for the treatment of viral infections (Perni et al. (2006) *Antimicrob. Agents Chemother.* 50(3): 899-909). An important step in the synthesis of VX-950 is the conversion of a compound of structural Formula I to the compound of structural Formula II, or more specifically, compound (3) to compound (4). Thus, the present disclosure provides methods for the production of VX-950, the method comprising the step of converting compound (3) to compound (4) using a monoamine oxidase polypeptide of the disclosure. Methods disclosed herein for the production of VX-950 also may include one or more of the steps depicted and described in connection with Schemes 3, 4, 5, 6, 7, 9, 10, 11, and 13 above.

As is known by those of skill in the art, monoamine oxidase-catalyzed oxidase reactions typically require a cofactor. Oxidation reactions catalyzed by the monoamine oxidases described herein also typically require a cofactor, flavin-adenine nucleotide (FAD). As used herein, the term "cofactor" refers to a non-protein compound that operates in combination with a monoamine oxidase. Generally, the oxidized form of the cofactor, which may be non-covalently or covalently attached to the monoamine oxidase, is added to the reaction mixture. The oxidized FAD form can be regenerated from the reduced form FAD-$H_2$ by molecular oxygen. In other embodiments, the oxidized FAD form could be regenerated by NAD(P) to provide FAD and NAD(P)H. The NAD(P) could, in turn, be regenerated by reduction of a ketone to an alcohol using an NAD(P)H-dependent alcohol dehydrogenase/ketone reductase.

The monoamine oxidase-catalyzed oxidation reactions described herein are generally carried out in a solvent. Suitable solvents include water, organic solvents (e.g., ethyl acetate, butyl acetate, 1-octacnol, heptane, octane, methyl t-butyl ether (MTBE), toluene, and the like), and ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, are used.

Exemplary aqueous co-solvent systems have water and one or more organic solvent. In general, an organic solvent component of an aqueous co-solvent system is selected such that it does not completely inactivate the monoamine oxidase enzyme. Appropriate co-solvent systems can be readily identified by measuring the enzymatic activity of the specified engineered monoamine oxidase enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel.

The aqueous solvent (water or aqueous co-solvent system) may be pH-buffered or unbuffered. Generally, the oxidation can be carried out at a pH of about 10 or below, usually in the range of from about 5 to about 10. In some embodiments, the oxidation is carried out at a pH of about 9 or below, usually in the range of from about 5 to about 9. In some embodiments, the oxidation is carried out at a pH of about 8 or below, often in the range of from about 5 to about 8, and usually in the range of from about 6 to about 8. The oxidation may also be carried out at a pH of about 7.8 or below, or 7.5 or below. Alternatively, the oxidation may be carried out a neutral pH, i.e., about 7.

During the course of the oxidation reactions, the pH of the reaction mixture may change. Typical amines of structural Formula I are protonated at and about neutral pH, while the imine products of structural Formula II are typically not protonated at and about neutral pH. Accordingly, in typical embodiments wherein the reaction is conducted at or about neutral pH, the oxidation of the protonated amine to the un-protonated imine releases a proton into the aqueous solution. The pH of the reaction mixture or may be maintained at a desired pH or within a desired pH range by the addition of a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer, and the like. Combinations of buffering or base addition may also be used.

Suitable bases for neutralization of acid are organic bases, for example amines, alkoxides and the like, and inorganic bases, for example, hydroxide salts (e.g., NaOH), carbonate salts (e.g., $NaHCO_3$), bicarbonate salts (e.g., $K_2CO_3$), basic phosphate salts (e.g., $K_2HPO_4$, $Na_3PO_4$), and the like. A preferred base for the neutralizing protons released from oxidation of the amine to the imine over the course of the reaction is the amine substrate itself. The addition of a base concurrent with the course of the conversion may be done manually while monitoring the reaction mixture pH or, more conveniently, by using an automatic titrator as a pH stat. A combination of partial buffering capacity and base addition can also be used for process control. Typically, bases added to unbuffered or partially buffered reaction mixtures over the course of the oxidation are added in aqueous solutions.

In carrying out the stereoselective oxidation reactions described herein, the engineered monoamine oxidases may be added to the reaction mixture in the form of the purified enzymes, whole cells transformed with gene(s) encoding the monoamine oxidase, and/or cell extracts and/or lysates of such cells. Whole cells transformed with gene(s) encoding the engineered monoamine oxidase or cell extracts and/or lysates thereof, may be employed in a variety of different forms, including solid (e.g., lyophilized, spray-dried, and the like) or semisolid (e.g., a crude paste).

The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small portions, then added to a prechilled lyophilization chamber, followed by the application of a vacuum. After the removal of water from the samples, the temperature is typically raised to 4° C. for two hours before release of the vacuum and retrieval of the lyophilized samples.

The quantities of reactants used in the oxidation reaction will generally vary depending on the quantities of product desired, and concomitantly the amount of monoamine oxidase substrate employed. Generally, substrates can be employed at a concentration of about 5 grams/liter to 50 grams/liter using from about 50 mg/liter to about 5 g/liter of monoamine oxidase. Those having ordinary skill in the art will readily understand how to vary these quantities to tailor them to the desired level of productivity and scale of production. Appropriate quantities of optional agents, such as catalase, antifoam, and sodium bisulfite or sodium metabisulfite may be readily determined by routine experimentation.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. In certain embodiments, one or more of the components of the reaction may be added continuously ("fed") to the reaction at levels that minimize or obviate substrate and/or product inhibition of the monoamine oxidase. In certain embodiments, the monoamine oxidase can be added at intervals over the course of the reaction, for example addition at about every 1 hour, about every 2 hours, about every 3 hours, or about every 4 hours.

Suitable conditions for carrying out the monoamine oxidase catalyzed oxidation reactions described herein include a wide variety of conditions which can be readily optimized by routine experimentation that includes, but is not limited to, contacting the engineered monoamine oxidase and substrate at an experimental pH and temperature and detecting product, for example, using the methods described in the Examples provided herein.

The monoamine oxidase catalyzed oxidation is typically carried out at a temperature in the range of from about 5° C. to about 75° C. For some embodiments, the reaction is carried out at a temperature in the range of from about 20° C. to about 55° C. In still other embodiments, it is carried out at a temperature in the range of from about 20° C. to about 45° C., about 30° C. to about 45° C., or about 40° C. to about 45° C. The reaction may also be carried out under ambient conditions (about 21° C.).

The oxidation reaction is generally allowed to proceed until essentially complete, or near complete, oxidation of substrate is obtained. Oxidation of substrate to product can be monitored using known methods by detecting substrate and/or product. Suitable methods include gas chromatography, HPLC, and the like. Conversion yields are generally greater than about 50%, may also be greater than about 60%, may also be greater than about 70%, may also be greater than about 80%, may also be greater than 90%, and are often greater than about 97%.

7. EXAMPLES

Various features and embodiments of the disclosure are illustrated in the following representative examples, which are intended to be illustrative, and not limiting.

Example 1

Wild-Type Monoamine Oxidase Gene Acquisition and Construction of Expression Vectors Monoamine oxidase encoding genes were designed for expression in *E. coli* (W3110fhuA or UM2) based on the reported amino acid sequence of the monoamine oxidase and a codon optimization algorithm as described in Example 1 of U.S. provisional application Ser. No. 60/848,950, incorporated herein by reference. Genes were synthesized using oligonucleotides composed, e.g., of 42 nucleotides and cloned into expression vector pCK110900 (depicted as FIG. 3 in United States Patent Application Publication 20060195947) under the control of a lac promoter. The expression vector also contains the P15a origin of replication and the chloramphenicol resistance gene. Resulting plasmids were transformed into *E. coli* W3110 using standard methods. Examples of codon optimized genes and the encoding polypeptides as well are listed in Table 4. The activity of the wild-type monoamine oxidases was confirmed using methods know in the art, or adapted therefrom, including those disclosed by Zhou et al. (Zhou et al. "A One-Step Fluorometric Method for the Continuous Measurement of Monoamine Oxidase Activity," 1997 Anal. Biochem. 253:169 74) and Szutowicz et al. (Szutowicz et al., "Colorimetric Assay for Monoamine Oxidase in Tissues Using Peroxidase and 2,2' Azino(3 ethylbenzthaizoline-6-sulfonic Acid) as Chromogen," 1984, *Anal. Biochem.* 138:86-94). Comparisons of enzyme activities were made using a defined preparation of enzyme, a defined assay under a set condition, and one or more defined substrates, as further described in detail herein or using the methods of, e.g., Zhou and Szutowicz. Generally, when lysates were compared, the numbers of cells and the amount of protein assayed were determined as well as the use of identical expression systems and identical host cells to minimize variations in amount of enzyme produced by the host cells and present in the lysates.

TABLE 4

Abbreviations, Source and Citations for Representative Monoamine Oxidases

| Monoamine Oxidase | Microorganism from which enzyme was originally identified | Genbank Accession No. | GI Number | Polynucleotide SEQ ID NO | Polypeptide SEQ ID NO |
|---|---|---|---|---|---|
| MAON | *Aspergillus niger* | L38858 | 619754 | 1 | 2 |
| MAO3 | *Aspergillus oryzae* | XM_001822832 | 169776835 | 31 | 32 |

Polynucleotides encoding engineered monamine oxidases of the present disclosure are likewise cloned into vector pCK110900 for expression in *E. coli* W3110.

Example 2

Production of Monoamine Oxidase Powders; Shake Flask Procedure

Monoamine oxidase powders were produced from shake flask cultures as follows: A single microbial colony of *E. coli* containing a plasmid with the monoamine oxidase gene of interest is inoculated into 50 ml Luria Bertani broth containing 30 μg/ml chloramphenicol and 1% glucose. Cells are grown overnight (at least 16 hrs) in an incubator at 30° C. with shaking at 250 rpm. The culture is diluted into 250 ml 2XYT (16 g/L bacto-tryptone, 10 g/L yeast extract, 5 g/L NaCl, pH 7.0), 1 mM MgSO$_4$, 30 μg/ml chloramphenicol in a 1 liter flask to an optical density at 600 nm (OD600) of 0.2 and allowed to grow at 30° C. Expression of the monoamine oxidase gene is induced with 1 mM IPTG when the OD600 of the culture is 0.6 to 0.8 and incubated overnight (at least 16 hrs). Cells are harvested by centrifugation (5000 rpm, 15 min, 4° C.) and the supernatant discarded. The cell pellet is resuspended with an equal volume of cold (4° C.) 100 mM triethanolamine (hydrochloride) buffer, pH 7.0 (optionally including 2 mM MgSO$_4$), and harvested by centrifugation as above. The washed cells are re-suspended in two volumes of the cold triethanolamine (hydrochloride) buffer, pH 7.0 and passed through a French Press twice at 12000 psi while maintaining the temperature at 4° C. Cell debris is removed by centrifugation (9000 rpm, 45 min., 4° C.). The clear lysate supernatant is collected and stored at −20° C. Lyophilization of frozen clear lysate provides a dry powder of crude monoamine oxidase enzyme.

Example 3

Production of Monoamine Oxidase; Fermentation Procedure

Monoamine oxidase powders were produced by fermentation as follows: In an aerated agitated 15 L fermenter, 6.0 L of growth medium containing 0.88 g/L ammonium sulfate, 0.98 g/L of sodium citrate; 12.5 g/L of dipotassium hydrogen phosphate trihydrate, 6.25 g/L of potassium dihydrogen phosphate, 6.2 g/L of Tastone-154 yeast extract, 0.083 g/L ferric ammonium citrate, and 8.3 ml/L of a trace element solution containing 2 g/L of calcium chloride dihydrate, 2.2 g/L of zinc sulfate heptahydrate, 0.5 g/L manganese sulfate monohydrate, 1 g/L cuprous sulfate heptahydrate, 0.1 g/L ammonium molybdate tetrahydrate and 0.02 g/L sodium tetraborate decahydrate are brought to a temperature of 30° C. The fermenter is inoculated with a late exponential culture of *E. coli* W3110, containing a plasmid with the monoamine oxidase gene of interest, grown in a shake flask as described in Example 3 to a starting OD600 of 0.5 to 2.0. The fermenter is agitated at 500 1500 rpm and air is supplied to the fermentation vessel at 1.0-15.0 L/min to maintain dissolved oxygen level of 30% saturation or greater. The pH of the culture is controlled at 7.0 by addition of 20% v/v ammonium hydroxide. Growth of the culture is maintained by the addition of a feed solution containing 500 g/L cerelose, 12 g/L ammonium chloride and 10.4 g/L magnesium sulfate heptahydrate. Once the culture reaches an OD600 of 50, expression of monoamine oxidase is induced by the addition of isopropyl-β-D-thiogalactoside (IPTG) to a final concentration of 1 mM. The culture is then grown for another 14 hours. The culture is chilled to 4° C. and maintained at 4° C. until harvested. Cells are harvested by centrifugation at 5000G for 40 minutes in a Sorval RC12BP centrifuge at 4° C. Harvested cells are used directly in the following downstream recovery process or are stored at 4° C. until such use.

Where the cells are to be used directly in the downstream recovery process, the cell pellet is resuspended in 2 volumes of 100 mM triethanolamine (hydrochloride) buffer, pH 6.8, at 4° C. to each volume of wet cell paste. The intracellular monoamine oxidase is released from the cells by passing the suspension through a homogenizer fitted with a two-stage homogenizing valve assembly using a pressure of 12000 psig. The cell homogenate is cooled to 4° C. immediately after disruption. A solution of 10% w/v polyethyleneimine, pH 7.2, is added to the lysate to a final concentration of 0.5% w/v and stirred for 30 minutes. The resulting suspension is clarified by centrifugation at 5000G in a standard laboratory centrifuge for 30 minutes. The clear supernatant is decanted and concentrated ten times using a cellulose ultrafiltration membrane with a molecular weight cut off of 30 Kd. The final concentrate is dispensed into shallow containers, frozen at −20° C. and lyophilized to powder. The monoamine oxidase powder is stored at −80° C.

Example 4

Analytical Methods for the Conversion of 6,6-dimethyl-3-azabicyclo[3.1.0]hexane, Compound (1) to (1R,5S)-6,6-dimethyl-3-azabicyclo[3.1.0]hex-2-ene, Compound (2)

The conversion of 6,6-dimethyl-3-azabicyclo[3.1.0]hexane and the stereometric purity of the 6,6-dimethyl-3-azabicyclo[3.1.0]hex-2-ene product were determined by the chiral GC method described below. The order of elution was: substrate (1) (retention time ~7 min), the desired (1R,2S)-imine (2) (~10.6 min), the undesired (1S,2R) imine (~11.0 min) Column: Supelco Betadex 225 (part#24348), 0.25 mm×30 m×0.25 um; Oven Temperature: 85° C. Isothermal; Carrier Flow: 1.1 ml/min; Injection volume: 4 μL; and Injection Split: 100:1; Injector temperature=200° C.; FID detection.

Example 5

Analytical Methods for the Conversion of octahydrocyclopenta[c]pyrrole, Compound (3) to (3aS,6aR)-1,3a,4,5,6,6a-hexahydrocyclopenta[c]pyrrole, Compound (4)

The conversion of octahydrocyclopenta[c]pyrrole and the stereometric purity of the product were determined using the chiral GC method described below. The order of elution was: substrate (3) (retention time ~2.7 min), the desired (3aS,6aR) imine (4) (~5.5 min), the undesired (3aR,6aS)-imine (~5.8 min). The imine dimer of imine (4) thermolyzes to the imine in the injector port. Column: Supelco Betadex 225 (part#24348), 0.25 mm×30 m×0.25 um; Oven Temperature: 120° C. Isothermal; Carrier Flow: 1.1 ml/min; Injection volume: 4 µL; and Injection Split: 100:1; Injector temperature=200° C.; FID detection.

Example 6

Evaluation of Wild-Type Monoamine Oxidases for Oxidation of 6,6-dimethyl-3-azabicyclo[3.1.0]hexane, Compound (1)

Wild-type monoamine oxidases disclosed herein were screened for their ability to oxidize 6,6 dimethyl-3-azabicyclo[3.1.0]hexane, compound (1) to 6,6-dimethyl-3-azabicyclo[3.1.0]hex-2-ene, compound (2). To a 50-mL 3-neck flask under air were added 25 mL of 100 mM pH 3.0 potassium phosphate buffer and 330 µL of 6,6-dimethyl-3-azabicyclo[3.1.0]hexane to give homogeneous solution. The pH was adjusted to approximately 7.3 via conc. $H_3PO_4$. To the pH adjusted solution was added 60 µL of *A. niger* catalase suspension (Sigma Aldrich; catalog number C-3515) and 150 mg of wild-type monoamine oxidase powder (prepared by the shake flask method of Example 2) with SEQ ID NO 2 (*A. niger*) or SEQ ID NO 32 (*A. oryzae*) in pH 8.0 potassium phosphate buffer. The resulting pale yellow solution was stirred under air for 24 hours. The pH was maintained at 7.2 via feedback controlled addition of 1 N NaOH in 1-5 µL portions. (The amine reactant is protonated at neutral pH; the imine product is not. The action releases a proton which must be neutralized to maintain the pH).

The reactions quenched with 10 N NaOH to bring the pH to approximately 14 and the mixture was extracted with CDCl3 using centrifugation for phase separation. $^1$H-NMR analysis of the $CDCl_3$ solution from the reaction using the *A. niger* wild type monoamine oxidase indicated ~20% conversion of the amine (1) to the imine (2). The reaction with the *A. oryzae* wild type monoamine oxidase consumed about twice the amount of the NaOH solution as the reaction with the *A. niger* wild type monoamine oxidase, indicating about twice the amount of amine (1) was converted.

Chiral GC analysis according to the method of Example 4 showed the desired (1R,5S)-imine (2). The undesired (1S,5R)-imine enantiomer was not detected.

This example demonstrates that these wild-type monoamine oxidases have a low activity on 6,6 dimethyl-3-azabicyclo[3.1.0]hexane, compound (1) and convert it to the desired (1R,5S)-imine (2).

Example 7

Evaluation of a Wild-Type Monoamine Oxidase for Oxidation of Octahydrocyclopenta[c]pyrrole, Compound (3)

Wild-type monoamine oxidases disclosed herein were screened for their ability to oxidize (octahydrocyclopenta[c]pyrrole, compound (3) to (3aS,6aR) 1,3a,4,5,6,6a hexahydrocyclopenta[c]pyrrole), compound (4). To a 50-mL 3-neck flask under air were added 25 mL of 100 mM pH 8.0 potassium phosphate buffer and 375 mg of octahydrocyclopenta[c]pyrrole hydrochloride and the pH was adjusted to approximately 7.3 with 1 N NaOH. To the pH adjusted solution was added 60 µL of *A. niger* catalase suspension (purchased from Sigma Aldrich; catalog number C-3515) and 150 mg of wild type monoamine oxidase powder (prepared by the shake flask method of Example 2) with SEQ ID NO 2 (*A. niger*) in pH 8.0 potassium phosphate buffer. The resulting pale yellow solution was stirred under air for 24 hours. The pH was maintained at 7.2 via feedback controlled addition of 1 N NaOH in 1-5 µL portions. Little or no NaOH consumption was observed after 24 hours. The reaction was quenched with 10 N NaOH to bring the pH to approximately 14 and the mixture was extracted with $CDCl_3$. After phase separation via centrifuge (6000 rpm for 5 minutes), $^1$H-NMR analysis of the $CDCl_3$ solution indicated little or no conversion of the amine (3) to the imine (4).

This example demonstrates that wild-type monoamine oxidases have very little if any activity on octahydrocyclopenta[c]pyrrole, compound (3).

Example 8

High Throughput Assays for Monoamine Oxidase Activity on 6,6-dimethyl-3-azabicyclo[3.1.0]hexane, Compound (1)

Plasmid libraries obtained by directed evolution and containing evolved monoamine oxidase genes are transformed into *E. coli* and plated on Luria-Bertani (LB) broth containing 1% glucose and 30 µg/mL chloramphenicol (CAM). After incubation for at least 16 hrs at 30° C., colonies are picked using a Q-bot® robotic colony picker (Genetix USA, Inc., Beaverton, Oreg.) into 96-well shallow well microtiter plates containing 180 µL Terrific broth (TB), 1% glucose, 30 µg/mL chloramphenicol (CAM), and 2 mM $MgSO_4$. Cells are grown overnight at 30° C. with shaking at 200 rpm. 20 µL of this culture was then transferred into 96-deep well plates containing 350 µL Terrific broth (TB), 2 mM $MgSO_4$ and 30 µg/mL CAM. After incubation of deep-well plates at 30° C. with shaking at 250 rpm for 2.5 to 3 hours (OD600 0.6-0.8), recombinant gene expression by the cell cultures is induced by addition of isopropyl βD thiogalactoside (IPTG) to a final concentration of 1 mM. The plates are then incubated at 30° C. with shaking at 250 rpm for 15-23 hrs.

Cells were pelleted by centrifugation, resuspended in 400 µL lysis buffer and lysed by shaking at room temperature for at least 2 hours. The lysis buffer contained 50 mM sodium phosphate buffer, pH 7.0, 1 mg/mL lysozyme and 500 µg/mL polymixin B sulfate. Cell debris was pelleted by centrifugation.

Monoamine oxidase activity was measured by transferring 20 µL appropriately diluted clear lysate supernatant into the wells of 96-deep-well microtiter plates with 180 µL of an assay mixture containing 50 mM sodium phosphate buffer (pH 7.5), 4 U/ml *A. niger* catalase (Sigma-C3515) and 40 mM 6,6-dimethyl-3-azabicyclo[3.1.0]hexane provided as its acetic acid salt. The assay plates were sealed and shaken at room temperature for 4 hours. The reactions were quenched by addition of 500 µL 1:1 acetonitrile:water and the plates were centrifuged. After centrifugation, 150 µL of the supernatant was transferred to a shallow plate for HPLC analysis by the method of according to Example 4.

HPLC conditions: 2.1×75 mm Zorbax Eclipse XDB C-18 3.5 micron particle size column at 40° C. with a mobile phase of 60:40 40 mM ammonium acetate/acetonitrile at 0.5 mL/min. The imine eluted at ~1 minute (254 nm). Only the imine can be detected and the activity ranking of the variants was done using absolute peak area of the imine signal.

Alternatively, the assay reactions were quenched with 100 µL of 10 N NaOH and extracted with 1:1 v/v MTBE and subjected to chiral GC analysis by the method of Example 4.

Example 9

High Throughput Assays for Monoamine Oxidase Activity on Octahydrocyclopenta[c]pyrrole, Compound (3)

Lysates containing monoamine oxidase variants on 96-well plates were prepared as described in Example 8.

Monoamine oxidase activity was measured by transferring 50 µL clear lysate into the wells of 96-deep-well microtiter plates with 450 µL of an assay mixture containing 100 mM sodium phosphate buffer (pH 7.5), 4 U/ml *A. niger* catalase (Sigma-C3515) and 50 mM octahydrocyclopenta[c]pyrrole. The assay plates were sealed and shaken at room temperature for 16 hours. The plates were centrifuged and 100 µL of the supernatant was quenched into 100 µL of acetonitrile in the wells of a shallow well plate for HPLC analysis according to Example 5.

The reactions were quenched by addition of 100 µL acetonitrile and the plates were centrifuged. After centrifugation, 100 µL of the supernatant was 100 µL of acetonitrile and transferred to a shallow plate for HPLC analysis by the method according to Example 4.

HPLC conditions: 2.1×75 mm Zorbax Eclipse XDB C-18 3.5 micron particle size column at 40° C. with a mobile phase of 70:30 40 mM ammonium acetate/acetonitrile at 0.5 mL/min. The imine eluted at ~1.3 minute (254 nm). Only the imine can be detected and the ranking of the variants were done using absolute peak area of the imine signal.

Alternatively, the reaction was quenched with 100 µL of 10 N NaOH and extracted with 1:1 v/v MTBE and subjected to chiral GC analysis Example 5.

This example describes the method that was used to identify monoamine oxidase variants improved for oxidation of octahydrocyclopenta[c]pyrrole, Compound (3).

Example 10

Preparative Scale Production of (1R,5S)-6,6-dimethyl-3-azabicyclo[3.1.0]hex-2-ene, Compound (2)

To a 500-mL 4-neck flask fitted with an overhead stirrer at 300 rpm was added 150 mL of Milli-Q water at about 25° C., and 1.2 mL (approximately 1.0 g; approximately 9 mmol) of 6,6-dimethyl-3-azabicyclo[3.1.0]hexane to give a homogeneous solution with a pH of 11.8. $Na_2S_2O_5$ was added portion-wise until pH 7.5 was reached. To the colorless solution was added 300 µL of an Antifoam-204 (Sigma catalog number A-6226) and 600 µL of *A. niger* catalase suspension (Sigma Aldrich; catalog number C-3515) to give a colorless solution at pH 7.5. To this solution was added 1.5 g of a monoamine oxidase powder (produced by fermentation according to Example 3) with SEQ ID NO 10 to give a yellow solution. An air sparging probe was inserted (airflow rate ~60 mL/min) and the pH of the reaction mixture began to drop immediately. The pH was maintained via feedback controlled dosing of 2 N NaOH. After approximately 30 minutes, the pH remained stable and no further base dosing occurred. After an additional 10 minutes (40 minutes total), 120 mL of 6,6-dimethyl-3-azabicyclo[3.1.0]hexane $NaHSO_3$ solution (prepared by adding 20.8 g of 6,6-dimethyl-3-azabicyclo[3.1.0] hexane to 150 mL of $dH_2O$ and adding enough $Na_2S_2O_5$ to reach pH 7.2) was added to the reaction at a rate of 0.25 mL/min. The pH of the reaction mixture began to drop immediately and dosing of 2 N NaOH resumed. The addition of the solution of 6,6-dimethyl-3-azabicyclo[3.1.0]hexane and $NaHSO_3$ was completed after approximately 8 hours (9 hours of total reaction time). The base addition continued and the base addition rate increased after the substrate addition was completed. A 200 µL aliquot was taken, quenched with 200 µL of 8 N NaOH (to break the aminosulfonate to the free imine) and extracted with 600 µL of $CDCl_3$. $^1$H-NMR analysis of the $CDCl_3$ extract showed complete conversion of the substrate (1) to azabicyclo[3.1.0]hex-2-ene compound (2) ($^1$H-NMR (300 MHz, $CDCl_3$) spectrum: δ 7.42 (s, 1H, N=C—H), 3.81 (dd; J=6.1, 17.8; 1H), 3.50 (dd; J=2.1, 17.8; 1H), 2.06 (m; 1H), 1.62 (m, 1H), 1.03 (s, 3), 0.80 (s, 3H)).

Chiral GC analysis showed the (1R,5S) enantiomer (2) with no detectable (1S,2R) enantiomer.

The reaction mixture was used "as is" for the cyanation reaction to the aminonitrile).

Example 11

Monoamine Oxidase Catalyzed Desymmetrization of 6,6-dimethyl-3-azabicyclo[3.1.0]hexane (1) to (1R, 5S)-6,6-dimethyl-3-azabicyclo[3.1.0]hex-2-ene (2) Under a Static Blanket of Air To a 50-mL 3-neck flask under air was added 25 mL of 100 mM pH 3.0 potassium phosphate buffer and 330 µL of 6,6-dimethyl-3-azabicyclo[3.1.0]hexane to give a homogeneous solution. The pH was adjusted to approximately 7.5 using concentrated $H_3PO_4$. To the pH adjusted solution was added 60 µL of *A. niger* catalase suspension (Sigma Aldrich; catalog number C-3515) and 150 mg of monoamine oxidase powder (prepared by the method of Example 2) with SEQ ID NO 4, 6 or 8 in pH 8.0 potassium phosphate buffer. The resulting pale yellow solution was stirred under air for 24 hours. The pH was maintained at 7.4 via feedback controlled addition of 1 N NaOH in 1-5 µL portions. The reaction was then quenched with 10 N NaOH to bring the pH to approximately 14. A sample of the mixture was extracted with $CDCl_3$. After phase separation via centrifuge (6000 rpm for 5 minutes), $^1$H-NMR analysis indicated at least 95% conversion of the amine (1) to the imine (2). Chiral GC analysis by the method of Example 4 showed (1R,5S)-imine enantiomer (2). The (1S,2R) enantiomer was not detected.

Example 12

Monoamine Oxidase Catalyzed Desymmetrization of 6,6-dimethyl-3-azabicyclo[3.1.0]hexane (1) to (1R, 5S)-6,6-dimethyl-3-azabicyclo[3.1.0]hex-2-ene (2) Under a Blanket of Oxygen To a 50-mL 3-neck flask under air was added 25 mL of 100 mM pH 3.0 potassium phosphate buffer and 330 µL of 6,6-dimethyl-3-azabicyclo[3.1.0]hexane to give homogeneous solution. The pH was adjusted to approximately 7.5 with concentrated $H_3PO_4$. To the pH adjusted solution was added 60 µL of *A. niger* catalase suspension (Sigma Aldrich; catalog number C-3515) and 150 mg of monoamine oxidase powder of polypeptides of SEQ ID NO 4, 6 or 8 (prepared by the method of Example 2) in pH 8.0 potassium phosphate buffer. The headspace was flushed through with a stream of oxygen and the resulting pale yellow solution was stirred under air for 24 hours. The pH was maintained at 7.4 via feedback controlled addition of 1 N NaOH in 1-5 µL portions. The reaction was quenched with 10 N NaOH to bring the pH to approximately 14. A sample of the mixture was extracted with $CDCl_3$. After phase separation via centrifuge (6000 rpm for 5 minutes), $^1$H-NMR analysis indicated at least 95% conversion of the amine (1) to the imine (2). Chiral GC analysis by the method of Example 4 showed (1R,5S)-imine enantiomer (2). The (1S,2R) enantiomer was not detected.

Example 13

Monoamine Oxidase Catalyzed Desymmetrization of 6,6-dimethyl-3-azabicyclo[3.1.0]hexane (1) to (1R, 5S)-6,6-dimethyl-3-azabicyclo[3.1.0]hex-2-ene with Air Sparging in the Presence of Bisulfite To a 100-mL flask was added 40 mL of dH2O and 1.8 mL of 6,6-dimethyl-3-azabicyclo[3.1.0]hexane to give homogeneous solution with a pH of approximately 11.4. To this solution was added 2.7 g of Na2S2O5 to provide a homogeneous solution and the pH was adjusted to approximately 7.5 by addition of about 1 mL of 8 N NaOH. To this solution was added 60 µL of Antifoam-204 (Sigma, catalog number A-6226) 120 µL of *A. niger* catalase suspension (Sigma Aldrich; catalog number C-3515) and 300 mg of monoamine oxidase powder of polypeptide of SEQ ID NO: 8 (prepared by the method of Example 2) in 10 mL of 100 mM pH 8.0 potassium phosphate buffer. Air was sparged into the reaction mixture through fritted glass and the resulting pale yellow solution was stirred with air sparging for 24 hours at room temperature (about 21° C.) for 24 hours. The pH was maintained at 7.4 via feedback controlled addition of 2.5 N NaOH in 1 µL portions. The reaction was quenched and the imine-bisulfite adduct (the aminosulfonate) was broken to free imine with 10 N NaOH to bring the pH to approximately 14 and the product was extracted isolated by extraction into MTBE. Following phase separation, (1R,5S)-6,6-dimethyl-3-azabicyclo[3.1.0]hex-2-ene was isolated via distillation in 86% yield. Analysis by $^1$H-NMR in $CDCl_3$ (as in Example 10) confirmed conversion of compound (1) to the imine compound (2). Chiral GC analysis by the method of Example 4 showed (1R,5S)-imine enantiomer (2). The (1S,2R) enantiomer was not detected.

The (1R,5S)-6,6-dimethyl-3-azabicyclo[3.1.0]hex-2-ene so obtained was treated with 1.0 equiv. of $NaHSO_3$ in $D_2O$. $^1$H-NMR analysis indicated quantitative conversion to the bisulfite adduct ($^1$H-NMR (300 MHz, $D_2O$) spectrum: δ 4.8 (d, J=1, 1H(NC(H)SO3; major diastereomer), 4.5 (d, J=5, 1H(NC(H)SO3; minor diastereomer), 3.4-3.6 (m, 2H; minor diastereomer), 3.25 (dd, J=3, 10, 1H; major diastereomer), 3.05 (dd, 1H; J=1, 10; major diastereomer), 1.65 (m, 1H; major and minor diastereomer), 1.55 (m, 1H, major and minor diastereomer), 1.22 (s, 3H; minor diastereomer), 1.15 (s, 3H; minor diastereomer), 1.10 (s, 3H, major diastereomer), 1.00 (s, 3H; minor diastereomer).

Example 14

Monoamine Oxidase Catalyzed Desymmetrization of 6,6-dimethyl-3-azabicyclo[3.1.0]hexane to (1R,5S)-6,6-dimethyl-3-azabicyclo[3.1.0]hex-2-ene with Air Sparging and Concomitant Addition of the Substrate and Bisulfite To the 500-mL 4-neck flask at room temperature (about 21° C.) fitted with an overhead stirrer at 300 rpm was added 150 mL of Milli-Q water and 1.2 mL (approximately 1.0 g; approximately 9 mmol) of 6,6-dimethyl-3-azabicyclo[3.1.0]hexane to give a homogeneous solution with a pH of 11.8. $Na_2S_2O_5$ was added in portions until a pH 7.5 was achieved. To the colorless solution was added 300 of Antifoam-204 (Sigma catalog number A-6226) and 600 µL of *A. niger* catalase suspension (Sigma Aldrich; catalog number C-3515) to give a colorless solution at pH 7.5. To this solution was added 1.5 g of a monoamine oxidase powder of polypeptide of SEQ ID NO: 8 (prepared by the method of Example 3) to give a yellow solution. An air sparging probe was inserted and air was sparged into the reaction at a rate of ~60 mL/min and it was noted that the pH of the reaction mixture began to drop immediately. The pH was maintained via feedback controlled addition of 2 N NaOH. After about 30 minutes, the pH remained stable and no further base addition occurred. After an additional 10 minutes (40 minutes total), 120 mL of a 6,6-dimethyl-3-azabicyclo[3.1.0]hexane/$NaHSO_3$ solution (20.8 g of 6,6-dimethyl-3-azabicyclo[3.1.0]hexane with 150 mL of $dH_2O$ and enough $Na_2S_2O_5$ to reach pH 7.2) was added to the reaction mixture at a rate of 0.25 mL/min. The pH of the reaction mixture began to drop immediately and addition of 2 N NaOH was resumed. Addition of 6-dimethyl-3-azabicyclo[3.1.0]hexane/$NaHSO_3$ was completed after about 8 hours (9 hours of total reaction time). The base addition continued and the base addition rate increased after the substrate addition was completed. The reaction was quenched with 10 N NaOH to bring the pH to approximately 14 (and break the imine-bisulfite adduct) and the mixture extracted with MTBE. Following phase separation, (1R,5S)-6,6-dimethyl-3-azabicyclo[3.1.0]hex-2-ene was isolated via distillation of the MTBE solution in 72% yield. Analysis by $^1$H-NMR in $CDCl_3$ (as in Example 10) confirmed conversion of compound (1) to the imine compound (2). Chiral GC analysis by the method of Example 4 showed (1R,5S)-imine enantiomer (2). The (1S, 2R) enantiomer was not detected.

Example 15

Preparation of (1R,2S,5S)-6,6-dimethyl-3-azabicyclo [3.1.0]hexane-2-carbonitrile (Static Substrate Mode)

To a 100-mL flask was added 40 mL of $dH_2O$ and 1.8 mL of 6,6-dimethyl-3-azabicyclo[3.1.0]hexane to provide a homogeneous solution with a pH of approximately 11.4. To this solution was added 2.7 g of $Na_2S_2O_5$ to provide a homogeneous solution and the pH was adjusted to about 7.5 with approximately 1 mL of 8 N NaOH. To this solution was added 60 µL of Antifoam-204 (Sigma catalog number A-6226), 120 µL of *A. niger* catalase suspension (Sigma Aldrich; catalog number C-3515) and 300 mg of monoamine oxidase powder of the polypeptide of SEQ ID NO 8 (prepared by the method of Example 2) in 10 mL of 100 mM pH 8.0 potassium phosphate buffer. Air was sparged into the reaction mixture through fritted glass at a rate of ±10 mL/min and the resulting pale yellow solution was stirred under air for 24 hours at room temperature (about 21° C.) for 24 hours. Throughout, the pH was maintained at 7.4 via feedback controlled addition of 2.5 N NaOH in 1 portions. After 24 hours, 1.0 g (1.3 equiv) of NaCN was added to the reaction mixture then comprising (1R,2S,5S)-6,6-dimethyl-3-azabicyclo[3.1.0]hexane-2-sulfonate. After stirring at room temperature (about 21° C.) for an additional 15 minutes, the mixture was extracted with MTBE. (2-Me-THF can also be used for the extraction.) Following phase separation and solvent removal, 1.78 g (90% yield) of (1R,2S,5S)-6,6-dimethyl-3-azabicyclo[3.1.0]hexane-2-carbonitrile was isolated a pale yellow solid. Analysis by $^1$H-NMR in CDCl$_3$ confirmed preparation of (1R,2S,5S)-6,6-dimethyl-3-azabicyclo[3.1.0]hexane-2-carbonitrile ($^1$H-NMR (300 MHz, CDCl$_3$) spectrum: δ 3.92 (d, J=1.2, 1H, NC(H)(CN)), 3.25 (m, 1H), 2.96 (dd, J=2.1, 17.0), 1.48 (dd; J=1.2, 12.2; 1H), 1.42 (m, 1H), 1.13 (s, 3H), 1.11 (S, 3H)).

When a reaction mixture comprising (1R,2S,5S)-6,6-dimethyl-3-azabicyclo[3.1.0]hexane-2-sulfonate was so produced and treated with 3.0 equiv. of NaCN at room temperature for 12 hours, ~25% of the undesired cis stereoisomer (1R,2R,5S)-6,6-dimethyl-3-azabicyclo[3.1.0]hexane-2-carbonitrile was observed in mixture with the desired trans ((1R, 2S,5S) stereoisomer. $^1$H-NMR in CDCl$_3$ showed the cis-aminonitrile methine proton as a doublet (J=4.2) at 4.22 ppm.

Example 16

Preparation of (1R,2S,5S)-6,6-dimethyl-3-azabicyclo [3.1.0]hexane-2-carbonitrile (Continuous Substrate Addition Mode)

Step 1. To a 500-mL 4-neck flask at room temperature (about 21° C.) fitted with an overhead stirrer (300 rpm) was added 150 mL of Milli-Q water and 1.2 mL (approximately 1.0 g and 9 mmol) of 6,6-dimethyl-3-azabicyclo[3.1.0]hexane to give a homogeneous solution with a pH of 11.8. Na$_2$S$_2$O$_5$ was added in portions until the pH reached 7.5. To the colorless solution was added 300 µL of Antifoam-204 (Sigma catalog number A-6226) and 600 µL of *A. niger* catalase suspension (SigmaAldrich; catalog number C-3515) to give a colorless solution at pH 7.5. To this solution was added 300 mg of a monoamine oxidase powder (prepared by the method of Example 3) with SEQ ID NO 12 to provide a yellow solution. An air sparging probe (airflow rate of ~60 mL/min) was inserted and the pH of the reaction mixture began to drop immediately. The pH was maintained via feedback controlled addition of 2 N NaOH. After approximately 40 minutes, the pH remained stable and no further base addition occurred. After an additional 10 minutes (50 minutes total), 150 mL of 6,6-dimethyl-3-azabicyclo[3.1.0]hexane NaHSO$_3$ solution (26.1 g of 6,6-dimethyl-3-azabicyclo[3.1.0]hexane with 160 mL of dH$_2$O and enough Na$_2$S$_2$O$_5$ to reach pH 7.2) was added to the reaction mixture at a rate of 0.12 mL/min. The pH of the reaction mixture began to drop immediately and addition of 2 N NaOH was resumed. The 6,6-dimethyl-3-azabicyclo[3.1.0]hexane/NaHSO$_3$ addition was completed after approximately 21 hours (approximately 22 hours of total reaction time). Base addition continued at an increased rate after substrate addition was completed. After 24 hours, the reaction was judged to be complete by $^1$H NMR analysis.

Step 2. After 24 hours, the reaction was judged to be complete by $^1$H-NMR analysis, 10.0 g of NaCN (1.11 equiv.) was added to the reaction mixture to give a milky reaction mixture with pH 9.9. After 24 hours, the reaction was judged to be complete by $^1$H NMR analysis. After 30 minutes, the reaction was extracted with 300 mL of MTBE. The lower aqueous phase was drained off (approximately 250 mL) and the upper organic layer filtered through 6 g (2" diameter×¼" height) of Celite®. The Celite® was rinsed with 300 mL of MTBE and the MTBE used in the Celite® rinse was used to extract the aqueous phase. The organic phases were combined and concentrated under reduced pressure using a rotatory evaporator at 40° C. for 1 hour to give a white solid. The white solid was further dried under reduced pressure for 30 minutes to give 23.9 g (95% yield) of (1R,2S,5S)-6,6-dimethyl-3-azabicyclo[3.1.0]hexane-2-carbonitrile.

Example 17

Preparation of 6,6-dimethyl-3-azabicyclo[3.1.0]hexane-2-carboxylic Acid Methyl Ester The (1R,2S,5S)-6,6-dimethyl-3-azabicyclo[3.1.0]hexane-2-carbonitrile prepared according to Example 16 or 17 is converted to the corresponding substantially enantiomerically pure (1R,2S,5S)-6,6-dimethyl-3-azabicyclo[3.1.0]hexane-2-carboxylic acid methyl ester by the procedure described in PCT International Application Publication WO 2007/075790.

Example 18

Preparation of (1R,2S,5S)-6,6-dimethyl-3-azabicyclo [3.1.0]hexane-2-carbonitrile, Effect of NaCN Equivalents and Reaction Time on the Trans/Cis Ratio of the Aminonitrile The procedure was the identical to that of Example 15 up to the addition of NaCN, with the exceptions that the monoamine oxidase power of SEQ ID NO 8 was prepared by the method of Example 3. After 24 hours, NaCN was added portion-wise to the reaction mixture as shown in Table 5 (1.0 equivalent of NaCN was 720 mg of 95% NaCN). After each prescribed time interval, a 200 µL aliquot was taken, extracted with 1 mL of CDCl$_3$ and then analyzed by $^1$H-NMR. The trans/cis ratio between (the ratio between the desired 2S and undesired 2R epimers of (1R,5S)-6,6-dimethyl-3-azabicyclo [3.1.0]hexane-2-carbonitrile) of was determined by the $^1$H-NMR integration of the aminonitrile methine proton resonance (trans=doublet at 3.92 ppm; cis=doublet at 4.22 ppm).

TABLE 5

| Time [min] | NaCN added [equiv.] | Total NaCN [equiv.] | Time since previous addition [min] | pH | % conv. [$^1$H-NMR] | Trans/cis [$^1$H-NMR] |
|---|---|---|---|---|---|---|
| 0 | 1.0 | 1.0 | 0 | 10.5 | ND[1] | ND |
| 20 | — | 1.0 | 20 | 10.5 | 92 | >100[2] |
| 60 | — | 1.0 | 60 | 10.6 | 92 | >100 |
| 90 | 0.5 | 1.5 | 30 | 10.8 | 97 | >100 |
| 150 | — | 1.5 | 60 | 10.8 | 96 | 26 |
| 210 | 0.5 | 2.0 | 60 | 11.0 | 98 | 19 |
| 230 | 1.0 | 3.0 | 20 | 11.1 | 98 | 16 |
| 350 | — | 3.0 | 120 | 11.2 | 98 | 12 |

[1]ND = not determined.
[2]>100 means cis methine resonance not detected.

After the final aliquot, the reaction mixture was extracted with 100 mL of ethyl acetate and filtered through coarse sand to give a clean phase separation. 20 mL of heptanes was added to the organic phase. The organic phase was evaporated to dryness via rotary vacuum evaporation at 40° C. for 1 h. $^1$H-NMR analysis indicated that the trans/cis ratio remained at 12:1.

Example 19

Preparation of (1R,2S,5S)-6,6-dimethyl-3-azabicyclo [3.1.0]hexane-2-carbonitrile; Process Robustness Step 1. To a 500-mL 4-neck flask at room temperature (about 21° C.) fitted with an overhead stirrer (300 rpm) was added 150 mL of Milli-Q water and 1.2 mL (approximately 1.0 g and 9 mmol) of 6,6-dimethyl-3-azabicyclo[3.1.0]hexane to give a homogeneous solution with a pH of 11.8.

Na$_2$S$_2$O$_5$ was added in portions until the pH reached 7.5. To the colorless solution was added 300 μL of Antifoam-204 (Sigma catalog number A-6226) and 600 μL of *A. niger* catalase suspension (Sigma Aldrich; catalog number C-3515) to give a colorless solution at pH 7.5. To this solution was added 300 mg of a monoamine oxidase powder (prepared by the method of Example 3) with SEQ ID NO 12 to provide a yellow solution. An air sparging probe (airflow rate of ~60 mL/min) was inserted and the pH of the reaction mixture began to drop immediately. The pH was maintained via feedback controlled addition of 2 N NaOH. After approximately 40 minutes, the pH remained stable and no further base addition occurred. After an additional 10 minutes (50 minutes total), 150 mL of 6,6 dimethyl-3-azabicyclo[3.1.0]hexane NaHSO$_3$ solution (26.1 g of 6,6-dimethyl-3-azabicyclo [3.1.0]hexane with 160 mL of dH$_2$O and enough Na$_2$S$_2$O$_5$ to reach pH 7.2) was added to the reaction mixture at a rate of 0.12 mL/min. The pH of the reaction mixture began to drop immediately and addition of 2 N NaOH was resumed. The 6,6-dimethyl-3-azabicyclo[3.1.0]hexane/NaHSO3 addition was completed after approximately 21 hours (approximately 22 hours of total reaction time). Base addition continued at an increased rate after substrate addition was completed. After 24 hours, the reaction was judged to be complete by $^1$H NMR analysis.

Step 2. After 24 hours, 13.5 g of NaCN (1.5 equiv.) was added to the reaction mixture to give a milky reaction mixture with pH 9.9. 200 μL aliquots was taken after the mixture had been stirring at room temperature for 15 and for 45 minutes. The aliquots were extracted with 1 mL of CDCl$_3$ and the extract was analyzed by $^1$H-NMR. The cis-stereoisomer was below the $^1$H-NMR detection limit at both time points.

After ~60 minutes since the NaCN addition, the reaction was extracted with 300 mL of MTBE. The lower aqueous phase was drained off (approximately 250 mL) and the upper organic layer filtered through 6 g (2" diameter×¼" height) of Celite®. The Celite® was rinsed with 300 mL of MTBE and the MTBE used in the Celite® rinse was used to extract the aqueous phase. The organic phases were combined and concentrated under reduced pressure using a rotatory vacuum evaporator at 40° C. for 1 hour to give a white solid. The white solid was further dried under reduced pressure for 30 minutes to give 22.5 g (90% yield) of (1R,2S,5S)-6,6-dimethyl-3-azabicyclo[3.1.0]hexane-2-carbonitrile. The cis (2R) epimer was below the $^1$H-NMR detection limit.

This example illustrates that this aminonitrile remains in stereometrically pure form after one hour at room temperature at pH 9.9 and in the presence of 0.5 equiv excess cyanide.

Example 20

Preparation of (1R,2S,5S)-6,6-dimethyl-3-azabicyclo [3.1.0]hexane-2-carbonitrile; Process Robustness Step 1. The procedure was identical to Step 1 of Example 18.

Step 2. After 24 hours, 11.0 g of NaCN (1.22 equiv) was added to the reaction mixture to give a milky reaction mixture with pH 9.9. After stirring at room temperature for 10 minutes, a 200 μL aliquot was taken, extracted with 1 mL of CDCl$_3$. $^1$H-NMR analysis of the extract solution indicated complete conversion to (1R,2S,5S)-6,6-dimethyl-3-azabicyclo[3.1.0]hexane-2-carbonitrile, the trans aminonitrile with no detectable cis 2R stereoisomer.

The reaction mixture was stirred at room temperature for an additional 16 hours. $^1$H-NMR analysis after 16 hours indicated a trans/cis aminonitrile ratio of ~15:1 (the trans/cis ratio was determined by the $^1$H-NMR integration of the aminonitrile methine proton: trans=doublet at 3.92 ppm; cis=doublet at 4.22 ppm).

Example 21

Monoamine Oxidase Catalyzed Desymmetrization of octahydrocyclopenta[c]pyrrole to (3aS,6aR)-1,3a,4, 5,6,6a-hexahydrocyclopenta[c]Pyrrole Under Static Air To a 50-mL 3-neck flask under air was added 25 mL of 100 mM pH 8.0 potassium phosphate buffer and 375 mg of octahydrocyclopenta[c]pyrrole hydrochloride followed by adjustment of the pH to approximately 7.5 by addition of 1 N NaOH. To the pH adjusted solution was added 60 μL of *A. niger* catalase suspension (Sigma Aldrich; catalog number C-3515) and 150 mg of monoamine oxidase powder (prepared by the method of Example 2) with SEQ ID NO 4 in pH 8.0 potassium phosphate buffer. The resulting pale yellow solution was stirred under air for 24 hours during which time the pH was maintained at 7.4 via feedback controlled addition of 1 N NaOH in 1-5 μL portions. The reaction was quenched with 10 N NaOH to bring the pH to approximately 14 and the product was isolated by extraction into CDCl$_3$ and the conversion was analyzed by $^1$H-NMR, showing the formation of 1,3a,4,5,6,6a-hexahydrocyclopenta[c]pyrrole.

When the monoamine oxidase with SEQ ID NO. 4, used in this example, was identified in high throughput screening, the chiral GC assay method of Example 5 showed that it oxidized octahydrocyclopenta[c]pyrrole to the desired (3aR,6aS)-imine (4). The (3aS,6aR) enantiomer was not detected.

Example 22

Preparation of (1S,3aR,6aS)-octahydrocyclopenta[c] pyrrole-1-carbonitrile

To a 50-mL 3-neck flask under air was added 25 mL of 100 mM pH 8.0 potassium phosphate buffer and 400 mg of octahydrocyclopenta[c]pyrrole hydrochloride, 500 mg of Na$_2$S$_2$O$_5$ and the pH was adjusted to approximately 7.5 with 10 N NaOH. To the pH adjusted solution was added 30 pt of *A. niger* catalase suspension (Sigma Aldrich; catalog number C-3515) and 300 mg of monoamine oxidase powder (prepared by the method of Example 2 (with SEQ ID NO 10 in pH 8.0 potassium phosphate buffer. The resulting pale yellow solution was stirred under air for 24 hours during which time the pH was maintained at 7.5 via feedback controlled addition of 1 N NaOH in 1-5 μL portions. After stirring for 48 hours, 300 mg of NaCN was added to the reaction mixture raising the pH to ±9.9. After stirring at room temperature (about 21° C.) for an additional 1 hour, the mixture was extracted with ethyl acetate. After phase separation and solvent evaporation, 316 mg of octahydrocyclopenta[c]pyrrole-1-carbonitrile was isolated (82% yield). $^1$H-NMR showed ~90% (1S,3aR,6aS), "trans" and ±10% of the (1R,3aR,6aS) epimer, "cis." ($^1$H-NMR (300 MHz, CDCl$_3$) spectrum: δ 3.95 (d, J=6.6, cis aminonitrile methine H), 3.62 (d, J=1.2; trans aminonitrile methine H), 3.15 (m, 1H), 2.71 (m, 2H), 2.62 (m, 1H), 1.63-1.92 (m, 3H), 1.55 (m, 1H), 1.22-1.45 (m, 3H)).

Example 23

Preparative Scale Production of (3aR,6aS)-1,3a,4,5, 6,6a-hexahydro-cyclo-penta[c]-pyrrole, Compound (4), and its corresponding dimer, Compound (5)

To a 3-L 3-neck flask jacketed at 20° C. and stirred at 300 rpm was added 500 mL of dH$_2$O and 20 mL of a 25 wt % octahydrocyclopenta[c]pyrrole solution in water. The pH was adjusted to approximately 7.6 with concentrated. $H_3PO_4$ to give a colorless homogeneous solution. To this solution was added 2.0 mL of *A. niger* catalase suspension (Sigma Aldrich; catalog number C-3515) and 5.0 g of monoamine oxidase powder of the polypeptide of SEQ ID NO: 16 (prepared by the method of Example 3) to give a pale yellow solution. The head space of the vessel was swept with dry air at approximately 0.2 L/min. The pH of the reaction was maintained at 7.5 by feedback controlled addition of the 25 wt % octahydrocyclopenta[c]pyrrole solution in water in 20-100 µL portions until 380 mL have been added. (The amine in neutral solution is protonated; the imine is not. A proton is released by the reaction and must be neutralized to maintain the pH. In this example, the amine itself is the base used as the titrant for the pH-stat.) After 380 mL of the 25 wt % octahydrocyclopenta[c]pyrrole solution in water had been added, the pH was maintained by feedback controlled addition of 1 N NaOH to complete the reaction (corresponding to the initial 5 g (45 mmol) of the substrate. After no further NaOH consumption was observed, an aliquot of the slurry was taken, filtered, and the solid was air-dried.

$^1$H-NMR spectra of the solid dissolved in various solvents showed varying proportions of the imine (3aR,6aS) octahydrocyclopenta[c]pyrrole (4) and its dimer (5) in solution. $^1$H-NMR in $D_6$-DMSO (300 MHz) showed dimer and free imine was not detected (spectrum: δ 3.11 (t, J=8.2; 1H), 2.45 (m, 1H), 2.33 (m, 1H), 1.85 (dd, J=7.2, 8.1, 1H), 1.31-1.58 (m, 7H)). $^1$H-NMR in $CDCl_3$ (300 MHz) showed a mixture of imine and dimer (spectrum: δ 3.22 (m, 1H), 2.65 (m, 1H), 2.30-2.40 (m, 2H), 1.89 (m, 1H), 1.50-1.70 (m, 5H), 1.43 (m, 1H)). $^1$H-NMR in 17% $D_3PO_4/D_2O$ (300 MHz) showed only the protonated imine monomer (spectrum: δ 7.6-8.2 (br, 1H), 3.5-3.8 (br, 1H), 2.8-3.5 (br, 2H), 2.2-2.8 (br, 1H), 0.5-1.7 (br, 6H)).

To the bulk of the reaction mixture was added 100 mL of concentrated HCl to give a yellow suspension with pH ~0 (to break the dimer to the protonated imine). The yellow suspension was centrifuged at 8000 at 4° C. for 10 minutes. The resulting yellow supernatant was decanted and returned to the reaction vessel. The white paste (pelleted by the centrifugation) was resuspended in 100 mL of $dH_2O$ and filtered through filter paper. The residue was rinsed with $dH_2O$ (1×100 mL). All acidic aqueous solutions so obtained, containing (3aS,6aR)-1,3a,4,5,6,6a-hexahydrocyclopenta[c]pyrrole hydrochloride were combined and used directly in the cyanation reaction to the aminonitrile.

When the monoamine oxidase with SEQ ID NO. 16, used in this example, was identified in high throughput screening, the chiral GC assay of Example 5 showed that it oxidized octahydrocyclopenta[c]pyrrole to the desired (3aR,6aS)-imine (4). The (3aS,6aR) enantiomer was not detected.

Example 24

Monoamine Oxidase Catalyzed Desymmetrization of octahydrocyclopenta[c]pyrrole to (3aS,6aR)-1,3a,4, 5,6,6a-hexahydrocyclopenta[c]pyrrole and its Corresponding Dimer Under Static Air or Oxygen; Product Isolation Via Extraction To a 3-L 3-neck flask jacketed at 20° C. and stirred at 300 rpm was added 500 mL of $dH_2O$ and 20 mL of a 25 wt % octahydrocyclopenta[c]pyrrole solution in water. The pH was adjusted to approximately 7.6 with concentrated $H_3PO_4$ to provide a colorless, homogeneous solution to which 2.0 mL of *A. niger* catalase suspension (Novozyme; "Catalyzyme 101") and 5.0 g of monoamine oxidase powder of the polypeptide of SEQ ID NO: 16 (prepared by the method of Example 3) were added to give a pale yellow solution. The head space of the vessel was swept with dry air at approximately 0.2 L/min. The pH of the reaction was maintained at 7.5 via feedback controlled addition of the 25 wt % octahydrocyclopenta[c]pyrrole solution in water in 20-100 µL portions until 380 mL have been added. (The amine in neutral solution is protonated; the imine is not. A proton is released by the reaction and must be neutralized to maintain the pH. In this example, the amine itself is the base used as the titrant for the pH-stat.) After 380 mL of the 25 wt % octahydrocyclopenta[c]pyrrole solution in water had been added, the pH was maintained by addition of 1 N NaOH to complete the reaction (corresponding to the initial 5 g (45 mmol) of the substrate). After no further NaOH consumption was observed, 1800 mL of MTBE was added to the heterogeneous reaction mixture that was then heated to 45° C. After filtration through Celite®, the lower aqueous phase was discarded and the upper organic phase extracted with 10% citric acid, and the acidic aqueous solution containing (3aS,6aR)-1,3a,4,5,6,6a-hexahydrocyclopenta[c]pyrrole hydrochloride was used directly in the preparation of (1R,2S,5S)-6,6-dimethyl-3-azabicyclo[3.1.0]hexane-2-carboxylic acid according to the method of Example 29.

Example 25

Preparative Scale Production of the Dimer of (3aR,6aS) octahydrocyclopenta[c]pyrrole, Compound (3)

To a 500 mL 3-neck flask jacketed at 30° C. under air and stirred at 300 rpm was added 100 mL of $dH_2O$ and 2.0 mL of a 25 wt % octahydrocyclopenta[c]pyrrole solution in water (0.5 g of the substrate). The pH was adjusted to approximately 7.8 with concentrated. $H_3PO_4$ to give a colorless homogeneous solution. To this solution was added 0.2 mL of *A. niger* catalase suspension (Novozyme "Catalyzyme 101) and 0.25 g of monoamine oxidase powder of the polypeptide of SEQ ID NO 36 (prepared by the method of Example 3). The pH of the reaction began to drop immediately and the pH was maintained at pH 7.7 via feedback-controlled addition of the 25 wt % octahydrocyclopenta[c]pyrrole solution in water. After 2 hours, an additional 0.25 g of the monoamine oxidase powder was added. The dimer of (3aR,6aS) octahydrocyclopenta[c]pyrrole began to precipitate from the reaction and the reaction mixture became a white slurry for the duration of the experiment. After an additional 2 hours (4 hours total), the head space was swept with ~0.6 mL/min of oxygen and the oxygen sweep was maintained for the duration of the experiment. After 24 hours of total reaction time, an additional 0.5 g of the monoamine oxidase was added. After a total reaction time of 48.5 hours, a total of 32.3 mL of the 25 wt % octahydrocyclopenta[c]pyrrole solution in water had been added (total substrate reacted was 8.58 g). The reaction mixture was transferred to a 500 mL one-neck flask fitted with a short path distillation head and the set-up was placed in a heating mantle. Upon heating the heating mantle to 160° C., the dimer began to steam distill to the receiving flask immersed in an ice bath. The temperature of the vapor phase was ±96° C. After ±30 minutes, ~½ of the reaction mass had been distilled over and the temperature of the vapor phase was ~98° C. Distillation was stopped at this point. The suspension of the white solid in water in the receiving flask was filtered through a coarse fritted funnel and the white solid was allowed to air dry for 2 hours to give 7.17 g (84% yield) of the dimer of (3aR, 6aS) octahydrocyclopenta[c]pyrrole Example 26

Monoamine Oxidase Catalyzed Desymmetrization of octahydrocyclopenta[c]pyrrole to (3aS,6aR)-1,3a,4, 5,6,6a-hexahydrocyclopenta[c]pyrrole and its Corresponding Dimer Under Static Air; Product Separation Via Steam Distillation To a 3-L 3-neck flask jacketed at 20° C. and stirred at 300 rpm was added 500 mL of $dH_2O$ and 20 mL of a 25 wt % octahydrocyclopenta[c]pyrrole solution in water. The pH was adjusted to approximately 7.6 with concentrated $H_3PO_4$ to give a colorless, homogeneous solution, to which 2.0 mL of *A. niger* catalase suspension (Novozyme; "Catalyzyme 101") and 5.0 g of monoamine oxidase powder of the polypeptide of SEQ ID NO: 16 (prepared by the method of Example 3) were added to give a pale yellow solution. The head space of the vessel was swept with dry air at approximately 0.2 L/min. The pH of the reaction was maintained at 7.5 via feedback controlled addition of the 25 wt % octahydrocyclopenta[c]pyrrole solution in water in 20-100 µL portions. The dimer of (3aR,6aS) octahydrocyclopenta[c]pyrrole to precipitated from the reaction and the reaction mixture became a white slurry. After 380 mL of the 25 wt % octahydrocyclopenta[c] pyrrole solution in water had been added, the product was separated from the reaction mixture via steam distillation (still head temperature ~98° C.). The receiver pot contained a suspension of the dimer of (3aS,6aR)-1,3a,4,5,6,6a-hexahydrocyclopenta[c]pyrrole in water. 1.1-1.2 equivalent of concentrated HCl was added to the receiver pot break the dimer and give a homogeneous solution of (3aS,6aR)-1,3a,4,5,6,6a-hexahydrocyclopenta[c]pyrrole hydrochloride in water. This solution was used directly to make (1S,3aR,6aS)-octahydrocyclopenta[c]pyrrole-1-carbonitrile in Example 27.

Example 27

Preparation of (1S,3aR,6aS)-octahydrocyclopenta[c] pyrrole-1-carbonitrile

The aqueous acidic solution of (3aS,6aR)-1,3a,4,5,6,6a-hexahydrocyclopenta[c]pyrrole hydrochloride prepared in Example 26 was cooled to 0° C. and stirred at 300 rpm. To the chilled solution at 0° C. was added 50 g NaCN in 100 mL of $dH_2O$ at 3 mL/min. (Neutralization of the hydrochloride salt solution by cyanide generated HCN in situ). 2 hours after the NaCN addition began, 1000 mL of toluene (pre-chilled in an ice bath) was added to give a bi-phasic mixture, to which a saturated solution of $K_2CO_3$ was added a rate of 10 mL/min until the pH of the aqueous phase reached 9.8. The lower, aqueous phase was then removed using a cannula and treated with bleach (to destroy remaining cyanide) prior to disposal. The upper organic suspension/emulsion was filtered through a 20 g bed (~¼" height×~3" diameter) of Celite® 545 at room temperature (about 21° C.) over approximately 15 minutes to give 1000 mL of colorless organic phase and ~300 mL of yellow aqueous phase along with approximately ~100 mL of a "rag phase" (an intermediate layer disposed between the upper organic phase and the lower aqueous phase). The Celite® pad was rinsed with toluene 2×100 mL. The solutions were combined in a separatory funnel and the aqueous phase and rag layer were drained out and treated with bleach for disposal. An aliquot of the organic phase was taken from the organic phase and evaporated to dryness. 1H-NMR (300 MHz, $CDCl_3$) analysis showed (1S,3aR,6aS)-octahydrocyclopenta[c]pyrrole-1-carbonitrile ("trans") and the its 1R epimer ("cis") present in a ~30:1 ratio ($^1$H-NMR (300 MHz, $CDCl_3$) spectrum: δ 3.95 (d, J=6.6, cis aminonitrile methine H), 3.62 (d, J=1.2; trans aminonitrile methine H), 3.15 (m, 1H), 2.71 (m, 2H), 2.62 (m, 1H), 1.63-1.92 (m, 3H), 1.55 (m, 1H), 1.22-1.45 (m, 3H)). The organic phase was cooled to approximately 0° C. and extracted twice with 250 mL of concentrated HCl (pre-chilled in an ice bath) after which a clean and immediate phase split occurred. (It was necessary to pre-chill the extraction solutions as the extractions were exothermic. The temperature of the solutions rose from ~4° C. to ~room temperature). The combined concentrated HCl extracts (approximately 600 mL total) containing (1S,3aR, 6aS)-octahydrocyclopenta[c]pyrrole-1-carbonitrile hydrochloride were combined and used directly to make (1S,3aR, 6aS)-octahydrocyclopenta[c]pyrrole-1-carboxylic acid hydrochloride in Example 28.

7.1 Example 28

Preparation of (1S,3aR,6aS)-octahydrocyclopenta[c] pyrrole-1-carboxylic Acid Hydrochloride The (1S,3aR,6aS)-octahydrocyclopenta[c]pyrrole-1-carbonitrile hydrochloride solution from the Example 27 was heated to reflux for 24 hours, after which time, approximately 300 mL of water/HCl was distilled off and the remaining solution cooled to approximately 50-60° C. To the warm solution was added 500 mL of toluene and the remaining water (approximately 100-120 mL) was distilled off as a toluene azeotrope. After all of water had been removed, the resulting heavy slurry suspension of brown solid and pale yellow toluene was cooled to room temperature (about 21° C.). The solid was collected on a filter funnel and rinsed with toluene (2×200 mL). The tan solid was air dried for 2 hours and further dried under vacuum overnight to give 159 g (72% overall yield from octahydrocyclopenta[c]pyrrole) of (1S, 3aR,6aS)-octahydrocyclopenta[c]pyrrole-1-carboxylic acid hydrochloride in 1:1 admixture with the $NH_4Cl$ co-product.
$^1$H-NMR of the salt admixture dissolved in $D_2O$ showed a trans/cis (1S/1R) ratio of approximately 17:1. ($^1$H-NMR (300 MHz, $D_2O$) spectrum: δ 4.32 (d, J=5.5; cis-amino acid methine), 3.85 (d, J=2.3; trans-amino acid methine), 3.50 (m, 1H), 3.65-3.88 (m, 3H), 1.20-1.80 (m, 6H)).

7.2 Example 29

Preparation of (1S,3aR,6aS)-octahydrocyclopenta[c] pyrrole-1-carboxylic Acid t-Butyl Ester Oxalic Acid 1:1 Salt from (1S,3aR,6aS)-octahydrocyclopenta[c] pyrrole-1-Carboxylic Acid Hydrochloride Step 1: To a 1650 mL thick-walled glass pressure bottle (Ace Glass, Inc., 8648-157) equipped with a magnetic stirring bar was charged 75 g (306.9 mmol) of the (1S,3aR,6aS)-octahydrocyclopenta[c]pyrrole-1-carboxylic acid hydrochloride/ammonium chloride admixture prepared in Example 28, 375 mL dichloromethane, and 497 mL t-butyl acetate. The resulting mixture was stirred vigorously at ambient temperature (about 21° C.) to break large aggregates to provide a free-stirring suspension. This suspension was cooled to an internal temperature of 0° C. using a brine-ice bath and 75.4 mL (1162 mmol) methanesulfonic acid was added dropwise over 15 minutes, during which the internal temperature rose to 5° C. The pressure bottle was sealed and the reaction mixture was allowed to warm to ambient temperature (about 21° C.) with vigorous stirring over 18 hours, during which the reaction mixture became a suspension of white inorganic salts in an amber solution. The mixture was cooled in an ice bath and the pressure bottle carefully vented and uncapped. The mixture was transferred to a 3 L flask and cooled in an ice bath with stirring. 400 mL of 50% (wt:wt) NaOH in water was added to the mixture over 35 minutes while maintaining its temperature below 20° C. The stirring was halted and the phases were allowed to separate. The organic phase (~850 mL) was removed to a separate vessel. The remaining aqueous phase and rag layer (pH 13, ~800 mL) were extracted with 375 mL dichloromethane. The organic phases were combined (~1250 mL) and washed with water (2×225 mL). The resulting organic phase was filtered to remove a rag layer and any insoluble material, and the solvent was removed by rotary vacuum evaporation to give 48.3 g dark-amber oil. The $^1$H NMR spectrum of the oil showed (1S,3aR,6aS)-octahydrocyclopenta[c]pyrrole-1-carboxylic acid t-butyl ester.

A second preparation following the same procedure yielded was 50.6 g of the trans-(1S,3aR,6aS)-octahydrocyclopenta[c]pyrrole-1-carboxylic acid t-butyl ester oil.

Step 2: 97.9 g (463.3 mmol) of (1S,3aR,6aS)-octahydrocyclopenta[c]pyrrole-1-carboxylic acid t-butyl ester from the two preparations according to Step 1 were dissolved in 750 mL t-butyl acetate and charged to a 3 L four-neck flask equipped with overhead mechanical stirring, a thermometer, addition funnel, and reflux condenser. With stirring at ambient temperature (~21° C.), a solution of 44.0 g (488.6 mmol) of oxalic acid in 750 mL 2-propanol was added dropwise over 37 minutes, increasing the mixture's temperature to 31° C. Solids began to precipitate after addition of ~50 mL of the oxalic acid solution, and resulted in a thick suspension after the addition of 450 mL. After addition of 500 mL of the oxalate solution, the precipitated solids redissolved to provide a dark yellow solution. Solids precipitated again rapidly after the addition of 600 mL of the oxalic solution and persisted through the end of the oxalic acid addition. This suspension was then heated 78° C. to provide a thin suspension which was allowed to cool passively with stirring to ambient temperature (~21° C.). After 16 hours since the cooling began, the precipitated solids were collected by filtration and washed successively with isopropanol (450 mL), isopropyl acetate (450 mL), and methyl t-butyl methyl ether (450 mL). The solids were dried in a vacuum oven (30° C., 25" vacuum, $N_2$ stream) to provide 118.1 g (1S,3aR,6aS)-octahydrocyclopenta[c]pyrrole-1-carboxylic acid t-butyl ester oxalic acid 1:1 salt (64% yield from (1S,3aR,6aS)-octahydrocyclopenta[c]pyrrole-1-carboxylic acid hydrochloride) as a dense, tan free flowing powder (99.7% purity by GC analysis), which exhibited the expected $^1$H-NMR spectrum for (1S,3aR,6aS)-octahydrocyclopenta[c]pyrrole-1-carboxylic acid t-butyl ester oxalic acid (1:1) salt.

Recrystallization of (1S,3aR,6aS)-octahydrocyclopenta[c]pyrrole-1-carboxylic acid t-butyl ester oxalic acid (1:1) salt: The tan powder from Step 2 above (118.1 g, 391.9 mmol) and isopropanol (1950 mL) were charged to a 3 L four neck flask equipped with a mechanical stirring, a thermometer, and a reflux condenser. The suspension was stirred and heated to 74° C. to completely dissolve the salt, resulting in a yellow solution. The stirring was slowed and the solution was allowed to cool passively to ambient temperature (~21° C.). After 20 hours since the cooling began, the precipitated solids collected by filtration and washed successively with isopropanol (1 L), isopropyl acetate (1 L), and methyl t-butyl methyl ether (1 L). The solids were dried in a vacuum oven (40° C., 28" vacuum, $N_2$ stream) to provide 110.45 g (1S,3aR,6aS)-octahydrocyclopenta[c]pyrrole-1-carboxylic acid t-butyl ester oxalic acid 1:1 salt (59.7% yield from (1S,3aR,6aS)-octahydrocyclopenta[c]pyrrole-1-carboxylic acid hydrochloride) as fine, off-white needles of 99.9% purity by GC analysis). Chiral GC analysis showed only the desired (1S,3aR,6aS)-stereoisomer. Its (2S)-epimer was not detected.

All patents, patent publications, journals, and other references cited in this disclosure are hereby incorporated-by-reference in their entirety.

What is claimed is:

1. An engineered monoamine oxidase enzyme which has one or more amino acid substitutions as compared to the amino acid sequence of SEQ ID NO: 2 and which comprises an amino acid sequence that has at least 88% identity to a sequence of any one of SEQ ID NO: 10, 12, 14, 16, 18, 20, or 36.

2. The monoamine oxidase enzyme of claim 1 in which the one or more amino acid substitutions as compared to the amino acid sequence of SEQ ID NO: 2 is selected from:
- glutamine at residue 99 is substituted with aspartic acid or glutamic acid;
- threonine at residue 135 is substituted with serine, glutamine, or asparagine;
- asparagine at residue 284 is substituted with aspartic acid or glutamic acid;
- alanine at residue 289 is substituted with valine, isoleucine, glycine, methionine, or leucine;
- lysine at residue 348 is substituted with serine, threonine, or glutamine;
- tyrosine at residue 365 is substituted with phenylalanine or tryptophan;
- phenylalanine at residue 382 is substituted with valine, isoleucine, alanine, glycine, methionine, or leucine; and
- serine at residue 465 is substituted with valine, isoleucine, alanine, glycine, methionine, or leucine.

3. The monoamine oxidase enzyme of claim 1 in which the one or more amino acid substitutions as compared to the amino acid sequence of SEQ ID NO: 2 is selected from:
- glutamine at residue 99 is substituted with glutamic acid;
- threonine at residue 135 is substituted with glutamine;
- asparagine at residue 284 is substituted with glutamic acid;
- alanine at residue 289 is substituted with valine;
- lysine at residue 348 is substituted with glutamine;
- tyrosine at residue 365 is substituted with tryptophan;
- phenylalanine at residue 382 is substituted with leucine; and
- serine at residue 465 is substituted with glycine.

4. The monoamine oxidase enzyme of claim 1 in which the enzyme is capable of converting the amine compound of compound (1), (1R,5S)-6,6-dimethyl-3-azabicyclo[3.1.0]hexane, to the corresponding imine compound of compound (2), (1R,5S)-6,6-dimethyl-3-azabicyclo[3.1.0]hex-2-ene.

5. The monoamine oxidase enzyme of claim 4 in which the enzyme is capable of converting compound (1) to compound (2) with a percent stereomeric excess of at least about 95% and at a rate that is improved over a reference polypeptide having the amino acid sequence of SEQ ID NO:2.

6. The monoamine oxidase enzyme of claim 4 in which the one or more amino acid substitutions as compared to the amino acid sequence of SEQ ID NO: 2 are selected from:
- alanine at residue 289 is substituted with valine;
- lysine at residue 348 is substituted with glutamine or proline;
- phenylalanine at residue 382 is substituted with leucine; and
- serine at residue 465 is substituted with glycine.

7. The monoamine oxidase enzyme of claim 4 in which the amino acid sequence has at least 88% identity to the amino acid sequence of any one of SEQ ID NO: 10, or 12, and which includes any one set of amino acid substitution combinations of SEQ ID NO: 10, or 12.

8. The monoamine oxidase enzyme of claim 4 in which the amino acid sequence is any one of SEQ ID NO: 10, or 12.

9. The monoamine oxidase enzyme of claim 1 in which the enzyme is capable of converting the amine compound of compound (3), (3aR,6aS)-octahydrocyclopenta[c]pyrrole, to compound (4), (3aS,6aR)-1,3a,4,5,6,6a-hexahydrocyclopenta[c]pyrrole.

10. The monoamine oxidase enzyme of claim 9 in which the enzyme is capable of converting compound (3) to compound (4) with a percent stereomeric excess of at least about 95% and at a rate that is improved over a reference polypeptide having the amino acid sequence of SEQ ID NO:2.

11. The monoamine oxidase enzyme of claim 9 in which the one or more amino acid substitutions as compared to the amino acid sequence of SEQ ID NO: 2 are selected from:
- glutamine at residue 99 is substituted with glutamic acid;
- threonine at residue 135 is substituted with glutamine;
- asparagine at residue 284 is substituted with glutamic acid;
- alanine at residue 289 is substituted with valine;
- lysine at residue 348 is substituted with glutamine or proline;
- tyrosine at residue 365 is substituted with tryptophan; and
- serine at residue 465 is substituted with glycine.

12. The monoamine oxidase enzyme of claim 9 in which the amino acid sequence has at least 88% identity to the amino acid sequence of any one of SEQ ID NO: 10, 14, 16, 18, 20, or 36, and which includes any one set of amino acid substitution combinations of SEQ ID NO: 10, 14, 16, 18, 20, or 36.

13. The monoamine oxidase enzyme of claim 9 in which the amino acid sequence is any one of SEQ ID NO: 10, 14, 16, 18, 20, or 36.

14. A polynucleotide encoding the engineered monoamine oxidase enzyme of claim 1.

15. An expression vector comprising the polynucleotide of claim 14.

16. A host cell comprising the polynucleotide of claim 14.

17. A method for preparing an engineered monoamine oxidase enzyme comprising culturing a host cell of claim 16.

18. A method for the production of (1R,2S,5S)—N-(4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide), the method comprising the step of converting compound (1), (1R,5S)-6,6-dimethyl-3-azabicyclo[3.1.0]hexane, to compound (2), (1R,5S)-6,6-dimethyl-3-azabicyclo[3.1.0]hex-2-ene, using the engineered monoamine oxidase enzyme of claim 1.

19. A method for the production of (N—((S)-1-cyclohexyl-2-((S)-1-((1S,3aR,6aS)-1-((R)-3-(2-(cyclopropylamino)-2-oxoacetyl)hexanoyl)hexahydrocyclopenta[c]pyrrol-2(1H)-yl)-3,3-dimethyl-1-oxobutan-2-ylamino)-2-oxoethyl) pyrazine-2-carboxamide, the method comprising the step of converting compound (3), (3aR,6aS)-octahydrocyclopenta[c]pyrrole, to compound (4), (3aS,6aR)-1,3a,4,5,6,6a- hexahydrocyclopenta[c]pyrrole, using the engineered monoamine oxidase enzyme of claim 1.

20. A method of preparing a substantially stereomerically pure compound according to structural formula II(a):

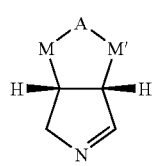

including salts and hydrates thereof, wherein:

A is O, $CR^1R^2$, —C≡C—, or —$CH_2$—$CH_2$—, wherein $R^1$ and $R^2$ are each independently selected from —H, —COOH, —X, —$NH_2$, —$CH_2NHC(NH)NH_2$, —$CX_3$, —$CH_3$, —$CH_2CH_3$, and wherein X is selected from F, Cl, and Br;

M and M' may both be present or may both be absent and when both M and M' are present M and M' are the same and are selected from O and $CR^3R^4$ wherein $R^3$ and $R^4$ are H, or $R^3$ or $R^4$ of M and $R^3$ or $R^4$ of M' form a methylene bridge;

with the provisos that (a) when M and M' are O, A is not O; and when A is O, M and M' are not O;

(b) A can be —CH═CH— or —$CH_2$—$CH_2$— when M and M' are $CR^3R^4$; and (c) when M and M' are $CR^3R^4$ and have one or more stereocenters, the stereocenters of M and M' are of opposite stereochemistry;

the method comprising contacting an amine compound according to structural formula I

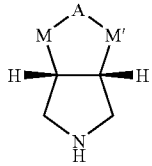

wherein A, M and M' are as defined for structural formula II(a) and II(b), with oxygen in the presence of the engineered monoamine oxidase enzyme of claim 1 with a co-factor under conditions in which the monoamine oxidase enzyme oxidizes the amine compound of structural formula I to a corresponding imine compound of structural formula II(a).

21. The method of claim 20, wherein the co-factor is selected from the group consisting of FAD, FMN, NAD, and NADP.

22. The method of claim 20, further comprising a component catalyzing a disproportionation of hydrogen peroxide ($H_2O_2$) to molecular oxygen and water.

23. The method of claim 22 in which the component is selected from the group consisting of Pd, Fe, and a catalase enzyme.

24. The method of claim 20, wherein the substantially stereomerically pure compound according to structural formula II(a) is a compound in which M and M' are absent and A is $CR^1R^2$, wherein $R^1$ and $R^2$ are each independently selected from —H, —COOH, —X, —$NH_2$, —$CH_2NHC(NH)NH_2$, —$CX_3$, —$CH_2CH_3$, and wherein X is selected from F, Cl, and Br.

25. The method of claim 24, wherein the substantially stereomerically pure compound according to structural formula II(a) is selected from the group consisting of:

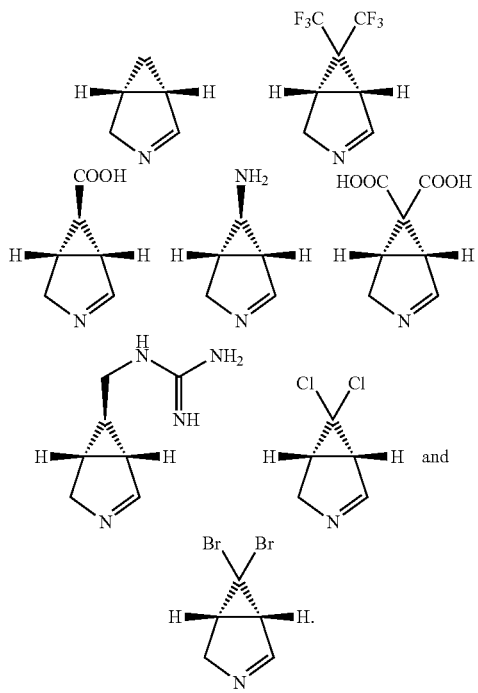

26. The method of claim 20, wherein the substantially stereomerically pure compound according to structural formula II(a) is

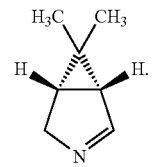

27. The method of claim 20, wherein the substantially stereomerically pure compound according to structural formula II(a) is a compound in which M and M' are —$CH_2$— and A is selected from the group consisting of —O—, —$CH_2$—, —$C(CH_3)_2$—, —$CH(CH_3)$—, —$C(C_2H_5)_2$—, —$CH(C_2H_5)$—, —$CF_2$—, —$CCl_2$—, —$CBr_2$—, —$C(CF_3)_2$—, —$CH(COOH)$—, —$C(COOH)_2$—, —$CH(NH_2)$—, and —$C(H_2)NHC(NH)NH_2$—.

28. The method of claim 27, wherein the substantially stereomerically pure compound according to structural formula II(a) is

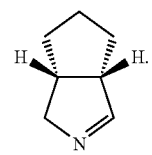

* * * * *

UNITED STATES PATENT AND TRADEMARK OFFICE
CERTIFICATE OF CORRECTION

| | | |
|---|---|---|
| PATENT NO. | : 8,178,333 B2 | |
| APPLICATION NO. | : 12/490190 | |
| DATED | : May 15, 2012 | |
| INVENTOR(S) | : Benjamin Mijts et al. | |

It is certified that error appears in the above-identified patent and that said Letters Patent is hereby corrected as shown below:

On the title page, item (75) Inventors, please delete:

"John M. Gruber, El Dorado Hills, CA (US); and
John D. Munger, Jr., Redwood City, CA (US)".

Signed and Sealed this
Eighteenth Day of December, 2012

David J. Kappos
*Director of the United States Patent and Trademark Office*